(12) United States Patent
Weber et al.

(10) Patent No.: US 9,186,209 B2
(45) Date of Patent: Nov. 17, 2015

(54) NERVE MODULATION SYSTEM HAVING HELICAL GUIDE

(75) Inventors: Jan Weber, Maastricht (NL); Aiden Flanagan, Co. Galway (IE); Tim O'Connor, Co. Galway (IE)

(73) Assignee: Boston Scientific Scimed, Inc., Maple Grove, MN (US)

( * ) Notice: Subject to any disclaimer, the term of this patent is extended or adjusted under 35 U.S.C. 154(b) by 286 days.

(21) Appl. No.: 13/554,459

(22) Filed: Jul. 20, 2012

(65) Prior Publication Data

US 2013/0165920 A1 Jun. 27, 2013

Related U.S. Application Data

(60) Provisional application No. 61/510,900, filed on Jul. 22, 2011.

(51) Int. Cl.
*A61B 18/14* (2006.01)
*A61N 1/05* (2006.01)
*A61B 18/00* (2006.01)

(52) U.S. Cl.
CPC .......... *A61B 18/1492* (2013.01); *A61N 1/0551* (2013.01); *A61B 2018/00511* (2013.01); *A61B 2018/00577* (2013.01)

(58) Field of Classification Search
CPC ................. A61B 18/1492; A61B 2018/00511; A61B 2018/00577
USPC .......................................................... 606/41
See application file for complete search history.

(56) References Cited

U.S. PATENT DOCUMENTS

| | | |
|---|---|---|
| 164,184 A | 6/1875 | Kidder |
| 1,167,014 A | 1/1916 | O'Brien |
| 2,505,358 A | 4/1950 | Gusberg et al. |
| 2,653,684 A | 9/1953 | Laptewicz et al. |
| 2,701,559 A | 2/1955 | Cooper |
| 3,108,593 A | 10/1963 | Glassman |
| 3,108,594 A | 10/1963 | Glassman |

(Continued)

FOREIGN PATENT DOCUMENTS

| | | |
|---|---|---|
| DE | 10038737 A1 | 2/2002 |
| EP | 0754075 | 1/1997 |

(Continued)

OTHER PUBLICATIONS

Van Den Berg, "Light echoes image the human body," OLE, Oct. 2001, p. 35-37.

(Continued)

*Primary Examiner* — Carl H Layno
*Assistant Examiner* — Erin Piateski
(74) *Attorney, Agent, or Firm* — Kacvinsky Daisak Bluni PLLC

(57) ABSTRACT

Systems for nerve modulation and methods for making and using the same are disclosed. An example system for nerve modulation may include a first elongate element having a distal end and a proximal end and having a helical guide having a proximal end and a distal end. The system may also include a second elongate element having a distal end and a proximal end and having a nerve modulation element proximate the distal end. A sheath may be disposed about both the first and second elongate elements. Pulling proximally on the proximal end of the first elongate element may cause simultaneous radial and longitudinal displacement of the nerve modulation element.

14 Claims, 27 Drawing Sheets

(56) References Cited

U.S. PATENT DOCUMENTS

| | | | |
|---|---|---|---|
| 3,540,431 | A | 11/1970 | Mobin |
| 3,760,812 | A * | 9/1973 | Timm et al. .................. 607/116 |
| 3,952,747 | A | 4/1976 | Kimmell |
| 3,996,938 | A | 12/1976 | Clark, III |
| 4,046,150 | A | 9/1977 | Schwartz et al. |
| 4,290,427 | A | 9/1981 | Chin |
| 4,402,686 | A | 9/1983 | Medel |
| 4,483,341 | A | 11/1984 | Wittleles |
| 4,574,804 | A | 3/1986 | Kurwa |
| 4,587,975 | A | 5/1986 | Salo et al. |
| 4,649,936 | A | 3/1987 | Ungar et al. |
| 4,682,596 | A | 7/1987 | Bales et al. |
| 4,709,698 | A | 12/1987 | Johnston et al. |
| 4,765,331 | A | 8/1988 | Petruzzi et al. |
| 4,770,653 | A | 9/1988 | Shturman |
| 4,784,132 | A | 11/1988 | Fox et al. |
| 4,784,162 | A | 11/1988 | Ricks et al. |
| 4,785,806 | A | 11/1988 | Deckelbaum et al. |
| 4,788,975 | A | 12/1988 | Shturman Leonid-Jensen et al. |
| 4,790,310 | A | 12/1988 | Ginsburg et al. |
| 4,799,479 | A | 1/1989 | Spears |
| 4,823,791 | A | 4/1989 | D'Amelio et al. |
| 4,830,003 | A | 5/1989 | Wolff et al. |
| 4,849,484 | A | 7/1989 | Heard |
| 4,862,886 | A | 9/1989 | Clarke et al. |
| 4,887,605 | A | 12/1989 | Angelsen et al. |
| 4,920,979 | A | 5/1990 | Bullara et al. |
| 4,938,766 | A | 7/1990 | Jarvik |
| 4,955,377 | A | 9/1990 | Lennox et al. |
| 4,976,711 | A | 12/1990 | Parins et al. |
| 5,034,010 | A | 7/1991 | Kittrell et al. |
| 5,052,402 | A | 10/1991 | Bencini et al. |
| 5,053,033 | A | 10/1991 | Clarke et al. |
| 5,071,424 | A | 12/1991 | Reger et al. |
| 5,074,871 | A | 12/1991 | Groshong et al. |
| 5,098,429 | A | 3/1992 | Sterzer et al. |
| 5,098,431 | A | 3/1992 | Rydell |
| 5,109,859 | A | 5/1992 | Jenkins |
| 5,125,928 | A | 6/1992 | Parins et al. |
| 5,129,396 | A | 7/1992 | Rosen et al. |
| 5,139,496 | A | 8/1992 | Hed |
| 5,143,836 | A | 9/1992 | Hartman et al. |
| 5,156,610 | A | 10/1992 | Reger et al. |
| 5,158,564 | A | 10/1992 | Schnepp-Pesch |
| 5,170,802 | A | 12/1992 | Mehra |
| 5,178,620 | A | 1/1993 | Eggers et al. |
| 5,178,625 | A | 1/1993 | Groshong et al. |
| 5,190,540 | A | 3/1993 | Lee |
| 5,211,651 | A | 5/1993 | Reger et al. |
| 5,234,407 | A | 8/1993 | Teirstein et al. |
| 5,242,441 | A | 9/1993 | Avitall |
| 5,251,634 | A | 10/1993 | Weinberg |
| 5,255,679 | A | 10/1993 | Imran |
| 5,259,395 | A * | 11/1993 | Li .................. 607/131 |
| 5,263,493 | A | 11/1993 | Avitall |
| 5,267,954 | A | 12/1993 | Nita et al. |
| 5,277,201 | A | 1/1994 | Stern et al. |
| 5,282,484 | A | 2/1994 | Reger et al. |
| 5,286,254 | A | 2/1994 | Shapland et al. |
| 5,295,484 | A | 3/1994 | Marcus |
| 5,297,564 | A | 3/1994 | Love et al. |
| 5,300,068 | A | 4/1994 | Rosar et al. |
| 5,301,683 | A | 4/1994 | Durkan |
| 5,304,115 | A | 4/1994 | Pflueger et al. |
| 5,304,121 | A | 4/1994 | Sahatjian |
| 5,304,171 | A | 4/1994 | Gregory et al. |
| 5,304,173 | A | 4/1994 | Kittrell et al. |
| 5,306,250 | A | 4/1994 | March et al. |
| 5,312,328 | A | 5/1994 | Nita et al. |
| 5,314,466 | A | 5/1994 | Stern et al. |
| 5,322,064 | A | 6/1994 | Lundquist |
| 5,324,255 | A | 6/1994 | Passafaro et al. |
| 5,326,341 | A | 7/1994 | Lew et al. |
| 5,326,342 | A | 7/1994 | Pflueger et al. |
| 5,330,518 | A | 7/1994 | Neilson et al. |
| 5,333,614 | A | 8/1994 | Feiring |
| 5,342,292 | A | 8/1994 | Nita et al. |
| 5,344,395 | A | 9/1994 | Whalen et al. |
| 5,364,392 | A | 11/1994 | Warner et al. |
| 5,365,172 | A | 11/1994 | Hrovat et al. |
| 5,368,557 | A | 11/1994 | Nita et al. |
| 5,368,558 | A | 11/1994 | Nita et al. |
| 5,380,274 | A | 1/1995 | Nita et al. |
| 5,380,319 | A | 1/1995 | Saito et al. |
| 5,382,228 | A | 1/1995 | Nita et al. |
| 5,383,874 | A | 1/1995 | Jackson et al. |
| 5,383,917 | A | 1/1995 | Desai et al. |
| 5,397,301 | A | 3/1995 | Pflueger et al. |
| 5,397,339 | A | 3/1995 | Desai |
| 5,401,272 | A | 3/1995 | Perkins et al. |
| 5,403,311 | A | 4/1995 | Abele et al. |
| 5,405,318 | A | 4/1995 | Nita et al. |
| 5,405,346 | A | 4/1995 | Grundy et al. |
| 5,409,000 | A | 4/1995 | Imran |
| 5,417,672 | A | 5/1995 | Nita et al. |
| 5,419,767 | A | 5/1995 | Eggers et al. |
| 5,427,118 | A | 6/1995 | Nita et al. |
| 5,432,876 | A | 7/1995 | Appeldorn et al. |
| 5,441,498 | A | 8/1995 | Perkins et al. |
| 5,447,509 | A | 9/1995 | Mills et al. |
| 5,451,207 | A | 9/1995 | Yock et al. |
| 5,453,091 | A | 9/1995 | Taylor et al. |
| 5,454,788 | A | 10/1995 | Walker et al. |
| 5,454,809 | A | 10/1995 | Janssen |
| 5,455,029 | A | 10/1995 | Hartman et al. |
| 5,456,682 | A | 10/1995 | Edwards et al. |
| 5,457,042 | A | 10/1995 | Hartman et al. |
| 5,471,982 | A | 12/1995 | Edwards et al. |
| 5,474,530 | A | 12/1995 | Passafaro et al. |
| 5,478,351 | A | 12/1995 | Meade et al. |
| 5,496,311 | A | 3/1996 | Abele et al. |
| 5,496,312 | A | 3/1996 | Klicek et al. |
| 5,498,261 | A | 3/1996 | Strul |
| 5,505,201 | A | 4/1996 | Grill et al. |
| 5,505,730 | A | 4/1996 | Edwards |
| 5,507,743 | A * | 4/1996 | Edwards et al. .................. 606/41 |
| 5,507,744 | A | 4/1996 | Tay et al. |
| 5,522,873 | A | 6/1996 | Jackman et al. |
| 5,531,520 | A | 7/1996 | Grimson et al. |
| 5,540,656 | A | 7/1996 | Pflueger et al. |
| 5,540,679 | A | 7/1996 | Fram et al. |
| 5,540,681 | A | 7/1996 | Strul et al. |
| 5,542,917 | A | 8/1996 | Nita et al. |
| 5,545,161 | A | 8/1996 | Imran |
| 5,562,100 | A | 10/1996 | Kittrell et al. |
| 5,571,122 | A | 11/1996 | Kelly et al. |
| 5,571,151 | A | 11/1996 | Gregory |
| 5,573,531 | A | 11/1996 | Gregory et al. |
| 5,573,533 | A | 11/1996 | Strul |
| 5,584,831 | A | 12/1996 | McKay |
| 5,584,872 | A | 12/1996 | Lafontaine et al. |
| 5,588,962 | A | 12/1996 | Nicholas et al. |
| 5,599,346 | A | 2/1997 | Edwards et al. |
| 5,601,526 | A | 2/1997 | Chapelon et al. |
| 5,609,606 | A | 3/1997 | O'Boyle et al. |
| 5,626,576 | A | 5/1997 | Janssen |
| 5,630,837 | A | 5/1997 | Crowley |
| 5,637,090 | A | 6/1997 | McGee et al. |
| 5,643,255 | A | 7/1997 | Organ |
| 5,643,297 | A | 7/1997 | Nordgren et al. |
| 5,647,847 | A | 7/1997 | Lafontaine et al. |
| 5,649,923 | A | 7/1997 | Gregory et al. |
| 5,651,780 | A | 7/1997 | Jackson et al. |
| 5,653,684 | A | 8/1997 | Laptewicz et al. |
| 5,662,671 | A | 9/1997 | Barbut et al. |
| 5,665,062 | A | 9/1997 | Houser |
| 5,665,098 | A | 9/1997 | Kelly et al. |
| 5,666,964 | A | 9/1997 | Meilus |
| 5,667,490 | A | 9/1997 | Keith et al. |
| 5,672,174 | A | 9/1997 | Gough et al. |
| 5,676,693 | A | 10/1997 | Lafontaine |
| 5,678,296 | A | 10/1997 | Fleischhacker et al. |
| 5,681,282 | A | 10/1997 | Eggers et al. |
| RE35,656 | E | 11/1997 | Feinberg |

(56) References Cited

U.S. PATENT DOCUMENTS

| | | |
|---|---|---|
| 5,688,266 A | 11/1997 | Edwards et al. |
| 5,693,015 A | 12/1997 | Walker et al. |
| 5,693,029 A | 12/1997 | Leonhardt et al. |
| 5,693,043 A | 12/1997 | Kittrell et al. |
| 5,693,082 A | 12/1997 | Warner et al. |
| 5,695,504 A | 12/1997 | Gifford et al. |
| 5,697,369 A | 12/1997 | Long, Jr. et al. |
| 5,697,909 A | 12/1997 | Eggers et al. |
| 5,702,386 A | 12/1997 | Stern et al. |
| 5,702,433 A | 12/1997 | Taylor et al. |
| 5,706,809 A | 1/1998 | Littmann et al. |
| 5,713,942 A | 2/1998 | Stern et al. |
| 5,715,819 A | 2/1998 | Svenson et al. |
| 5,735,846 A | 4/1998 | Panescu et al. |
| 5,741,214 A | 4/1998 | Ouchi et al. |
| 5,741,248 A | 4/1998 | Stern et al. |
| 5,741,249 A | 4/1998 | Moss et al. |
| 5,743,903 A | 4/1998 | Stern et al. |
| 5,748,347 A | 5/1998 | Erickson |
| 5,749,914 A | 5/1998 | Janssen |
| 5,755,682 A | 5/1998 | Knudson et al. |
| 5,755,715 A | 5/1998 | Stern et al. |
| 5,755,753 A | 5/1998 | Knowlton et al. |
| 5,769,847 A | 6/1998 | Panescu et al. |
| 5,769,880 A | 6/1998 | Truckai et al. |
| 5,772,590 A | 6/1998 | Webster, Jr. |
| 5,775,338 A | 7/1998 | Hastings |
| 5,776,174 A | 7/1998 | Van Tassel |
| 5,779,698 A | 7/1998 | Clayman et al. |
| 5,782,760 A | 7/1998 | Schaer |
| 5,785,702 A | 7/1998 | Murphy et al. |
| 5,797,849 A | 8/1998 | Vesely et al. |
| 5,797,903 A | 8/1998 | Swanson et al. |
| 5,797,952 A * | 8/1998 | Klein ........................ 623/1.12 |
| 5,800,484 A | 9/1998 | Gough et al. |
| 5,800,494 A | 9/1998 | Campbell et al. |
| 5,810,802 A | 9/1998 | Panescu et al. |
| 5,810,803 A | 9/1998 | Moss et al. |
| 5,810,810 A | 9/1998 | Tay et al. |
| 5,817,092 A | 10/1998 | Behl |
| 5,817,113 A | 10/1998 | Gifford et al. |
| 5,817,144 A | 10/1998 | Gregory et al. |
| 5,823,956 A | 10/1998 | Roth et al. |
| 5,827,203 A | 10/1998 | Nita et al. |
| 5,827,268 A | 10/1998 | Laufer |
| 5,829,447 A | 11/1998 | Stevens et al. |
| 5,830,213 A | 11/1998 | Panescu et al. |
| 5,830,222 A | 11/1998 | Makower |
| 5,832,228 A | 11/1998 | Holden et al. |
| 5,833,593 A | 11/1998 | Liprie |
| 5,836,874 A | 11/1998 | Swanson et al. |
| 5,840,076 A | 11/1998 | Swanson et al. |
| 5,843,016 A | 12/1998 | Lugnani et al. |
| 5,846,238 A | 12/1998 | Jackson et al. |
| 5,846,239 A | 12/1998 | Swanson et al. |
| 5,846,245 A | 12/1998 | McCarthy et al. |
| 5,848,969 A | 12/1998 | Panescu et al. |
| 5,853,411 A | 12/1998 | Whayne et al. |
| 5,855,614 A | 1/1999 | Stevens et al. |
| 5,860,974 A | 1/1999 | Abele |
| 5,865,801 A | 2/1999 | Houser |
| 5,868,735 A | 2/1999 | Lafontaine et al. |
| 5,868,736 A | 2/1999 | Swanson et al. |
| 5,871,483 A | 2/1999 | Jackson et al. |
| 5,871,524 A | 2/1999 | Knowlton et al. |
| 5,875,782 A | 3/1999 | Ferrari et al. |
| 5,876,369 A | 3/1999 | Houser |
| 5,876,374 A | 3/1999 | Alba et al. |
| 5,876,397 A | 3/1999 | Edelman et al. |
| 5,879,348 A | 3/1999 | Owens et al. |
| 5,891,114 A | 4/1999 | Chien et al. |
| 5,891,135 A | 4/1999 | Jackson et al. |
| 5,891,136 A | 4/1999 | McGee et al. |
| 5,891,138 A | 4/1999 | Tu et al. |
| 5,895,378 A | 4/1999 | Nita |
| 5,897,552 A | 4/1999 | Edwards et al. |
| 5,902,328 A | 5/1999 | Lafontaine et al. |
| 5,904,651 A | 5/1999 | Swanson et al. |
| 5,904,667 A | 5/1999 | Falwell et al. |
| 5,904,697 A | 5/1999 | Gifford et al. |
| 5,904,709 A | 5/1999 | Arndt et al. |
| 5,906,614 A | 5/1999 | Stern et al. |
| 5,906,623 A | 5/1999 | Peterson |
| 5,906,636 A | 5/1999 | Casscells et al. |
| 5,916,192 A | 6/1999 | Nita et al. |
| 5,916,227 A | 6/1999 | Keith et al. |
| 5,916,239 A | 6/1999 | Geddes et al. |
| 5,919,219 A | 7/1999 | Knowlton et al. |
| 5,924,424 A | 7/1999 | Stevens et al. |
| 5,925,038 A | 7/1999 | Panescu et al. |
| 5,934,284 A | 8/1999 | Plaia et al. |
| 5,935,063 A | 8/1999 | Nguyen |
| 5,935,159 A * | 8/1999 | Cross et al. ................... 607/116 |
| 5,938,670 A | 8/1999 | Keith et al. |
| 5,947,977 A | 9/1999 | Slepian |
| 5,948,011 A | 9/1999 | Knowlton et al. |
| 5,951,494 A | 9/1999 | Wang et al. |
| 5,951,539 A | 9/1999 | Nita et al. |
| 5,954,717 A | 9/1999 | Behl et al. |
| 5,957,882 A | 9/1999 | Nita et al. |
| 5,957,941 A | 9/1999 | Ream et al. |
| 5,957,969 A | 9/1999 | Warner et al. |
| 5,961,513 A | 10/1999 | Swanson et al. |
| 5,964,757 A | 10/1999 | Ponzi et al. |
| 5,967,976 A | 10/1999 | Larsen et al. |
| 5,967,978 A | 10/1999 | Littmann et al. |
| 5,967,984 A | 10/1999 | Chu et al. |
| 5,971,975 A | 10/1999 | Mills et al. |
| 5,972,026 A | 10/1999 | Laufer et al. |
| 5,980,563 A | 11/1999 | Tu et al. |
| 5,989,208 A | 11/1999 | Nita et al. |
| 5,989,284 A | 11/1999 | Laufer |
| 5,993,462 A | 11/1999 | Pomeranz et al. |
| 5,997,497 A | 12/1999 | Nita et al. |
| 5,999,678 A | 12/1999 | Murphy et al. |
| 6,004,269 A | 12/1999 | Crowley et al. |
| 6,004,316 A | 12/1999 | Laufer |
| 6,007,514 A | 12/1999 | Nita |
| 6,010,522 A | 1/2000 | Barbut et al. |
| 6,013,033 A | 1/2000 | Berger et al. |
| 6,014,590 A | 1/2000 | Whayne et al. |
| 6,022,309 A | 2/2000 | Celliers et al. |
| 6,024,740 A | 2/2000 | Lesh et al. |
| 6,030,611 A | 2/2000 | Gorecki et al. |
| 6,032,675 A | 3/2000 | Rubinsky et al. |
| 6,033,397 A | 3/2000 | Laufer et al. |
| 6,033,398 A | 3/2000 | Farley et al. |
| 6,036,687 A | 3/2000 | Laufer et al. |
| 6,036,689 A | 3/2000 | Tu et al. |
| 6,041,260 A | 3/2000 | Stern et al. |
| 6,050,994 A | 4/2000 | Sherman et al. |
| 6,056,744 A | 5/2000 | Edwards |
| 6,056,746 A | 5/2000 | Goble et al. |
| 6,063,085 A | 5/2000 | Tay et al. |
| 6,066,096 A | 5/2000 | Smith et al. |
| 6,066,139 A | 5/2000 | Ryan et al. |
| 6,068,638 A | 5/2000 | Makower |
| 6,068,653 A | 5/2000 | Lafontaine |
| 6,071,277 A | 6/2000 | Farley et al. |
| 6,071,278 A | 6/2000 | Panescu et al. |
| 6,078,839 A | 6/2000 | Carson |
| 6,079,414 A | 6/2000 | Roth |
| 6,080,171 A | 6/2000 | Keith et al. |
| 6,081,749 A | 6/2000 | Ingle et al. |
| 6,086,581 A | 7/2000 | Reynolds et al. |
| 6,093,166 A | 7/2000 | Knudson et al. |
| 6,096,021 A | 8/2000 | Helm et al. |
| 6,099,526 A | 8/2000 | Whayne et al. |
| 6,102,908 A | 8/2000 | Tu et al. |
| 6,106,477 A | 8/2000 | Miesel et al. |
| 6,110,187 A | 8/2000 | Donlon et al. |
| 6,114,311 A | 9/2000 | Parmacek et al. |
| 6,117,101 A | 9/2000 | Diederich et al. |
| 6,117,128 A | 9/2000 | Gregory |

(56) References Cited

U.S. PATENT DOCUMENTS

| | | | |
|---|---|---|---|
| 6,120,476 | A | 9/2000 | Fung et al. |
| 6,120,516 | A | 9/2000 | Selmon et al. |
| 6,121,775 | A | 9/2000 | Pearlman |
| 6,123,679 | A | 9/2000 | Lafaut et al. |
| 6,123,682 | A | 9/2000 | Knudson et al. |
| 6,123,702 | A | 9/2000 | Swanson et al. |
| 6,123,703 | A | 9/2000 | Tu et al. |
| 6,123,718 | A | 9/2000 | Tu et al. |
| 6,129,725 | A | 10/2000 | Tu et al. |
| 6,135,997 | A | 10/2000 | Laufer et al. |
| 6,142,991 | A | 11/2000 | Schatzberger et al. |
| 6,142,993 | A | 11/2000 | Whayne et al. |
| 6,149,647 | A | 11/2000 | Tu et al. |
| 6,152,899 | A | 11/2000 | Farley et al. |
| 6,152,912 | A | 11/2000 | Jansen et al. |
| 6,156,046 | A | 12/2000 | Passafaro et al. |
| 6,158,250 | A | 12/2000 | Tibbals et al. |
| 6,159,187 | A | 12/2000 | Park et al. |
| 6,159,225 | A | 12/2000 | Makower |
| 6,161,048 | A | 12/2000 | Sluijter et al. |
| 6,162,184 | A | 12/2000 | Swanson et al. |
| 6,165,163 | A | 12/2000 | Chien et al. |
| 6,165,172 | A | 12/2000 | Farley et al. |
| 6,165,187 | A | 12/2000 | Reger et al. |
| 6,168,594 | B1 | 1/2001 | Lafontaine et al. |
| 6,171,321 | B1 | 1/2001 | Gifford, III et al. |
| 6,179,832 | B1 | 1/2001 | Jones et al. |
| 6,179,835 | B1 | 1/2001 | Panescu et al. |
| 6,179,858 | B1 | 1/2001 | Squire et al. |
| 6,179,859 | B1 | 1/2001 | Bates et al. |
| 6,183,468 | B1 | 2/2001 | Swanson et al. |
| 6,183,486 | B1 | 2/2001 | Snow et al. |
| 6,190,379 | B1 | 2/2001 | Heuser et al. |
| 6,191,862 | B1 | 2/2001 | Swanson et al. |
| 6,197,021 | B1 | 3/2001 | Panescu et al. |
| 6,200,266 | B1 | 3/2001 | Shokrollahi et al. |
| 6,203,537 | B1 | 3/2001 | Adrian |
| 6,203,561 | B1 | 3/2001 | Ramee et al. |
| 6,210,406 | B1 | 4/2001 | Webster |
| 6,211,247 | B1 | 4/2001 | Goodman |
| 6,217,576 | B1 | 4/2001 | Tu et al. |
| 6,219,577 | B1 | 4/2001 | Brown, III et al. |
| 6,228,076 | B1 | 5/2001 | Winston et al. |
| 6,228,109 | B1 | 5/2001 | Tu et al. |
| 6,231,516 | B1 | 5/2001 | Keilman et al. |
| 6,231,587 | B1 | 5/2001 | Makower |
| 6,235,044 | B1 | 5/2001 | Root et al. |
| 6,236,883 | B1 | 5/2001 | Ciaccio et al. |
| 6,237,605 | B1 | 5/2001 | Vaska et al. |
| 6,238,389 | B1 | 5/2001 | Paddock et al. |
| 6,238,392 | B1 | 5/2001 | Long |
| 6,241,666 | B1 | 6/2001 | Pomeranz et al. |
| 6,241,753 | B1 | 6/2001 | Knowlton |
| 6,245,020 | B1 | 6/2001 | Moore et al. |
| 6,245,045 | B1 | 6/2001 | Stratienko |
| 6,248,126 | B1 | 6/2001 | Lesser et al. |
| 6,251,128 | B1 | 6/2001 | Knopp et al. |
| 6,258,087 | B1 | 7/2001 | Edwards et al. |
| 6,273,886 | B1 | 8/2001 | Edwards et al. |
| 6,280,466 | B1 | 8/2001 | Kugler et al. |
| 6,283,935 | B1 | 9/2001 | Laufer et al. |
| 6,283,959 | B1 | 9/2001 | LaLonde |
| 6,284,743 | B1 | 9/2001 | Parmacek et al. |
| 6,287,323 | B1 | 9/2001 | Hammerslag |
| 6,290,696 | B1 | 9/2001 | Lafontaine |
| 6,292,695 | B1 | 9/2001 | Webster, Jr. et al. |
| 6,293,942 | B1 | 9/2001 | Goble et al. |
| 6,293,943 | B1 | 9/2001 | Panescu et al. |
| 6,296,619 | B1 | 10/2001 | Brisken et al. |
| 6,298,256 | B1 | 10/2001 | Meyer |
| 6,299,379 | B1 | 10/2001 | Lewis |
| 6,299,623 | B1 | 10/2001 | Wulfman |
| 6,309,379 | B1 | 10/2001 | Willard et al. |
| 6,309,399 | B1 | 10/2001 | Barbut et al. |
| 6,311,090 | B1 | 10/2001 | Knowlton |
| 6,317,615 | B1 | 11/2001 | KenKnight et al. |
| 6,319,242 | B1 | 11/2001 | Patterson et al. |
| 6,319,251 | B1 | 11/2001 | Tu et al. |
| 6,322,559 | B1 | 11/2001 | Daulton et al. |
| 6,324,433 | B1 | 11/2001 | Errico |
| 6,325,797 | B1 | 12/2001 | Stewart et al. |
| 6,325,799 | B1 | 12/2001 | Goble |
| 6,328,699 | B1 | 12/2001 | Eigler et al. |
| 6,346,074 | B1 | 2/2002 | Roth |
| 6,346,104 | B2 | 2/2002 | Daly et al. |
| 6,350,248 | B1 | 2/2002 | Knudson et al. |
| 6,350,276 | B1 | 2/2002 | Knowlton |
| 6,353,751 | B1 | 3/2002 | Swanson et al. |
| 6,355,029 | B1 | 3/2002 | Joye |
| 6,357,447 | B1 | 3/2002 | Swanson et al. |
| 6,361,519 | B1 | 3/2002 | Knudson et al. |
| 6,364,840 | B1 | 4/2002 | Crowley |
| 6,371,965 | B2 | 4/2002 | Gifford, III et al. |
| 6,375,668 | B1 | 4/2002 | Gifford et al. |
| 6,377,854 | B1 | 4/2002 | Knowlton |
| 6,377,855 | B1 | 4/2002 | Knowlton |
| 6,379,352 | B1 | 4/2002 | Reynolds et al. |
| 6,379,373 | B1 | 4/2002 | Sawhney et al. |
| 6,381,497 | B1 | 4/2002 | Knowlton |
| 6,381,498 | B1 | 4/2002 | Knowlton |
| 6,383,151 | B1 | 5/2002 | Diederich et al. |
| 6,387,105 | B1 | 5/2002 | Gifford, III et al. |
| 6,387,380 | B1 | 5/2002 | Knowlton |
| 6,389,311 | B1 | 5/2002 | Whayne et al. |
| 6,389,314 | B2 | 5/2002 | Feiring |
| 6,391,024 | B1 | 5/2002 | Sun et al. |
| 6,394,096 | B1 | 5/2002 | Constantz |
| 6,394,956 | B1 | 5/2002 | Chandrasekaran et al. |
| 6,398,780 | B1 | 6/2002 | Farley et al. |
| 6,398,782 | B1 | 6/2002 | Pecor et al. |
| 6,398,792 | B1 | 6/2002 | O'Connor |
| 6,401,720 | B1 | 6/2002 | Stevens et al. |
| 6,402,719 | B1 | 6/2002 | Ponzi et al. |
| 6,405,090 | B1 | 6/2002 | Knowlton |
| 6,409,723 | B1 | 6/2002 | Edwards |
| 6,413,255 | B1 | 7/2002 | Stern |
| 6,421,559 | B1 | 7/2002 | Pearlman |
| 6,423,057 | B1 | 7/2002 | He et al. |
| 6,425,867 | B1 | 7/2002 | Vaezy et al. |
| 6,425,912 | B1 | 7/2002 | Knowlton |
| 6,427,118 | B1 | 7/2002 | Suzuki |
| 6,428,534 | B1 | 8/2002 | Joye et al. |
| 6,428,536 | B2 | 8/2002 | Panescu et al. |
| 6,430,446 | B1 | 8/2002 | Knowlton |
| 6,432,102 | B2 | 8/2002 | Joye et al. |
| 6,436,056 | B1 | 8/2002 | Wang et al. |
| 6,438,424 | B1 | 8/2002 | Knowlton |
| 6,440,125 | B1 | 8/2002 | Rentrop |
| 6,442,413 | B1 | 8/2002 | Silver |
| 6,443,965 | B1 | 9/2002 | Gifford, III et al. |
| 6,445,939 | B1 | 9/2002 | Swanson et al. |
| 6,447,505 | B2 | 9/2002 | McGovern et al. |
| 6,447,509 | B1 | 9/2002 | Bonnet et al. |
| 6,451,034 | B1 | 9/2002 | Gifford, III et al. |
| 6,451,044 | B1 | 9/2002 | Naghavi et al. |
| 6,453,202 | B1 | 9/2002 | Knowlton |
| 6,454,737 | B1 | 9/2002 | Nita et al. |
| 6,454,757 | B1 | 9/2002 | Nita et al. |
| 6,454,775 | B1 | 9/2002 | Demarais et al. |
| 6,458,098 | B1 | 10/2002 | Kanesaka |
| 6,461,378 | B1 | 10/2002 | Knowlton |
| 6,468,276 | B1 | 10/2002 | McKay |
| 6,468,297 | B1 | 10/2002 | Williams et al. |
| 6,470,216 | B1 | 10/2002 | Knowlton |
| 6,470,219 | B1 | 10/2002 | Edwards et al. |
| 6,471,696 | B1 | 10/2002 | Berube et al. |
| 6,475,213 | B1 | 11/2002 | Whayne et al. |
| 6,475,215 | B1 | 11/2002 | Tanrisever |
| 6,475,238 | B1 | 11/2002 | Fedida et al. |
| 6,477,426 | B1 | 11/2002 | Fenn et al. |
| 6,480,745 | B2 | 11/2002 | Nelson et al. |
| 6,481,704 | B1 | 11/2002 | Koster et al. |
| 6,482,202 | B1 | 11/2002 | Goble et al. |
| 6,484,052 | B1 | 11/2002 | Visuri et al. |

(56) References Cited

U.S. PATENT DOCUMENTS

| | | |
|---|---|---|
| 6,485,489 B2 | 11/2002 | Teirstein et al. |
| 6,488,679 B1 | 12/2002 | Swanson et al. |
| 6,489,307 B1 | 12/2002 | Phillips et al. |
| 6,491,705 B2 | 12/2002 | Gifford, III et al. |
| 6,494,891 B1 | 12/2002 | Cornish et al. |
| 6,497,711 B1 | 12/2002 | Plaia et al. |
| 6,500,172 B1 | 12/2002 | Panescu et al. |
| 6,500,174 B1 | 12/2002 | Maguire et al. |
| 6,508,765 B2 | 1/2003 | Suorsa et al. |
| 6,508,804 B2 | 1/2003 | Sarge et al. |
| 6,508,815 B1 | 1/2003 | Strul et al. |
| 6,511,478 B1 | 1/2003 | Burnside et al. |
| 6,511,496 B1 | 1/2003 | Huter et al. |
| 6,511,500 B1 | 1/2003 | Rahme |
| 6,514,236 B1 | 2/2003 | Stratienko |
| 6,514,245 B1 | 2/2003 | Williams et al. |
| 6,514,248 B1 | 2/2003 | Eggers et al. |
| 6,517,534 B1 | 2/2003 | McGovern et al. |
| 6,517,572 B2 | 2/2003 | Kugler et al. |
| 6,522,913 B2 | 2/2003 | Swanson et al. |
| 6,522,926 B1 | 2/2003 | Kieval et al. |
| 6,524,299 B1 | 2/2003 | Tran et al. |
| 6,527,765 B2 | 3/2003 | Kelman et al. |
| 6,527,769 B2 | 3/2003 | Langberg et al. |
| 6,540,761 B2 | 4/2003 | Houser |
| 6,542,781 B1 | 4/2003 | Koblish et al. |
| 6,544,780 B1 | 4/2003 | Wang |
| 6,546,272 B1 | 4/2003 | MacKinnon et al. |
| 6,547,788 B1 | 4/2003 | Maguire et al. |
| 6,549,800 B1 | 4/2003 | Atalar et al. |
| 6,552,796 B2 | 4/2003 | Magnin et al. |
| 6,554,780 B1 | 4/2003 | Sampson et al. |
| 6,558,381 B2 | 5/2003 | Ingle et al. |
| 6,558,382 B2 | 5/2003 | Jahns et al. |
| 6,564,096 B2 | 5/2003 | Mest |
| 6,565,582 B2 | 5/2003 | Gifford, III et al. |
| 6,569,109 B2 | 5/2003 | Sakurai et al. |
| 6,569,177 B1 | 5/2003 | Dillard et al. |
| 6,570,659 B2 | 5/2003 | Schmitt |
| 6,572,551 B1 | 6/2003 | Smith et al. |
| 6,572,612 B2 | 6/2003 | Stewart et al. |
| 6,577,902 B1 | 6/2003 | Laufer et al. |
| 6,579,308 B1 | 6/2003 | Jansen et al. |
| 6,579,311 B1 | 6/2003 | Makower |
| 6,582,423 B1 | 6/2003 | Thapliyal et al. |
| 6,589,238 B2 | 7/2003 | Edwards et al. |
| 6,592,526 B1 | 7/2003 | Lenker |
| 6,592,567 B1 | 7/2003 | Levin et al. |
| 6,595,959 B1 | 7/2003 | Stratienko |
| 6,600,956 B2 | 7/2003 | Maschino et al. |
| 6,602,242 B1 | 8/2003 | Fung et al. |
| 6,602,246 B1 | 8/2003 | Joye et al. |
| 6,605,084 B2 | 8/2003 | Acker et al. |
| 6,623,452 B2 | 9/2003 | Chien et al. |
| 6,623,453 B1 | 9/2003 | Guibert et al. |
| 6,632,193 B1 | 10/2003 | Davison et al. |
| 6,632,196 B1 | 10/2003 | Houser |
| 6,645,223 B2 | 11/2003 | Boyle et al. |
| 6,648,854 B1 | 11/2003 | Patterson et al. |
| 6,648,878 B2 | 11/2003 | Lafontaine |
| 6,648,879 B2 | 11/2003 | Joye et al. |
| 6,651,672 B2 | 11/2003 | Roth |
| 6,652,513 B2 | 11/2003 | Panescu et al. |
| 6,652,515 B1 | 11/2003 | Maguire et al. |
| 6,656,136 B1 | 12/2003 | Weng et al. |
| 6,658,279 B2 | 12/2003 | Swanson et al. |
| 6,659,981 B2 | 12/2003 | Stewart et al. |
| 6,666,858 B2 | 12/2003 | Lafontaine |
| 6,666,863 B2 | 12/2003 | Wentzel et al. |
| 6,669,655 B1 | 12/2003 | Acker et al. |
| 6,669,692 B1 | 12/2003 | Nelson et al. |
| 6,673,040 B1 | 1/2004 | Samson et al. |
| 6,673,064 B1 | 1/2004 | Rentrop |
| 6,673,066 B2 | 1/2004 | Werneth |
| 6,673,090 B2 | 1/2004 | Root et al. |
| 6,673,101 B1 | 1/2004 | Fitzgerald et al. |
| 6,673,290 B1 | 1/2004 | Whayne et al. |
| 6,676,678 B2 | 1/2004 | Gifford, III et al. |
| 6,679,268 B2 | 1/2004 | Stevens et al. |
| 6,681,773 B2 | 1/2004 | Murphy et al. |
| 6,682,541 B1 | 1/2004 | Gifford, III et al. |
| 6,684,098 B2 | 1/2004 | Oshio et al. |
| 6,685,732 B2 | 2/2004 | Kramer |
| 6,685,733 B1 | 2/2004 | Dae et al. |
| 6,689,086 B1 | 2/2004 | Nita et al. |
| 6,689,148 B2 | 2/2004 | Sawhney et al. |
| 6,690,181 B1 | 2/2004 | Dowdeswell et al. |
| 6,692,490 B1 | 2/2004 | Edwards |
| 6,695,830 B2 | 2/2004 | Vigil et al. |
| 6,695,857 B2 | 2/2004 | Gifford, III et al. |
| 6,699,241 B2 | 3/2004 | Rappaport et al. |
| 6,699,257 B2 | 3/2004 | Gifford, III et al. |
| 6,702,748 B1 | 3/2004 | Nita et al. |
| 6,702,811 B2 | 3/2004 | Stewart et al. |
| 6,706,010 B1 | 3/2004 | Miki et al. |
| 6,706,011 B1 | 3/2004 | Murphy-Chutorian et al. |
| 6,706,037 B2 | 3/2004 | Zvuloni et al. |
| 6,709,431 B2 | 3/2004 | Lafontaine |
| 6,711,429 B1 | 3/2004 | Gilboa et al. |
| 6,712,815 B2 | 3/2004 | Sampson et al. |
| 6,714,822 B2 | 3/2004 | King et al. |
| 6,716,184 B2 | 4/2004 | Vaezy et al. |
| 6,720,350 B2 | 4/2004 | Kunz et al. |
| 6,723,043 B2 | 4/2004 | Kleeman et al. |
| 6,723,064 B2 | 4/2004 | Babaev |
| 6,736,811 B2 | 5/2004 | Panescu et al. |
| 6,743,184 B2 | 6/2004 | Sampson et al. |
| 6,746,401 B2 | 6/2004 | Panescu |
| 6,746,464 B1 | 6/2004 | Makower |
| 6,746,474 B2 | 6/2004 | Saadat |
| 6,748,953 B2 | 6/2004 | Sherry et al. |
| 6,749,607 B2 | 6/2004 | Edwards et al. |
| 6,752,805 B2 | 6/2004 | Maguire et al. |
| 6,760,616 B2 | 7/2004 | Hoey et al. |
| 6,763,261 B2 | 7/2004 | Casscells, III et al. |
| 6,764,501 B2 | 7/2004 | Ganz |
| 6,769,433 B2 | 8/2004 | Zikorus et al. |
| 6,770,070 B1 | 8/2004 | Balbierz |
| 6,771,996 B2 | 8/2004 | Bowe et al. |
| 6,773,433 B2 | 8/2004 | Stewart et al. |
| 6,786,900 B2 | 9/2004 | Joye et al. |
| 6,786,901 B2 | 9/2004 | Joye et al. |
| 6,786,904 B2 | 9/2004 | Döscher et al. |
| 6,788,977 B2 | 9/2004 | Fenn et al. |
| 6,790,206 B2 | 9/2004 | Panescu |
| 6,790,222 B2 | 9/2004 | Kugler et al. |
| 6,796,981 B2 | 9/2004 | Wham et al. |
| 6,797,933 B1 | 9/2004 | Mendis et al. |
| 6,797,960 B1 | 9/2004 | Spartiotis et al. |
| 6,800,075 B2 | 10/2004 | Mische et al. |
| 6,802,857 B1 | 10/2004 | Venugopalan |
| 6,807,444 B2 | 10/2004 | Tu et al. |
| 6,811,550 B2 | 11/2004 | Holland et al. |
| 6,813,520 B2 | 11/2004 | Truckai et al. |
| 6,814,730 B2 | 11/2004 | Li |
| 6,814,733 B2 | 11/2004 | Schwartz et al. |
| 6,823,205 B1 | 11/2004 | Jara |
| 6,824,516 B2 | 11/2004 | Batten et al. |
| 6,827,726 B2 | 12/2004 | Parodi |
| 6,827,926 B2 | 12/2004 | Robinson et al. |
| 6,829,497 B2 | 12/2004 | Mogul |
| 6,830,568 B1 | 12/2004 | Kesten et al. |
| 6,837,886 B2 | 1/2005 | Collins et al. |
| 6,837,888 B2 | 1/2005 | Ciarrocca et al. |
| 6,845,267 B2 | 1/2005 | Harrison |
| 6,847,848 B2 | 1/2005 | Sterzer |
| 6,849,073 B2 | 2/2005 | Hoey et al. |
| 6,849,075 B2 | 2/2005 | Bertolero et al. |
| 6,853,425 B2 | 2/2005 | Kim et al. |
| 6,855,123 B2 | 2/2005 | Nita |
| 6,855,143 B2 | 2/2005 | Davison et al. |
| 6,869,431 B2 | 3/2005 | Maguire et al. |
| 6,872,183 B2 | 3/2005 | Sampson et al. |
| 6,884,260 B2 | 4/2005 | Kugler et al. |

(56) References Cited

U.S. PATENT DOCUMENTS

| | | |
|---|---|---|
| 6,889,694 B2 | 5/2005 | Hooven |
| 6,893,436 B2 | 5/2005 | Woodard et al. |
| 6,895,077 B2 | 5/2005 | Karellas et al. |
| 6,895,265 B2 | 5/2005 | Silver |
| 6,898,454 B2 | 5/2005 | Atalar et al. |
| 6,899,711 B2 | 5/2005 | Stewart et al. |
| 6,899,718 B2 | 5/2005 | Gifford, III et al. |
| 6,905,494 B2 | 6/2005 | Yon et al. |
| 6,908,462 B2 | 6/2005 | Joye et al. |
| 6,909,009 B2 | 6/2005 | Koridze |
| 6,911,026 B1 | 6/2005 | Hall et al. |
| 6,915,806 B2 | 7/2005 | Pacek et al. |
| 6,923,805 B1 | 8/2005 | LaFontaine et al. |
| 6,923,808 B2 | 8/2005 | Taimisto |
| 6,926,246 B2 | 8/2005 | Ginggen |
| 6,926,713 B2 | 8/2005 | Rioux et al. |
| 6,926,716 B2 | 8/2005 | Baker et al. |
| 6,929,009 B2 | 8/2005 | Makower et al. |
| 6,929,632 B2 | 8/2005 | Nita et al. |
| 6,929,639 B2 | 8/2005 | Lafontaine |
| 6,932,776 B2 | 8/2005 | Carr |
| 6,936,047 B2 | 8/2005 | Nasab et al. |
| 6,942,620 B2 | 9/2005 | Nita et al. |
| 6,942,657 B2 | 9/2005 | Sinofsky et al. |
| 6,942,677 B2 | 9/2005 | Nita et al. |
| 6,942,692 B2 | 9/2005 | Landau et al. |
| 6,949,097 B2 | 9/2005 | Stewart et al. |
| 6,949,121 B1 | 9/2005 | Laguna |
| 6,952,615 B2 | 10/2005 | Satake |
| 6,953,425 B2 | 10/2005 | Brister |
| 6,955,174 B2 | 10/2005 | Joye et al. |
| 6,955,175 B2 | 10/2005 | Stevens et al. |
| 6,959,711 B2 | 11/2005 | Murphy et al. |
| 6,960,207 B2 | 11/2005 | Vanney et al. |
| 6,962,584 B1 | 11/2005 | Stone et al. |
| 6,964,660 B2 | 11/2005 | Maguire et al. |
| 6,966,908 B2 | 11/2005 | Maguire et al. |
| 6,972,015 B2 | 12/2005 | Joye et al. |
| 6,972,024 B1 | 12/2005 | Kilpatrick et al. |
| 6,974,456 B2 | 12/2005 | Edwards et al. |
| 6,978,174 B2 | 12/2005 | Gelfand et al. |
| 6,979,329 B2 | 12/2005 | Burnside et al. |
| 6,979,420 B2 | 12/2005 | Weber |
| 6,984,238 B2 | 1/2006 | Gifford, III et al. |
| 6,985,774 B2 | 1/2006 | Kieval et al. |
| 6,986,739 B2 | 1/2006 | Warren et al. |
| 6,989,009 B2 | 1/2006 | Lafontaine |
| 6,989,010 B2 | 1/2006 | Francischelli et al. |
| 6,991,617 B2 | 1/2006 | Hektner et al. |
| 7,001,378 B2 | 2/2006 | Yon et al. |
| 7,006,858 B2 | 2/2006 | Silver et al. |
| 7,022,105 B1 | 4/2006 | Edwards |
| 7,022,120 B2 | 4/2006 | Lafontaine |
| 7,025,767 B2 | 4/2006 | Schaefer et al. |
| 7,033,322 B2 | 4/2006 | Silver |
| 7,033,372 B1 | 4/2006 | Cahalan |
| 7,041,098 B2 | 5/2006 | Farley et al. |
| 7,050,848 B2 | 5/2006 | Hoey et al. |
| 7,063,670 B2 | 6/2006 | Sampson et al. |
| 7,063,679 B2 | 6/2006 | Maguire et al. |
| 7,063,719 B2 | 6/2006 | Jansen et al. |
| 7,066,895 B2 | 6/2006 | Podany |
| 7,066,900 B2 | 6/2006 | Botto et al. |
| 7,066,904 B2 | 6/2006 | Rosenthal et al. |
| 7,072,720 B2 | 7/2006 | Puskas |
| 7,074,217 B2 | 7/2006 | Strul et al. |
| 7,081,112 B2 | 7/2006 | Joye et al. |
| 7,081,114 B2 | 7/2006 | Rashidi |
| 7,081,115 B2 | 7/2006 | Taimisto |
| 7,083,614 B2 | 8/2006 | Fjield et al. |
| 7,084,276 B2 | 8/2006 | Vu et al. |
| 7,087,026 B2 | 8/2006 | Callister et al. |
| 7,087,051 B2 | 8/2006 | Bourne et al. |
| 7,087,052 B2 | 8/2006 | Sampson et al. |
| 7,087,053 B2 | 8/2006 | Vanney |
| 7,089,065 B2 | 8/2006 | Westlund et al. |
| 7,097,641 B1 | 8/2006 | Arless et al. |
| 7,100,614 B2 | 9/2006 | Stevens et al. |
| 7,101,368 B2 | 9/2006 | Lafontaine |
| 7,104,983 B2 | 9/2006 | Grasso, III et al. |
| 7,104,987 B2 | 9/2006 | Biggs et al. |
| 7,108,715 B2 | 9/2006 | Lawrence-Brown et al. |
| 7,112,196 B2 | 9/2006 | Brosch et al. |
| 7,112,198 B2 | 9/2006 | Satake |
| 7,112,211 B2 | 9/2006 | Gifford, III et al. |
| 7,122,019 B1 | 10/2006 | Kesten et al. |
| 7,122,033 B2 | 10/2006 | Wood |
| 7,134,438 B2 | 11/2006 | Makower et al. |
| 7,137,963 B2 | 11/2006 | Nita et al. |
| 7,137,980 B2 | 11/2006 | Buysse et al. |
| 7,153,315 B2 | 12/2006 | Miller |
| 7,155,271 B2 | 12/2006 | Halperin et al. |
| 7,157,491 B2 | 1/2007 | Mewshaw et al. |
| 7,157,492 B2 | 1/2007 | Mewshaw et al. |
| 7,158,832 B2 | 1/2007 | Kieval et al. |
| 7,160,296 B2 | 1/2007 | Pearson et al. |
| 7,162,303 B2 | 1/2007 | Levin et al. |
| 7,165,551 B2 | 1/2007 | Edwards et al. |
| 7,169,144 B2 | 1/2007 | Hoey et al. |
| 7,172,589 B2 | 2/2007 | Lafontaine |
| 7,172,610 B2 | 2/2007 | Heitzmann et al. |
| 7,181,261 B2 | 2/2007 | Silver et al. |
| 7,184,811 B2 | 2/2007 | Phan et al. |
| 7,184,827 B1 | 2/2007 | Edwards |
| 7,189,227 B2 | 3/2007 | Lafontaine |
| 7,192,427 B2 | 3/2007 | Chapelon et al. |
| 7,192,586 B2 | 3/2007 | Bander |
| 7,197,354 B2 | 3/2007 | Sobe |
| 7,198,632 B2 | 4/2007 | Lim et al. |
| 7,200,445 B1 | 4/2007 | Dalbec et al. |
| 7,201,749 B2 | 4/2007 | Govari et al. |
| 7,203,537 B2 | 4/2007 | Mower |
| 7,214,234 B2 | 5/2007 | Rapacki et al. |
| 7,220,233 B2 | 5/2007 | Nita et al. |
| 7,220,239 B2 | 5/2007 | Wilson et al. |
| 7,220,257 B1 | 5/2007 | Lafontaine |
| 7,220,270 B2 | 5/2007 | Sawhney et al. |
| 7,232,458 B2 | 6/2007 | Saadat |
| 7,232,459 B2 | 6/2007 | Greenberg et al. |
| 7,238,184 B2 | 7/2007 | Megerman et al. |
| 7,241,273 B2 | 7/2007 | Maguire et al. |
| 7,241,736 B2 | 7/2007 | Hunter et al. |
| 7,247,141 B2 | 7/2007 | Makin et al. |
| 7,250,041 B2 | 7/2007 | Chiu et al. |
| 7,250,440 B2 | 7/2007 | Mewshaw et al. |
| 7,252,664 B2 | 8/2007 | Nasab et al. |
| 7,252,679 B2 | 8/2007 | Fischell et al. |
| 7,264,619 B2 | 9/2007 | Venturelli |
| 7,279,600 B2 | 10/2007 | Mewshaw et al. |
| 7,280,863 B2 | 10/2007 | Shachar |
| 7,282,213 B2 | 10/2007 | Schroeder et al. |
| 7,285,119 B2 | 10/2007 | Stewart et al. |
| 7,285,120 B2 | 10/2007 | Im et al. |
| 7,288,089 B2 | 10/2007 | Yon et al. |
| 7,288,096 B2 | 10/2007 | Chin |
| 7,291,146 B2 | 11/2007 | Steinke et al. |
| 7,293,562 B2 | 11/2007 | Malecki et al. |
| 7,294,125 B2 | 11/2007 | Phalen et al. |
| 7,294,126 B2 | 11/2007 | Sampson et al. |
| 7,294,127 B2 | 11/2007 | Leung et al. |
| 7,297,131 B2 | 11/2007 | Nita |
| 7,297,475 B2 | 11/2007 | Koiwai et al. |
| 7,300,433 B2 | 11/2007 | Lane et al. |
| 7,301,108 B2 | 11/2007 | Egitto et al. |
| 7,310,150 B2 | 12/2007 | Guillermo et al. |
| 7,313,430 B2 | 12/2007 | Urquhart et al. |
| 7,314,483 B2 | 1/2008 | Landau et al. |
| 7,317,077 B2 | 1/2008 | Averback et al. |
| 7,323,006 B2 | 1/2008 | Andreas et al. |
| 7,326,206 B2 | 2/2008 | Paul et al. |
| 7,326,226 B2 | 2/2008 | Root et al. |
| 7,326,235 B2 | 2/2008 | Edwards |
| 7,326,237 B2 | 2/2008 | DePalma et al. |
| 7,329,236 B2 | 2/2008 | Kesten et al. |

(56) References Cited

U.S. PATENT DOCUMENTS

| | | |
|---|---|---|
| 7,335,180 B2 | 2/2008 | Nita et al. |
| 7,335,192 B2 | 2/2008 | Keren et al. |
| 7,338,467 B2 | 3/2008 | Lutter |
| 7,341,570 B2 | 3/2008 | Keren et al. |
| 7,343,195 B2 | 3/2008 | Strommer et al. |
| 7,347,857 B2 | 3/2008 | Anderson et al. |
| 7,348,003 B2 | 3/2008 | Salcedo et al. |
| 7,352,593 B2 | 4/2008 | Zeng et al. |
| 7,354,927 B2 | 4/2008 | Vu |
| 7,359,732 B2 | 4/2008 | Kim et al. |
| 7,361,341 B2 | 4/2008 | Salcedo et al. |
| 7,364,566 B2 | 4/2008 | Elkins et al. |
| 7,367,970 B2 | 5/2008 | Govari et al. |
| 7,367,975 B2 | 5/2008 | Malecki et al. |
| 7,371,231 B2 | 5/2008 | Rioux et al. |
| 7,387,126 B2 | 6/2008 | Cox et al. |
| 7,393,338 B2 | 7/2008 | Nita |
| 7,396,355 B2 | 7/2008 | Goldman et al. |
| 7,402,151 B2 | 7/2008 | Rosenman et al. |
| 7,402,312 B2 | 7/2008 | Rosen et al. |
| 7,404,824 B1 | 7/2008 | Webler et al. |
| 7,406,970 B2 | 8/2008 | Zikorus et al. |
| 7,407,502 B2 | 8/2008 | Strul et al. |
| 7,407,506 B2 | 8/2008 | Makower |
| 7,407,671 B2 | 8/2008 | McBride et al. |
| 7,408,021 B2 | 8/2008 | Averback et al. |
| 7,410,486 B2 | 8/2008 | Fuimaono et al. |
| 7,413,556 B2 | 8/2008 | Zhang et al. |
| 7,425,212 B1 | 9/2008 | Danek et al. |
| 7,426,409 B2 | 9/2008 | Casscells, III et al. |
| 7,435,246 B2 | 10/2008 | Zihlmann |
| 7,435,248 B2 | 10/2008 | Taimisto et al. |
| 7,447,453 B2 | 11/2008 | Kim et al. |
| 7,449,018 B2 | 11/2008 | Kramer |
| 7,452,538 B2 | 11/2008 | Ni et al. |
| 7,473,890 B2 | 1/2009 | Grier et al. |
| 7,476,384 B2 | 1/2009 | Ni et al. |
| 7,479,157 B2 | 1/2009 | Weber et al. |
| 7,481,803 B2 | 1/2009 | Kesten et al. |
| 7,485,104 B2 | 2/2009 | Kieval |
| 7,486,805 B2 | 2/2009 | Krattiger |
| 7,487,780 B2 | 2/2009 | Hooven |
| 7,493,154 B2 | 2/2009 | Bonner et al. |
| 7,494,485 B2 | 2/2009 | Beck et al. |
| 7,494,486 B2 | 2/2009 | Mische et al. |
| 7,494,488 B2 | 2/2009 | Weber |
| 7,494,661 B2 | 2/2009 | Sanders |
| 7,495,439 B2 | 2/2009 | Wiggins |
| 7,497,858 B2 | 3/2009 | Chapelon et al. |
| 7,499,745 B2 | 3/2009 | Littrup et al. |
| 7,500,985 B2 | 3/2009 | Saadat |
| 7,505,812 B1 | 3/2009 | Eggers et al. |
| 7,505,816 B2 | 3/2009 | Schmeling et al. |
| 7,507,233 B2 | 3/2009 | Littrup et al. |
| 7,507,235 B2 | 3/2009 | Keogh et al. |
| 7,511,494 B2 | 3/2009 | Wedeen |
| 7,512,445 B2 | 3/2009 | Truckai et al. |
| 7,527,643 B2 | 5/2009 | Case et al. |
| 7,529,589 B2 | 5/2009 | Williams et al. |
| 7,540,852 B2 | 6/2009 | Nita et al. |
| 7,540,870 B2 | 6/2009 | Babaev |
| RE40,863 E | 7/2009 | Tay et al. |
| 7,556,624 B2 | 7/2009 | Laufer et al. |
| 7,558,625 B2 | 7/2009 | Levin et al. |
| 7,563,247 B2 | 7/2009 | Maguire et al. |
| 7,566,319 B2 | 7/2009 | McAuley et al. |
| 7,569,052 B2 | 8/2009 | Phan et al. |
| 7,582,111 B2 | 9/2009 | Krolik et al. |
| 7,584,004 B2 | 9/2009 | Caparso et al. |
| 7,585,835 B2 | 9/2009 | Hill et al. |
| 7,591,996 B2 | 9/2009 | Hwang et al. |
| 7,597,704 B2 | 10/2009 | Frazier et al. |
| 7,598,228 B2 | 10/2009 | Hattori et al. |
| 7,599,730 B2 | 10/2009 | Hunter et al. |
| 7,603,166 B2 | 10/2009 | Casscells, III et al. |
| 7,604,608 B2 | 10/2009 | Nita et al. |
| 7,604,633 B2 | 10/2009 | Truckai et al. |
| 7,615,015 B2 | 11/2009 | Coleman |
| 7,615,072 B2 | 11/2009 | Rust et al. |
| 7,617,005 B2 | 11/2009 | Demarais et al. |
| 7,620,451 B2 | 11/2009 | Demarais et al. |
| 7,621,902 B2 | 11/2009 | Nita et al. |
| 7,621,929 B2 | 11/2009 | Nita et al. |
| 7,626,015 B2 | 12/2009 | Feinstein et al. |
| 7,626,235 B2 | 12/2009 | Kinoshita |
| 7,632,268 B2 | 12/2009 | Edwards et al. |
| 7,632,845 B2 | 12/2009 | Vu et al. |
| 7,635,383 B2 | 12/2009 | Gumm |
| 7,640,046 B2 | 12/2009 | Pastore et al. |
| 7,641,633 B2 | 1/2010 | Laufer et al. |
| 7,641,679 B2 | 1/2010 | Joye et al. |
| 7,646,544 B2 | 1/2010 | Batchko et al. |
| 7,647,115 B2 | 1/2010 | Levin et al. |
| 7,653,438 B2 | 1/2010 | Deem et al. |
| 7,655,006 B2 | 2/2010 | Sauvageau et al. |
| 7,662,114 B2 | 2/2010 | Seip et al. |
| 7,664,548 B2 | 2/2010 | Amurthur et al. |
| 7,670,279 B2 | 3/2010 | Gertner |
| 7,670,335 B2 | 3/2010 | Keidar |
| 7,671,084 B2 | 3/2010 | Mewshaw et al. |
| 7,678,104 B2 | 3/2010 | Keidar |
| 7,678,106 B2 | 3/2010 | Lee |
| 7,678,108 B2 | 3/2010 | Chrisitian et al. |
| 7,691,080 B2 | 4/2010 | Seward et al. |
| 7,699,809 B2 | 4/2010 | Urmey |
| 7,706,882 B2 | 4/2010 | Francischelli et al. |
| 7,715,912 B2 | 5/2010 | Rezai et al. |
| 7,717,853 B2 | 5/2010 | Nita |
| 7,717,909 B2 | 5/2010 | Strul et al. |
| 7,717,948 B2 | 5/2010 | Demarais et al. |
| 7,722,539 B2 | 5/2010 | Carter et al. |
| 7,725,157 B2 | 5/2010 | Dumoulin et al. |
| 7,727,178 B2 | 6/2010 | Wilson et al. |
| 7,736,317 B2 | 6/2010 | Stephens et al. |
| 7,736,360 B2 | 6/2010 | Mody et al. |
| 7,736,362 B2 | 6/2010 | Eberl et al. |
| 7,738,952 B2 | 6/2010 | Yun et al. |
| 7,740,629 B2 | 6/2010 | Anderson et al. |
| 7,741,299 B2 | 6/2010 | Feinstein et al. |
| 7,742,795 B2 | 6/2010 | Stone et al. |
| 7,744,594 B2 | 6/2010 | Yamazaki et al. |
| 7,753,907 B2 | 7/2010 | DiMatteo et al. |
| 7,756,583 B2 | 7/2010 | Demarais et al. |
| 7,758,510 B2 | 7/2010 | Nita et al. |
| 7,758,520 B2 | 7/2010 | Griffin et al. |
| 7,759,315 B2 | 7/2010 | Cuzzocrea et al. |
| 7,766,833 B2 | 8/2010 | Lee et al. |
| 7,766,878 B2 | 8/2010 | Tremaglio, Jr. et al. |
| 7,766,892 B2 | 8/2010 | Keren et al. |
| 7,767,844 B2 | 8/2010 | Lee et al. |
| 7,769,427 B2 | 8/2010 | Shachar |
| 7,771,372 B2 | 8/2010 | Wilson |
| 7,771,421 B2 | 8/2010 | Stewart et al. |
| 7,776,967 B2 | 8/2010 | Perry et al. |
| 7,777,486 B2 | 8/2010 | Hargreaves et al. |
| 7,780,660 B2 | 8/2010 | Bourne et al. |
| 7,789,876 B2 | 9/2010 | Zikorus et al. |
| 7,792,568 B2 | 9/2010 | Zhong et al. |
| 7,799,021 B2 | 9/2010 | Leung et al. |
| 7,803,168 B2 | 9/2010 | Gifford et al. |
| 7,806,871 B2 | 10/2010 | Li et al. |
| 7,811,265 B2 | 10/2010 | Hering et al. |
| 7,811,281 B1 | 10/2010 | Rentrop |
| 7,811,313 B2 | 10/2010 | Mon et al. |
| 7,816,511 B2 | 10/2010 | Kawashima et al. |
| 7,818,053 B2 | 10/2010 | Kassab |
| 7,819,866 B2 | 10/2010 | Bednarek |
| 7,822,460 B2 | 10/2010 | Halperin et al. |
| 7,828,837 B2 | 11/2010 | Khoury |
| 7,832,407 B2 | 11/2010 | Gertner |
| 7,833,220 B2 | 11/2010 | Mon et al. |
| 7,837,676 B2 | 11/2010 | Sinelnikov et al. |
| 7,837,720 B2 | 11/2010 | Mon |
| 7,841,978 B2 | 11/2010 | Gertner |

(56) References Cited

U.S. PATENT DOCUMENTS

| | | |
|---|---|---|
| 7,846,157 B2 | 12/2010 | Kozel |
| 7,846,160 B2 | 12/2010 | Payne et al. |
| 7,846,172 B2 | 12/2010 | Makower |
| 7,849,860 B2 | 12/2010 | Makower et al. |
| 7,850,685 B2 | 12/2010 | Kunis et al. |
| 7,853,333 B2 | 12/2010 | Demarais |
| 7,854,734 B2 | 12/2010 | Biggs et al. |
| 7,857,756 B2 | 12/2010 | Warren et al. |
| 7,862,565 B2 | 1/2011 | Eder et al. |
| 7,863,897 B2 | 1/2011 | Slocum, Jr. et al. |
| 7,869,854 B2 | 1/2011 | Shachar et al. |
| 7,873,417 B2 | 1/2011 | Demarais et al. |
| 7,887,538 B2 | 2/2011 | Bleich et al. |
| 7,894,905 B2 | 2/2011 | Pless et al. |
| 7,896,873 B2 | 3/2011 | Hiller et al. |
| 7,901,400 B2 | 3/2011 | Wham et al. |
| 7,901,402 B2 | 3/2011 | Jones et al. |
| 7,901,420 B2 | 3/2011 | Dunn |
| 7,905,862 B2 | 3/2011 | Sampson |
| 7,918,850 B2 | 4/2011 | Govari et al. |
| 7,927,370 B2 | 4/2011 | Webler et al. |
| 7,937,143 B2 | 5/2011 | Demarais et al. |
| 7,938,830 B2 | 5/2011 | Saadat et al. |
| 7,942,874 B2 | 5/2011 | Eder et al. |
| 7,942,928 B2 | 5/2011 | Webler et al. |
| 7,946,976 B2 | 5/2011 | Gertner |
| 7,950,397 B2 | 5/2011 | Thapliyal et al. |
| 7,955,293 B2 | 6/2011 | Nita et al. |
| 7,956,613 B2 | 6/2011 | Wald |
| 7,959,627 B2 | 6/2011 | Utley et al. |
| 7,959,630 B2 | 6/2011 | Taimisto et al. |
| 7,962,854 B2 | 6/2011 | Vance et al. |
| 7,967,782 B2 | 6/2011 | Laufer et al. |
| 7,967,808 B2 | 6/2011 | Fitzgerald et al. |
| 7,972,327 B2 | 7/2011 | Eberl et al. |
| 7,972,330 B2 | 7/2011 | Alejandro et al. |
| 7,983,751 B2 | 7/2011 | Zdeblick et al. |
| 8,001,976 B2 | 8/2011 | Gertner |
| 8,007,440 B2 | 8/2011 | Magnin et al. |
| 8,012,147 B2 | 9/2011 | Lafontaine |
| 8,019,435 B2 | 9/2011 | Hastings et al. |
| 8,021,362 B2 | 9/2011 | Deem et al. |
| 8,021,413 B2 | 9/2011 | Dierking et al. |
| 8,025,661 B2 | 9/2011 | Arnold et al. |
| 8,027,718 B2 | 9/2011 | Spinner et al. |
| 8,031,927 B2 | 10/2011 | Karl et al. |
| 8,033,284 B2 | 10/2011 | Porter et al. |
| 8,048,144 B2 | 11/2011 | Thistle et al. |
| 8,052,636 B2 | 11/2011 | Moll et al. |
| 8,052,700 B2 | 11/2011 | Dunn |
| 8,062,289 B2 | 11/2011 | Babaev |
| 8,075,580 B2 | 12/2011 | Makower |
| 8,080,006 B2 | 12/2011 | Lafontaine et al. |
| 8,088,127 B2 | 1/2012 | Mayse et al. |
| 8,116,883 B2 | 2/2012 | Williams et al. |
| 8,119,183 B2 | 2/2012 | O'Donoghue et al. |
| 8,120,518 B2 | 2/2012 | Jang et al. |
| 8,123,741 B2 | 2/2012 | Marrouche et al. |
| 8,128,617 B2 | 3/2012 | Bencini et al. |
| 8,131,371 B2 | 3/2012 | Demarals et al. |
| 8,131,372 B2 | 3/2012 | Levin et al. |
| 8,131,382 B2 | 3/2012 | Asada |
| 8,137,274 B2 | 3/2012 | Weng et al. |
| 8,140,170 B2 | 3/2012 | Rezai et al. |
| 8,143,316 B2 | 3/2012 | Ueno |
| 8,145,316 B2 | 3/2012 | Deem et al. |
| 8,145,317 B2 | 3/2012 | Demarais et al. |
| 8,150,518 B2 | 4/2012 | Levin et al. |
| 8,150,519 B2 | 4/2012 | Demarais et al. |
| 8,150,520 B2 | 4/2012 | Demarais et al. |
| 8,152,830 B2 | 4/2012 | Gumm |
| 8,162,933 B2 | 4/2012 | Francischelli et al. |
| 8,175,711 B2 | 5/2012 | Demarais et al. |
| 8,187,261 B2 | 5/2012 | Watson |
| 8,190,238 B2 | 5/2012 | Moll et al. |
| 8,192,053 B2 | 6/2012 | Owen et al. |
| 8,198,611 B2 | 6/2012 | LaFontaine et al. |
| 8,214,056 B2 | 7/2012 | Hoffer et al. |
| 8,221,407 B2 | 7/2012 | Phan et al. |
| 8,226,637 B2 | 7/2012 | Satake |
| 8,231,617 B2 | 7/2012 | Satake |
| 8,241,217 B2 | 8/2012 | Chiang et al. |
| 8,257,724 B2 | 9/2012 | Cromack et al. |
| 8,257,725 B2 | 9/2012 | Cromack et al. |
| 8,260,397 B2 | 9/2012 | Ruff et al. |
| 8,263,104 B2 | 9/2012 | Ho et al. |
| 8,273,023 B2 | 9/2012 | Razavi |
| 8,277,379 B2 | 10/2012 | Lau et al. |
| 8,287,524 B2 | 10/2012 | Siegel |
| 8,287,532 B2 | 10/2012 | Carroll et al. |
| 8,292,881 B2 | 10/2012 | Brannan et al. |
| 8,293,703 B2 | 10/2012 | Averback et al. |
| 8,295,902 B2 | 10/2012 | Salahieh et al. |
| 8,295,912 B2 | 10/2012 | Gertner |
| 8,308,722 B2 | 11/2012 | Ormsby et al. |
| 8,317,776 B2 | 11/2012 | Ferren et al. |
| 8,317,810 B2 | 11/2012 | Stangenes et al. |
| 8,329,179 B2 | 12/2012 | Ni et al. |
| 8,336,705 B2 | 12/2012 | Okahisa |
| 8,343,031 B2 | 1/2013 | Gertner |
| 8,343,145 B2 | 1/2013 | Brannan |
| 8,347,891 B2 | 1/2013 | Demarais et al. |
| 8,353,945 B2 | 1/2013 | Andreas et al. |
| 8,364,237 B2 | 1/2013 | Stone et al. |
| 8,366,615 B2 | 2/2013 | Razavi |
| 8,382,697 B2 | 2/2013 | Brenneman et al. |
| 8,388,680 B2 | 3/2013 | Starksen et al. |
| 8,396,548 B2 | 3/2013 | Perry et al. |
| 8,398,629 B2 | 3/2013 | Thistle |
| 8,401,667 B2 | 3/2013 | Gustus et al. |
| 8,403,881 B2 | 3/2013 | Ferren et al. |
| 8,406,877 B2 | 3/2013 | Smith et al. |
| 8,409,172 B2 | 4/2013 | Moll et al. |
| 8,409,193 B2 | 4/2013 | Young et al. |
| 8,409,195 B2 | 4/2013 | Young |
| 8,418,362 B2 | 4/2013 | Zerfas et al. |
| 8,452,988 B2 | 5/2013 | Wang |
| 8,454,594 B2 | 6/2013 | Demarais et al. |
| 8,460,358 B2 | 6/2013 | Andreas et al. |
| 8,465,452 B2 | 6/2013 | Kassab |
| 8,469,919 B2 | 6/2013 | Ingle et al. |
| 8,473,067 B2 | 6/2013 | Hastings et al. |
| 8,480,663 B2 | 7/2013 | Ingle et al. |
| 8,485,992 B2 | 7/2013 | Griffin et al. |
| 8,486,060 B2 | 7/2013 | Kotmel et al. |
| 8,486,063 B2 | 7/2013 | Werneth et al. |
| 8,488,591 B2 | 7/2013 | Miali et al. |
| 2001/0007070 A1 | 7/2001 | Stewart |
| 2001/0039419 A1 | 11/2001 | Francischelli et al. |
| 2002/0022864 A1 | 2/2002 | Mahvi et al. |
| 2002/0042639 A1 | 4/2002 | Murphy-Chutorian et al. |
| 2002/0045811 A1 | 4/2002 | Kittrell et al. |
| 2002/0045890 A1 | 4/2002 | Celliers et al. |
| 2002/0062146 A1 | 5/2002 | Makower |
| 2002/0065542 A1 | 5/2002 | Lax et al. |
| 2002/0087151 A1 | 7/2002 | Mody et al. |
| 2002/0095197 A1 | 7/2002 | Lardo et al. |
| 2002/0107536 A1 | 8/2002 | Hussein |
| 2002/0147480 A1 | 10/2002 | Mamayek |
| 2002/0169444 A1 | 11/2002 | Mest et al. |
| 2002/0198520 A1 | 12/2002 | Coen et al. |
| 2003/0065317 A1 | 4/2003 | Rudie et al. |
| 2003/0092995 A1 | 5/2003 | Thompson |
| 2003/0125721 A1 | 7/2003 | Yon |
| 2003/0139689 A1 | 7/2003 | Shturman et al. |
| 2003/0155539 A1 | 8/2003 | Ginggen |
| 2003/0187368 A1 | 10/2003 | Sata |
| 2003/0195501 A1 | 10/2003 | Sherman et al. |
| 2003/0199747 A1 | 10/2003 | Michlitsch et al. |
| 2003/0225442 A1 | 12/2003 | Saadat |
| 2004/0010118 A1 | 1/2004 | Zerhusen et al. |
| 2004/0019348 A1 | 1/2004 | Stevens et al. |
| 2004/0024371 A1 | 2/2004 | Plicchi et al. |
| 2004/0043030 A1 | 3/2004 | Griffiths et al. |

(56) References Cited

U.S. PATENT DOCUMENTS

| | | |
|---|---|---|
| 2004/0049181 A1* | 3/2004 | Stewart et al. .................. 606/41 |
| 2004/0064090 A1 | 4/2004 | Keren et al. |
| 2004/0073206 A1 | 4/2004 | Foley et al. |
| 2004/0073238 A1 | 4/2004 | Makower |
| 2004/0088002 A1 | 5/2004 | Boyle et al. |
| 2004/0093055 A1 | 5/2004 | Bartorelli et al. |
| 2004/0106871 A1 | 6/2004 | Hunyor et al. |
| 2004/0117032 A1 | 6/2004 | Roth |
| 2004/0147914 A1 | 7/2004 | Kramer |
| 2004/0147915 A1 | 7/2004 | Hasebe |
| 2004/0162555 A1 | 8/2004 | Farley et al. |
| 2004/0167506 A1 | 8/2004 | Chen |
| 2004/0186356 A1 | 9/2004 | O'Malley et al. |
| 2004/0187875 A1 | 9/2004 | He et al. |
| 2004/0193211 A1 | 9/2004 | Voegele et al. |
| 2004/0220556 A1 | 11/2004 | Cooper et al. |
| 2004/0243022 A1 | 12/2004 | Carney et al. |
| 2004/0243201 A1 | 12/2004 | Goldman et al. |
| 2004/0253304 A1 | 12/2004 | Gross et al. |
| 2004/0267250 A1 | 12/2004 | Yon |
| 2004/0267258 A1 | 12/2004 | Zikorus |
| 2005/0010095 A1 | 1/2005 | Stewart et al. |
| 2005/0015125 A1 | 1/2005 | Mioduski et al. |
| 2005/0055020 A1* | 3/2005 | Skarda .......................... 606/41 |
| 2005/0055073 A1 | 3/2005 | Weber |
| 2005/0065505 A1* | 3/2005 | Ryan .............................. 606/27 |
| 2005/0080374 A1 | 4/2005 | Esch et al. |
| 2005/0129616 A1 | 6/2005 | Salcedo et al. |
| 2005/0137180 A1 | 6/2005 | Robinson et al. |
| 2005/0143817 A1 | 6/2005 | Hunter et al. |
| 2005/0148842 A1 | 7/2005 | Wang et al. |
| 2005/0149069 A1 | 7/2005 | Bertolero et al. |
| 2005/0149080 A1 | 7/2005 | Hunter et al. |
| 2005/0149158 A1 | 7/2005 | Hunter et al. |
| 2005/0149173 A1 | 7/2005 | Hunter et al. |
| 2005/0149175 A1 | 7/2005 | Hunter et al. |
| 2005/0154277 A1 | 7/2005 | Tang et al. |
| 2005/0154445 A1 | 7/2005 | Hunter et al. |
| 2005/0154453 A1 | 7/2005 | Hunter et al. |
| 2005/0154454 A1 | 7/2005 | Hunter et al. |
| 2005/0165389 A1 | 7/2005 | Swain et al. |
| 2005/0165391 A1 | 7/2005 | Maguire et al. |
| 2005/0165467 A1 | 7/2005 | Hunter et al. |
| 2005/0165488 A1 | 7/2005 | Hunter et al. |
| 2005/0175661 A1 | 8/2005 | Hunter et al. |
| 2005/0175662 A1 | 8/2005 | Hunter et al. |
| 2005/0175663 A1 | 8/2005 | Hunter et al. |
| 2005/0177103 A1 | 8/2005 | Hunter et al. |
| 2005/0177225 A1 | 8/2005 | Hunter et al. |
| 2005/0181004 A1 | 8/2005 | Hunter et al. |
| 2005/0181008 A1 | 8/2005 | Hunter et al. |
| 2005/0181011 A1 | 8/2005 | Hunter et al. |
| 2005/0181977 A1 | 8/2005 | Hunter et al. |
| 2005/0182479 A1 | 8/2005 | Bonsignore et al. |
| 2005/0183728 A1 | 8/2005 | Hunter et al. |
| 2005/0186242 A1 | 8/2005 | Hunter et al. |
| 2005/0186243 A1 | 8/2005 | Hunter et al. |
| 2005/0191331 A1 | 9/2005 | Hunter et al. |
| 2005/0203410 A1 | 9/2005 | Jenkins |
| 2005/0209587 A1 | 9/2005 | Joye |
| 2005/0214205 A1 | 9/2005 | Salcedo et al. |
| 2005/0214207 A1 | 9/2005 | Salcedo et al. |
| 2005/0214208 A1 | 9/2005 | Salcedo et al. |
| 2005/0214209 A1 | 9/2005 | Salcedo et al. |
| 2005/0214210 A1 | 9/2005 | Salcedo et al. |
| 2005/0214268 A1 | 9/2005 | Cavanagh et al. |
| 2005/0228286 A1 | 10/2005 | Messerly et al. |
| 2005/0228415 A1 | 10/2005 | Gertner |
| 2005/0228460 A1 | 10/2005 | Levin et al. |
| 2005/0232921 A1 | 10/2005 | Rosen et al. |
| 2005/0234312 A1 | 10/2005 | Suzuki et al. |
| 2005/0245862 A1 | 11/2005 | Seward |
| 2005/0251116 A1 | 11/2005 | Steinke et al. |
| 2005/0251240 A1* | 11/2005 | Doan .......................... 607/127 |
| 2005/0252553 A1 | 11/2005 | Ginggen |
| 2005/0256398 A1 | 11/2005 | Hastings et al. |
| 2005/0256521 A1 | 11/2005 | Kozel |
| 2005/0267556 A1 | 12/2005 | Shuros et al. |
| 2006/0004323 A1 | 1/2006 | Chang et al. |
| 2006/0018949 A1 | 1/2006 | Ammon et al. |
| 2006/0024564 A1 | 2/2006 | Manclaw et al. |
| 2006/0025765 A1 | 2/2006 | Landman et al. |
| 2006/0041277 A1 | 2/2006 | Deem et al. |
| 2006/0062786 A1 | 3/2006 | Salcedo et al. |
| 2006/0083194 A1 | 4/2006 | Dhrimaj et al. |
| 2006/0089637 A1 | 4/2006 | Werneth et al. |
| 2006/0089638 A1 | 4/2006 | Carmel et al. |
| 2006/0095096 A1 | 5/2006 | DeBenedictis et al. |
| 2006/0106375 A1 | 5/2006 | Werneth et al. |
| 2006/0142790 A1 | 6/2006 | Gertner |
| 2006/0142801 A1 | 6/2006 | Demarais et al. |
| 2006/0147492 A1 | 7/2006 | Hunter et al. |
| 2006/0167106 A1 | 7/2006 | Zhang |
| 2006/0167498 A1 | 7/2006 | DiLorenzo |
| 2006/0171895 A1 | 8/2006 | Bucay-Couto |
| 2006/0184089 A1 | 8/2006 | Makower et al. |
| 2006/0184221 A1 | 8/2006 | Stewart et al. |
| 2006/0195139 A1 | 8/2006 | Gertner |
| 2006/0206150 A1 | 9/2006 | Demarais et al. |
| 2006/0212076 A1 | 9/2006 | Demarais et al. |
| 2006/0212078 A1 | 9/2006 | Demarais et al. |
| 2006/0224153 A1 | 10/2006 | Fischell et al. |
| 2006/0239921 A1 | 10/2006 | Mangat et al. |
| 2006/0240070 A1 | 10/2006 | Cromack et al. |
| 2006/0247266 A1 | 11/2006 | Yamada et al. |
| 2006/0247760 A1 | 11/2006 | Ganesan et al. |
| 2006/0253183 A1* | 11/2006 | Thagalingam et al. ....... 607/120 |
| 2006/0263393 A1 | 11/2006 | Demopulos et al. |
| 2006/0265014 A1 | 11/2006 | Demarais et al. |
| 2006/0265015 A1 | 11/2006 | Demarais et al. |
| 2006/0269555 A1 | 11/2006 | Salcedo et al. |
| 2006/0271111 A1 | 11/2006 | Demarais et al. |
| 2006/0276852 A1 | 12/2006 | Demarais et al. |
| 2006/0287644 A1 | 12/2006 | Inganas et al. |
| 2007/0016184 A1 | 1/2007 | Cropper et al. |
| 2007/0016274 A1 | 1/2007 | Boveja et al. |
| 2007/0021745 A1* | 1/2007 | McIntyre et al. ............... 606/41 |
| 2007/0027390 A1 | 2/2007 | Maschke et al. |
| 2007/0043077 A1 | 2/2007 | Mewshaw et al. |
| 2007/0043338 A1 | 2/2007 | Moll et al. |
| 2007/0043409 A1 | 2/2007 | Brian et al. |
| 2007/0049924 A1 | 3/2007 | Rahn |
| 2007/0066957 A1 | 3/2007 | Demarais et al. |
| 2007/0066972 A1 | 3/2007 | Ormsby et al. |
| 2007/0073151 A1 | 3/2007 | Lee |
| 2007/0093710 A1 | 4/2007 | Maschke |
| 2007/0100405 A1 | 5/2007 | Thompson et al. |
| 2007/0106247 A1 | 5/2007 | Burnett et al. |
| 2007/0112327 A1 | 5/2007 | Yun et al. |
| 2007/0118107 A1 | 5/2007 | Francischelli et al. |
| 2007/0123852 A1 | 5/2007 | Deem et al. |
| 2007/0129720 A1 | 6/2007 | Demarais et al. |
| 2007/0129760 A1 | 6/2007 | Demarais et al. |
| 2007/0129761 A1 | 6/2007 | Demarais et al. |
| 2007/0135875 A1 | 6/2007 | Demarais et al. |
| 2007/0149963 A1 | 6/2007 | Matsukuma et al. |
| 2007/0162109 A1 | 7/2007 | Davila et al. |
| 2007/0173805 A1 | 7/2007 | Weinberg et al. |
| 2007/0173899 A1 | 7/2007 | Levin |
| 2007/0179496 A1 | 8/2007 | Swoyer et al. |
| 2007/0197896 A1 | 8/2007 | Moll et al. |
| 2007/0203480 A1 | 8/2007 | Mody et al. |
| 2007/0203549 A1 | 8/2007 | Demarais et al. |
| 2007/0207186 A1 | 9/2007 | Scanlon et al. |
| 2007/0208134 A1 | 9/2007 | Hunter et al. |
| 2007/0208210 A1 | 9/2007 | Gelfand et al. |
| 2007/0208256 A1 | 9/2007 | Marilla |
| 2007/0208301 A1 | 9/2007 | Evard |
| 2007/0219576 A1 | 9/2007 | Cangialosi |
| 2007/0225781 A1 | 9/2007 | Saadat et al. |
| 2007/0233170 A1 | 10/2007 | Gertner |
| 2007/0239062 A1 | 10/2007 | Chopra et al. |
| 2007/0248639 A1 | 10/2007 | Demopulos et al. |
| 2007/0249703 A1 | 10/2007 | Mewshaw et al. |

(56) References Cited

U.S. PATENT DOCUMENTS

| | | |
|---|---|---|
| 2007/0250050 A1 | 10/2007 | Lafontaine |
| 2007/0254833 A1 | 11/2007 | Hunter et al. |
| 2007/0260281 A1 | 11/2007 | Hastings |
| 2007/0265687 A1 | 11/2007 | Deem et al. |
| 2007/0276461 A1 | 11/2007 | Andreas et al. |
| 2007/0278103 A1 | 12/2007 | Hoerr et al. |
| 2007/0282302 A1 | 12/2007 | Wachsman et al. |
| 2007/0292411 A1 | 12/2007 | Salcedo et al. |
| 2007/0293782 A1 | 12/2007 | Marino |
| 2007/0299043 A1 | 12/2007 | Hunter et al. |
| 2008/0004673 A1 | 1/2008 | Rossing |
| 2008/0009927 A1 | 1/2008 | Vilims |
| 2008/0015501 A1 | 1/2008 | Gertner |
| 2008/0015570 A1 | 1/2008 | Ormsby et al. |
| 2008/0021408 A1 | 1/2008 | Jacobsen |
| 2008/0033049 A1 | 2/2008 | Mewshaw |
| 2008/0039746 A1 | 2/2008 | Hissong et al. |
| 2008/0039830 A1 | 2/2008 | Munger et al. |
| 2008/0051454 A1 | 2/2008 | Wang |
| 2008/0058836 A1 | 3/2008 | Moll et al. |
| 2008/0064957 A1 | 3/2008 | Spence |
| 2008/0071269 A1 | 3/2008 | Hilario et al. |
| 2008/0071306 A1 | 3/2008 | Gertner |
| 2008/0082109 A1 | 4/2008 | Moll et al. |
| 2008/0086072 A1 | 4/2008 | Bonutti et al. |
| 2008/0091193 A1 | 4/2008 | Kauphusman et al. |
| 2008/0097251 A1 | 4/2008 | Babaev |
| 2008/0097299 A1 | 4/2008 | Andreas et al. |
| 2008/0097426 A1 | 4/2008 | Root et al. |
| 2008/0103575 A1 * | 5/2008 | Gerber ................... 607/117 |
| 2008/0108867 A1 | 5/2008 | Zhou |
| 2008/0119879 A1 | 5/2008 | Brenneman et al. |
| 2008/0125772 A1 | 5/2008 | Stone et al. |
| 2008/0132450 A1 | 6/2008 | Lee |
| 2008/0140002 A1 | 6/2008 | Ramzipoor et al. |
| 2008/0147002 A1 | 6/2008 | Gertner |
| 2008/0161662 A1 | 7/2008 | Golijanin et al. |
| 2008/0161717 A1 | 7/2008 | Gertner |
| 2008/0161801 A1 | 7/2008 | Steinke et al. |
| 2008/0171974 A1 | 7/2008 | Lafontaine et al. |
| 2008/0172035 A1 | 7/2008 | Starksen et al. |
| 2008/0172104 A1 | 7/2008 | Kieval et al. |
| 2008/0188912 A1 | 8/2008 | Stone et al. |
| 2008/0188913 A1 | 8/2008 | Stone et al. |
| 2008/0208162 A1 | 8/2008 | Joshi |
| 2008/0208169 A1 | 8/2008 | Boyle et al. |
| 2008/0213331 A1 | 9/2008 | Gelfand et al. |
| 2008/0215117 A1 | 9/2008 | Gross |
| 2008/0221448 A1 | 9/2008 | Khuri-Yakub et al. |
| 2008/0234790 A1 | 9/2008 | Bayer et al. |
| 2008/0243091 A1 | 10/2008 | Humphreys et al. |
| 2008/0245371 A1 | 10/2008 | Gruber |
| 2008/0249525 A1 | 10/2008 | Lee et al. |
| 2008/0249547 A1 | 10/2008 | Dunn |
| 2008/0255550 A1 | 10/2008 | Bell |
| 2008/0255642 A1 | 10/2008 | Zarins et al. |
| 2008/0262489 A1 | 10/2008 | Steinke |
| 2008/0275484 A1 | 11/2008 | Gertner |
| 2008/0281312 A1 | 11/2008 | Werneth et al. |
| 2008/0281347 A1 | 11/2008 | Gertner |
| 2008/0287918 A1 | 11/2008 | Rosenman et al. |
| 2008/0294037 A1 | 11/2008 | Richter |
| 2008/0300618 A1 | 12/2008 | Gertner |
| 2008/0312644 A1 | 12/2008 | Fourkas et al. |
| 2008/0312673 A1 | 12/2008 | Viswanathan et al. |
| 2008/0317818 A1 | 12/2008 | Griffith et al. |
| 2009/0005775 A1 | 1/2009 | Jones et al. |
| 2009/0018486 A1 | 1/2009 | Goren et al. |
| 2009/0018609 A1 | 1/2009 | DiLorenzo |
| 2009/0024194 A1 | 1/2009 | Arcot-Krishnamurthy et al. |
| 2009/0030312 A1 | 1/2009 | Hadjicostis |
| 2009/0036872 A1 | 2/2009 | Fitzgerald |
| 2009/0036948 A1 | 2/2009 | Levin et al. |
| 2009/0043372 A1 | 2/2009 | Northrop |
| 2009/0054082 A1 | 2/2009 | Kim et al. |
| 2009/0062873 A1 | 3/2009 | Wu et al. |
| 2009/0069671 A1 | 3/2009 | Anderson |
| 2009/0076409 A1 | 3/2009 | Wu et al. |
| 2009/0088735 A1 | 4/2009 | Abboud et al. |
| 2009/0105631 A1 | 4/2009 | Kieval |
| 2009/0112202 A1 | 4/2009 | Young |
| 2009/0118620 A1 | 5/2009 | Tgavalekos et al. |
| 2009/0118726 A1 | 5/2009 | Auth et al. |
| 2009/0125099 A1 | 5/2009 | Weber et al. |
| 2009/0131798 A1 | 5/2009 | Minar et al. |
| 2009/0143640 A1 | 6/2009 | Saadat et al. |
| 2009/0156988 A1 | 6/2009 | Ferren et al. |
| 2009/0157057 A1 | 6/2009 | Ferren et al. |
| 2009/0157161 A1 | 6/2009 | Desai |
| 2009/0171333 A1 | 7/2009 | Hon |
| 2009/0182360 A1 | 7/2009 | Makower |
| 2009/0192558 A1 | 7/2009 | Whitehurst et al. |
| 2009/0198223 A1 | 8/2009 | Thilwind et al. |
| 2009/0203962 A1 | 8/2009 | Miller et al. |
| 2009/0203993 A1 | 8/2009 | Mangat et al. |
| 2009/0204170 A1 | 8/2009 | Hastings |
| 2009/0210953 A1 | 8/2009 | Moyer |
| 2009/0216317 A1 | 8/2009 | Cromack et al. |
| 2009/0221939 A1 | 9/2009 | Demarais et al. |
| 2009/0221955 A1 | 9/2009 | Babaev |
| 2009/0226429 A1 | 9/2009 | Salcedo et al. |
| 2009/0240249 A1 | 9/2009 | Chan et al. |
| 2009/0247933 A1 | 10/2009 | Maor et al. |
| 2009/0247966 A1 | 10/2009 | Gunn et al. |
| 2009/0248012 A1 | 10/2009 | Maor et al. |
| 2009/0253974 A1 | 10/2009 | Rahme |
| 2009/0264755 A1 | 10/2009 | Chen et al. |
| 2009/0270850 A1 | 10/2009 | Zhou et al. |
| 2009/0281533 A1 | 11/2009 | Ingle et al. |
| 2009/0287137 A1 | 11/2009 | Crowley |
| 2009/0318749 A1 | 12/2009 | Stolen et al. |
| 2010/0009267 A1 | 1/2010 | Chase et al. |
| 2010/0030061 A1 | 2/2010 | Canfield et al. |
| 2010/0048983 A1 | 2/2010 | Ball et al. |
| 2010/0049099 A1 | 2/2010 | Thapliyal et al. |
| 2010/0049186 A1 | 2/2010 | Ingle et al. |
| 2010/0049188 A1 | 2/2010 | Nelson et al. |
| 2010/0049191 A1 | 2/2010 | Habib et al. |
| 2010/0049283 A1 | 2/2010 | Johnson |
| 2010/0057150 A1 | 3/2010 | Demarais et al. |
| 2010/0069837 A1 | 3/2010 | Rassat et al. |
| 2010/0076299 A1 | 3/2010 | Gustus et al. |
| 2010/0076425 A1 | 3/2010 | Carroux |
| 2010/0087782 A1 | 4/2010 | Ghaffari et al. |
| 2010/0106005 A1 | 4/2010 | Karczmar et al. |
| 2010/0106156 A1 | 4/2010 | Laufer et al. |
| 2010/0114244 A1 | 5/2010 | Manda et al. |
| 2010/0130836 A1 | 5/2010 | Malchano et al. |
| 2010/0137860 A1 | 6/2010 | Demarais et al. |
| 2010/0137952 A1 | 6/2010 | Demarais et al. |
| 2010/0160903 A1 | 6/2010 | Krespi |
| 2010/0160906 A1 | 6/2010 | Jarrard |
| 2010/0168624 A1 | 7/2010 | Sliwa |
| 2010/0168731 A1 | 7/2010 | Wu et al. |
| 2010/0168739 A1 | 7/2010 | Wu et al. |
| 2010/0174169 A1 | 7/2010 | Razavi |
| 2010/0174170 A1 | 7/2010 | Razavi |
| 2010/0174252 A1 | 7/2010 | Stangenes et al. |
| 2010/0174282 A1 | 7/2010 | Demarais et al. |
| 2010/0191112 A1 | 7/2010 | Demarais et al. |
| 2010/0191232 A1 | 7/2010 | Boveda |
| 2010/0217162 A1 | 8/2010 | Hissong et al. |
| 2010/0222786 A1 | 9/2010 | Kassab |
| 2010/0222851 A1 | 9/2010 | Deem et al. |
| 2010/0222854 A1 | 9/2010 | Demarais et al. |
| 2010/0228122 A1 | 9/2010 | Keenan et al. |
| 2010/0249604 A1 | 9/2010 | Hastings et al. |
| 2010/0249773 A1 | 9/2010 | Clark et al. |
| 2010/0256616 A1 | 10/2010 | Katoh et al. |
| 2010/0268217 A1 | 10/2010 | Habib |
| 2010/0268307 A1 | 10/2010 | Demarais et al. |
| 2010/0284927 A1 | 11/2010 | Lu et al. |
| 2010/0286684 A1 | 11/2010 | Hata et al. |
| 2010/0298821 A1 | 11/2010 | Garbagnati |

(56) References Cited

U.S. PATENT DOCUMENTS

| | | |
|---|---|---|
| 2010/0305036 A1 | 12/2010 | Barnes |
| 2010/0312141 A1 | 12/2010 | Keast et al. |
| 2010/0324472 A1 | 12/2010 | Wulfman |
| 2011/0009750 A1 | 1/2011 | Taylor et al. |
| 2011/0021976 A1 | 1/2011 | Li et al. |
| 2011/0034832 A1 | 2/2011 | Cioanta et al. |
| 2011/0040324 A1 | 2/2011 | McCarthy et al. |
| 2011/0044942 A1 | 2/2011 | Puri et al. |
| 2011/0060324 A1 | 3/2011 | Wu et al. |
| 2011/0071400 A1 | 3/2011 | Hastings et al. |
| 2011/0071401 A1 | 3/2011 | Hastings et al. |
| 2011/0077498 A1 | 3/2011 | McDaniel |
| 2011/0092781 A1 | 4/2011 | Gertner |
| 2011/0092880 A1 | 4/2011 | Gertner |
| 2011/0104061 A1 | 5/2011 | Seward |
| 2011/0112400 A1 | 5/2011 | Emery et al. |
| 2011/0118600 A1 | 5/2011 | Gertner |
| 2011/0118726 A1 | 5/2011 | De La Rama et al. |
| 2011/0130708 A1 | 6/2011 | Perry et al. |
| 2011/0137155 A1 | 6/2011 | Weber et al. |
| 2011/0144479 A1 | 6/2011 | Hastings et al. |
| 2011/0146673 A1 | 6/2011 | Keast et al. |
| 2011/0166499 A1 | 7/2011 | Demarais et al. |
| 2011/0178570 A1 | 7/2011 | Demarais |
| 2011/0200171 A1 | 8/2011 | Beetel et al. |
| 2011/0202098 A1 | 8/2011 | Demarais et al. |
| 2011/0207758 A1 | 8/2011 | Sobotka et al. |
| 2011/0208096 A1 | 8/2011 | Demarais et al. |
| 2011/0257523 A1 | 10/2011 | Hastings et al. |
| 2011/0257564 A1 | 10/2011 | Demarais et al. |
| 2011/0257622 A1 | 10/2011 | Salahieh et al. |
| 2011/0257641 A1 | 10/2011 | Hastings et al. |
| 2011/0257642 A1 | 10/2011 | Griggs, III |
| 2011/0263921 A1 | 10/2011 | Vrba et al. |
| 2011/0264011 A1 | 10/2011 | Wu et al. |
| 2011/0264075 A1 | 10/2011 | Leung et al. |
| 2011/0264086 A1 | 10/2011 | Ingle |
| 2011/0264116 A1 | 10/2011 | Kocur et al. |
| 2011/0270238 A1 | 11/2011 | Rizq et al. |
| 2011/0306851 A1 | 12/2011 | Wang |
| 2011/0307034 A1 | 12/2011 | Hastings et al. |
| 2011/0319809 A1 | 12/2011 | Smith |
| 2012/0029496 A1 | 2/2012 | Smith |
| 2012/0029500 A1 | 2/2012 | Jenson |
| 2012/0029505 A1 | 2/2012 | Jenson |
| 2012/0029509 A1 | 2/2012 | Smith |
| 2012/0029510 A1 | 2/2012 | Haverkost |
| 2012/0029511 A1 | 2/2012 | Smith et al. |
| 2012/0029512 A1 | 2/2012 | Willard et al. |
| 2012/0029513 A1 | 2/2012 | Smith et al. |
| 2012/0059241 A1 | 3/2012 | Hastings et al. |
| 2012/0059286 A1 | 3/2012 | Hastings et al. |
| 2012/0065506 A1 | 3/2012 | Smith |
| 2012/0065554 A1 | 3/2012 | Pikus |
| 2012/0095461 A1 | 4/2012 | Herscher et al. |
| 2012/0101413 A1 | 4/2012 | Beetel et al. |
| 2012/0101490 A1 | 4/2012 | Smith |
| 2012/0101538 A1 | 4/2012 | Ballakur et al. |
| 2012/0109021 A1 | 5/2012 | Hastings et al. |
| 2012/0116382 A1 | 5/2012 | Ku et al. |
| 2012/0116383 A1 | 5/2012 | Mauch et al. |
| 2012/0116392 A1 | 5/2012 | Willard |
| 2012/0116438 A1 | 5/2012 | Salahieh et al. |
| 2012/0116486 A1 | 5/2012 | Naga et al. |
| 2012/0123243 A1 | 5/2012 | Hastings |
| 2012/0123258 A1 | 5/2012 | Willard |
| 2012/0123261 A1 | 5/2012 | Jenson et al. |
| 2012/0123303 A1 | 5/2012 | Sogard et al. |
| 2012/0123406 A1 | 5/2012 | Edmunds et al. |
| 2012/0130289 A1 | 5/2012 | Demarais et al. |
| 2012/0130345 A1 | 5/2012 | Levin et al. |
| 2012/0130359 A1 | 5/2012 | Turovskiy |
| 2012/0130360 A1 | 5/2012 | Buckley et al. |
| 2012/0130362 A1 | 5/2012 | Hastings et al. |
| 2012/0130368 A1 | 5/2012 | Jenson |
| 2012/0130458 A1 | 5/2012 | Ryba et al. |
| 2012/0136344 A1 | 5/2012 | Buckley et al. |
| 2012/0136349 A1 | 5/2012 | Hastings |
| 2012/0136350 A1 | 5/2012 | Goshgarian et al. |
| 2012/0136417 A1 | 5/2012 | Buckley et al. |
| 2012/0136418 A1 | 5/2012 | Buckley et al. |
| 2012/0143181 A1 | 6/2012 | Demarais et al. |
| 2012/0143293 A1 | 6/2012 | Mauch et al. |
| 2012/0143294 A1 | 6/2012 | Clark et al. |
| 2012/0150267 A1 | 6/2012 | Buckley et al. |
| 2012/0157986 A1 | 6/2012 | Stone et al. |
| 2012/0157987 A1 | 6/2012 | Steinke et al. |
| 2012/0157988 A1 | 6/2012 | Stone et al. |
| 2012/0157989 A1 | 6/2012 | Stone et al. |
| 2012/0157992 A1 | 6/2012 | Smith et al. |
| 2012/0157993 A1 | 6/2012 | Jenson et al. |
| 2012/0158101 A1 | 6/2012 | Stone et al. |
| 2012/0158104 A1 | 6/2012 | Huynh et al. |
| 2012/0172837 A1 | 7/2012 | Demarais et al. |
| 2012/0172870 A1 | 7/2012 | Jenson et al. |
| 2012/0184952 A1 | 7/2012 | Jenson et al. |
| 2012/0197198 A1 | 8/2012 | Demarais et al. |
| 2012/0197252 A1 | 8/2012 | Deem et al. |
| 2012/0232409 A1 | 9/2012 | Stahmann et al. |
| 2012/0265066 A1 | 10/2012 | Crow et al. |
| 2012/0265198 A1 | 10/2012 | Crow et al. |
| 2013/0012844 A1 | 1/2013 | Demarais et al. |
| 2013/0012866 A1 | 1/2013 | Deem et al. |
| 2013/0012867 A1 | 1/2013 | Demarais et al. |
| 2013/0013024 A1 | 1/2013 | Levin et al. |
| 2013/0023865 A1 | 1/2013 | Steinke et al. |
| 2013/0035681 A1 | 2/2013 | Subramanaim et al. |
| 2013/0066316 A1 | 3/2013 | Steinke et al. |
| 2013/0085489 A1 | 4/2013 | Fain et al. |
| 2013/0090563 A1 | 4/2013 | Weber |
| 2013/0090578 A1 | 4/2013 | Smith et al. |
| 2013/0090647 A1 | 4/2013 | Smith |
| 2013/0090649 A1 | 4/2013 | Smith et al. |
| 2013/0090650 A1 | 4/2013 | Jenson et al. |
| 2013/0090651 A1 | 4/2013 | Smith |
| 2013/0090652 A1 | 4/2013 | Jenson |
| 2013/0096550 A1 | 4/2013 | Hill |
| 2013/0096553 A1 | 4/2013 | Hill et al. |
| 2013/0096554 A1 | 4/2013 | Groff et al. |
| 2013/0096604 A1 | 4/2013 | Hanson et al. |
| 2013/0110106 A1 | 5/2013 | Richardson |
| 2013/0116687 A1 | 5/2013 | Willard |
| 2013/0165764 A1 | 6/2013 | Scheuermann et al. |
| 2013/0165844 A1 | 6/2013 | Shuros et al. |
| 2013/0165916 A1 | 6/2013 | Mathur et al. |
| 2013/0165917 A1 | 6/2013 | Mathur et al. |
| 2013/0165920 A1 | 6/2013 | Weber et al. |
| 2013/0165923 A1 | 6/2013 | Mathur et al. |
| 2013/0165924 A1 | 6/2013 | Mathur et al. |
| 2013/0165925 A1 | 6/2013 | Mathur et al. |
| 2013/0165926 A1 | 6/2013 | Mathur et al. |
| 2013/0165990 A1 | 6/2013 | Mathur et al. |
| 2013/0172815 A1 | 7/2013 | Perry et al. |
| 2013/0172872 A1 | 7/2013 | Subramaniam et al. |
| 2013/0172877 A1 | 7/2013 | Subramaniam et al. |
| 2013/0172878 A1 | 7/2013 | Smith |
| 2013/0172879 A1 | 7/2013 | Sutermeister |
| 2013/0172880 A1 | 7/2013 | Willard |
| 2013/0172881 A1 | 7/2013 | Hill et al. |

FOREIGN PATENT DOCUMENTS

| | | | |
|---|---|---|---|
| EP | 1053720 | A1 | 11/2000 |
| EP | 1180004 | A1 | 2/2002 |
| EP | 1335677 | B1 | 8/2003 |
| EP | 1874211 | A2 | 1/2008 |
| EP | 1906853 | A2 | 4/2008 |
| EP | 1961394 | | 8/2008 |
| EP | 1961394 | A2 | 8/2008 |
| EP | 1620156 | B1 | 7/2009 |
| EP | 2076193 | A2 | 7/2009 |
| EP | 2091455 | A2 | 8/2009 |
| EP | 2197533 | A1 | 6/2010 |
| EP | 2208506 | A1 | 7/2010 |

(56) References Cited

FOREIGN PATENT DOCUMENTS

| | | |
|---|---|---|
| EP | 1579889 B1 | 8/2010 |
| EP | 2092957 B1 | 1/2011 |
| EP | 2349044 A1 | 8/2011 |
| EP | 2027882 B1 | 10/2011 |
| EP | 2378956 A2 | 10/2011 |
| EP | 2037840 B1 | 12/2011 |
| EP | 2204134 B1 | 4/2012 |
| EP | 2320821 B1 | 10/2012 |
| GB | 2456301 A | 7/2009 |
| WO | 9858588 A1 | 12/1998 |
| WO | 9900060 A1 | 1/1999 |
| WO | 0047118 A1 | 8/2000 |
| WO | 0170144 A1 | 9/2001 |
| WO | 03026525 A1 | 4/2003 |
| WO | 2004100813 A2 | 11/2004 |
| WO | 2004110258 A2 | 12/2004 |
| WO | 2006009856 A1 | 1/2006 |
| WO | 2006022790 A1 | 3/2006 |
| WO | 2006041881 A2 | 4/2006 |
| WO | 2006105121 A2 | 10/2006 |
| WO | 2007035537 A2 | 3/2007 |
| WO | 2007078997 A2 | 7/2007 |
| WO | 2007086965 A2 | 8/2007 |
| WO | 2007103879 A2 | 9/2007 |
| WO | 2007103881 A2 | 9/2007 |
| WO | 2007121309 A2 | 10/2007 |
| WO | 2007146834 A2 | 12/2007 |
| WO | 2008003058 A2 | 1/2008 |
| WO | 2008014465 A2 | 1/2008 |
| WO | 2008061150 A2 | 5/2008 |
| WO | 2008061152 A2 | 5/2008 |
| WO | 2008070413 A2 | 6/2008 |
| WO | 2009121017 A1 | 10/2009 |
| WO | 2010067360 A2 | 6/2010 |
| WO | 2010078175 A1 | 7/2010 |
| WO | 2010102310 A2 | 9/2010 |
| WO | 2010129661 A1 | 11/2010 |
| WO | 2011005901 A2 | 1/2011 |
| WO | 2011053757 A1 | 5/2011 |
| WO | 2011053772 A1 | 5/2011 |
| WO | 2011091069 A1 | 7/2011 |
| WO | 2011130005 A2 | 10/2011 |
| WO | 2011130534 A2 | 10/2011 |
| WO | 2011139589 A2 | 11/2011 |
| WO | 2012019156 A1 | 2/2012 |
| WO | 2013049601 A2 | 4/2013 |

OTHER PUBLICATIONS

"IntraLuminal: Products," IntraLuminal Therapeutics, Inc., 2003, p. 1-9.
"Laser Catheter to Aid Coronary Surgery," TechTalk: MIT, Jan. 9, 1991, p. 1-4.
"Optical Coherence Tomography: Advantages of OCT," LightLab Imaging Technology.
"Optical Coherence Tomography: Image Gallery Cardiovascular Procedures," LightLab Imaging Technology.
"Optical Coherence Tomography: LightLab Imaging Starts US Cardiology Clinical Investigations," LightLab Imaging Technology, 2002.
"Optical Coherence Tomography: LightLab Sees Bright Prospects for Cardiac Application of OCT Technology," LightLab Imaging Technology, 2001, vol. 27, No. 35.
"Optical Coherence Tomography: What is OCT?," LightLab Imaging Technology.
"Optical Coherence Tomography: Why Use OCT?," LightLab Imaging Technology.
"Products—Functional Measurement," VOLCANO Functional Measurement Products US, Mar. 24, 2003, p. 1-2.
Brown et al., "Radiofrequency capacitive heaters: the effect of coupling medium resistivity on power absorption along a mouse leg," Physics in Medicine and Biology, 1993, p. 1-12, vol. 38.
Carrington, "Future of CVI: It's all about plaque: Identification of vulnerable lesions, not 'rusty pipes,' could become cornerstone of preventive cardiology," Diagnostic Imaging, 2001, p. 1-8.
Chen et al., "Percutaneous pulmonary artery denervation completely abolishes experimental pulmonary arterial hypertension in vivo," EuroIntervention, 2013, p. 1-8.
Cimino, "Preventing plaque attack," Mass High Tech, 2001, p. 1-2.
Dahm et al., "Relation of Degree of Laser Debulking of In-Stent Restenosis as a Predictor of Restenosis Rate," The American Journal of Cardiology, 2002, p. 68-70, vol. 90.
De Korte et al., "Characterization of Plaque Components With Intravascular Ultrasound Elastography in Human Femoral and Coronary Arteries In Vitro," Circulation, Aug. 8, 2000, p. 617-623.
Durney et al., "Radiofrequency Radiation Dosimetry Handbook," Oct. 1986, p. 1-2, Fourth Edition.
Durney et al., "Radiofrequency Radiation Dosimetry Handbook: Contents," Oct. 1986, p. 1-5, Fourth Edition.
Fournier-Desseux et al., "Assessment of 1-lead and 2-lead electrode patterns in electrical impedance endotomography," Physiological Measurement, 2005, p. 337-349. Vo. 26, Institute of Physics Publishing.
Fram et al., "Feasibility of Radiofrequency Powered, Thermal Balloon Ablation of Atrioventricular Bypass Tracts Via the Coronary Sinus: In Vivo Canine Studies," PACE, Aug. 1995, p. 1518-1530, vol. 18.
Fram et al., "Low Pressure Radiofrequency Balloon Angioplasty: Evaluation in Porcine Peripheral Arteries," JACC, 1993, p. 1512-1521, vol. 21, No. 6, American College of Cardiology.
Fujimori et al., "Significant Prevention of In-Stent Restenosis by Evans Blue in Patients with Acute Myocardial Infarction," American Heart Association, 2002.
Fujita et al., "Sarpogrelate, an Antagonist of 5-HT(2A) Receptor, Treatment Reduces Restenosis After Coronary Stenting," American Heart Association, 2002.
Gabriel, "Appendix A: Experimental Data," 1999, p. 1-21.
Gabriel, "Appendix C: Modeling the frequency dependence of the dielectric properties to a 4 dispersions spectrum," p. 1-6.
Gregory et al., "Liquid Core Light Guide for Laser Angioplasty," The Journal of Quantum Electronics, Dec. 1990, p. 2289-2296, vol. 26, No. 12.
Kaplan et al., "Healing after Arterial Dilatation with Radiofrequency Thermal and Nonthermal Balloon Angioplasty Sytems," Journal of Investigative Surgery, 1993, p. 33-52, vol. 6.
Kolata, "New Studies Question Value of Opening Arteries," The New York Times, Mar. 21, 2004, p. 1-5.
Konings et al., "Development of an Intravascular Impedance Catheter for Detection of Fatty Lesions in Arteries," IEEE Transactions on Medical Imaging, Aug. 1997, p. 439-446, vol. 16, No. 4.
Kurtz et al., "Lamellar Refractive Surgery with Scanned Intrastromal Picosecond and Femtosecond Laser Pulses in Animal Eyes," Journal of Refractive Surgery, Sep./Oct. 1998, p. 541-548.
Lee et al., "Thermal Compression and Molding of Atherosclerotic Vascular Tissue With Use of Radiofrequency Energy: Implications for Radiofrequency Balloon Angioplasty," JACC, 1989, p. 1167-1175, vol. 13, No. 5, American College of Cardiology.
Lima et al., "Efficacy and Safety of Oral Sirolimus to Treat and Prevent In-Stent Restenosis: A Pilot Study Results," American Heart Association, 2002, p. 2929.
Lima et al., "Systemic Immunosuppression Inhibits In-Stent Coronary Intimal Proliferation in Renal Transplant Patients," American Heart Association, 2002, p. 2928.
Morice et al., "A Randomized Comparison of a Sirolimus-Eluting Stent With a Standard Stent for Coronary Revascularization," The New England Journal of Medicine, Jun. 6, 2012, p. 1773-1780, vol. 346, No. 23.
Muller-Leisse et al., "Effectiveness and Safety of Ultrasonic Atherosclerotic Plaque Ablation: In Vitro Investigation," CardioVascular and Interventional Radiology, 1993, p. 303-307, vol. 16.
Nair et al., "Regularized Autoregressive Analysis of Intravascular Ultrasound Backscatter: Improvement in Spatial Accuracy of Tissue Maps," IEEE Transactions on Ultrasonics, Apr. 2004, p. 420-431, vol. 51, No. 4.

(56) References Cited

OTHER PUBLICATIONS

Popma et al., "Percutaneous Coronary and Valvular Intervention," p. 1364-1405.
Resar et al., "Endoluminal Sealing of Vascular Wall Disruptions With Radiofrequency-Heated Balloon Angioplasty," Catheterization and Cardiovascular Diagnosis, 1993, p. 161-167, vol. 29.
Romer et al., "Histopathology of Human Coronary Atherosclerosis by Quantifying Its Chemical Composition With Raman Spectroscopy," Circulation, 1998, p. 878-885, vol. 97.
Schauerte et al., "Catheter Ablation of Cardiac Autonomic Nerves for Prevention of Vagal Atrial Fibrillation," Circulation, 2000, p. 2774-2780, vol. 102.
Scheller et al., "Intracoronary Paclitaxel Added to Contrast Media Inhibits In-Stent Restenosis of Porcine Coronary Arteries," American Heart Association, 2002, p. 2227.
Scheller et al., "Potential solutions to the current problem: coated balloon," EuroIntervention, 2008, p. C63-C66, vol. 4 (Supplement C).
Shaffer, "Scientific basis of laser energy," Clinics in Sports Medicine, 2002, p. 585-598, vol. 21.
Shmatukha et al., "MRI temperature mapping during thermal balloon angioplasty," Physics in Medicine and Biology, 2006, p. N163-N171, vol. 51.
Slager et al., "Vaporization of Atherosclerotic Plaques by Spark Erosion," J Am Coll Cardiol, 1985, p. 21-25.
Stiles et al., "Simulated Characterization of Atherosclerotic Lesions in the Coronary Arteries by Measurement of Bioimpedance," IEEE Transactions on Biomedical Engineering, Jul. 2003, p. 916-921, vol. 50, No. 7.
Suselbeck et al., "In vivo intravascular electric impedance spectroscopy using a new catheter with integrated microelectrodes," Basic Res Cardiol, 2005, p. 28-34, vol. 100.
Suselbeck et al., "Intravascular electric impedance spectroscopy of atherosclerotic lesions using a new impedance catheter system," Basic Res Cardiol, 2005, p. 446-452, vol. 100.
Tepe et al., "Local Delivery of Paclitaxel to Inhibit Restenosis during Angioplasty of the Leg," The New England Journal of Medicine, 2008, p. 689-699, vol. 358.
CardioVascular Technologies Inc., "Heated Balloon Device Technology," 11 pages, 2008.
Strategic Business Development, Inc., "Thermal and Disruptive Angioplasty: A Physician's Guide," 8 pages, 1990.
Zhang et al., "Non-contact Radio-Frequency Ablation for Obtaining Deeper Lesions," IEEE Transaction on Biomedical Engineering, vol. 50, No. 2, 6 pages, Feb. 2003.
Lazebnik et al., "Tissue Strain Analytics Virtual Touch Tissue Imaging and Qualification," Siemens Whitepaper, Oct. 2008, 7 pages.
Han et al., "Third-Generation Cryosurgery for Primary and Recurrent Prostate Caner," BJU International, vol. 93, pp. 14-18.
Zhou et al., "Mechanism Research of Ciyoanalgesia," Forefront Publishing Group, 1995.
Florete, "Cryoblative Procedure for Back Pain," Jacksonville Medicine, Oct. 1998, 10 pages.
Stevenson, "Irrigated RF Ablation: Power Titration and Fluid Management for Optimal Safety Efficacy," 2005, 4 pages.
Giliatt et al., "The Cause of Nerve Damage in Acute Compression," Trans Am Neurol Assoc, 1974: 99; 71-4.
Omura et al., "A Mild Acute Compression Induces Neurapraxia in Rat Sciatic Nerve," The International Journal of Neuroscience, vol. 114 (12), pp. 1561-1572.
Baun, "Interaction with Soft Tissue," Principles of General & Vascular Sonography, Chapter 2, pp. 23-24, Before Mar. 2012.
Blue Cross Blue Shield Medicaly Policy, "Surgery Section—MRI-Guided Focused Ultrasound (MRgFUS) for the Treatment of Uterine Fibroids and Other Tumors," 2005, 5 pages.
Gentry et al., "Combines 3D Intracardiac Echo and Ultrasound Ablation," Medical Imaging 2003: Ultrasonic and Signal Processing, vol. 5035, 2003, pp. 166-173.
Lafon et al., "Optmizing the Shape of Ultrasound Transducers for Interstitial Thermal Ablations," MEd Phys. Mar. 2002; 29(3): 290-7 (abstract only).
G. Ter Haar, "Ultrasound Focal Beam Surgery," Ultrasound in Med. & Biol., 1995, vol. 21, No. 9, pp. 1089-1100.
Seip et al., "Transurethral High Intensity Focused Ultrasound: Catheter Based Prototypes and Experimental Results," IEEE Ultrasonics Symposium Proceeding, 2000, 4 pages.
Toytman et al., "Tissue Dissection with Ultrafast Laser Using Extended and Multiple Foci," SPIE Proceeding, Optical Interactions with Tissues and Cells XXI, vol. 7562, 2010, 10 pages.
Zhoue et al., "Non-Thermal Ablation of Rabbit Liver VX2 Tumore by Pulsed High Intensity Focused Ultrasound Contrast Agent: Pathological Characteristics," World Journal of Gastroenterology, vol. 14(43), Nov. 21, 2008, pp. 6743-6747.
Zhang et al., "Noncontact Radio-Frequency Ablation for Obtaining Deeper Lesions," IEEE Transactions on Biomedical Engineering, vol. 50, No. 2, Feb. 2003, pp. 218-223.
US 8,398,630, 03/2013, Demarais et al. (withdrawn)

\* cited by examiner

NERVE MODULATION SYSTEM HAVING HELICAL GUIDE

CROSS-REFERENCE TO RELATED APPLICATIONS

This application claims priority under 35 U.S.C. §119 to U.S. Provisional Application Ser. No. 61/510,900, filed Jul. 22, 2011, the entirety of which is incorporated herein by reference.

TECHNICAL FIELD

The present invention relates to methods and apparatus for modulation of nerves through the walls of blood vessels. Such modulation may include ablation of nerve tissue or other destructive modulation technique.

BACKGROUND

Certain treatments require the temporary or permanent interruption or modification of select nerve function. One example treatment is renal nerve ablation which is sometimes used to treat conditions related to congestive heart failure. The kidneys produce a sympathetic response to congestive heart failure, which, among other effects, increases the undesired retention of water and/or sodium. Ablating some of the nerves running to the kidneys reduces or eliminates this sympathetic function, which provides a corresponding reduction in the associated undesired symptoms.

Many nerves (and nervous tissue such as brain tissue), including renal nerves, run along the walls of or in close proximity to blood vessels and thus can be accessed intravascularly through the walls of the blood vessels. It is therefore desirable to provide for systems and methods for intravascular nerve modulation.

SUMMARY

Nerves that lie in proximity to blood vessels often run along the length of a section of a blood vessel. Nerves are difficult to image using standard imaging techniques such as radiography. Therefore, it is desirable to apply the ablation or other nerve modulation procedure at different radial locations on the vessel wall to achieve ablation around the complete circumference of the vessel wall. It is also desirable to apply the procedure at different longitudinal locations so as to avoid weakening or otherwise affecting the vessel wall along a single circumferential section. Embodiments therefore include a helical guide that provides simple and simultaneous radial and longitudinal movement of the electrode or other therapeutic element. This helical guide may be, for example a helical groove, rail or screw thread. The helical guide may extend for at least one complete circumferential rotation and in some embodiments for two or more circumferential rotations. As the electrode is pulled proximally, it is forced to follow the helical guide to alter, easily and predictably, its longitudinal and radial position.

Certain embodiments may include the following three elements, which are movable with respect to each other: a central shaft incorporating the helical guide, an elongate electrode carrying element and a sheath. In a summary of one example method of use, the elongate electrode carrying element and central shaft are loaded in the sheath, with an electrode (attached to the distal end of the carrying element) disposed at or near the distal end of the shaft. The system is moved to a desired location in a body vessel and the sheath is retracted, allowing the electrode and/or carrying element to expand radially such that the electrode can contact the wall of the vessel. The carrying element may be pulled proximally relative to the shaft and the electrode is activated intermittently or continuously. As the carrying element is pulled, the electrode is moved longitudinally and radially to provide a desired pattern. Power may be supplied to the electrode either through the carrying element or, in some cases, through the shaft. Once the therapy is completed, the shaft and the carrying element may be withdrawn into the sheath and the system may be withdrawn from the body.

Certain embodiments include centering elements such as expandable struts, legs, cages or helical elements or inflatable balloons that keep the shaft centered within the vessel during the procedure. These centering elements can be deployed by withdrawing the sheath or supplying an inflation fluid, as appropriate and may be collapsed by withdrawal into the sheath or evacuation of the inflation lumen. Certain of the centering elements are depicted in groups of two or three, but other numbers of centering elements (e.g. struts or legs) such as 4, 5, 6 or more are contemplated and may be used.

In certain embodiments, power may be supplied through the central shaft. The central shaft may be provided with a plurality of contact patches through which the power may be supplied to the electrode at certain pre-determined relative positions of the central shaft and carrying element. In this manner, the electrode may be activated automatically at pre-determined locations as the carrying element is being pulled proximally relative to the central shaft.

The term electrode as used herein refers of course to electrodes suitable for use radio-frequency ablation or modulation procedures, but it should not be considered as so limited. It is to be understood that where "electrode" is used, other elements, suitable for use in laser, ultrasonic, microwave, resistance heating or cryogenic procedures, are also intended. Further, electrode encompasses single path electrodes and electrodes that include a return path. Moreover, the methods and apparatuses described herein are readily adaptable for use with other therapeutic elements, such as irrigation, drug delivery, aspiration or atherectomy elements, and use with such other elements is so contemplated. The term modulation refers to ablation and other techniques that may alter the function of affect nerves.

The above summary of some example embodiments is not intended to describe each disclosed embodiment or every implementation of the invention.

BRIEF DESCRIPTION OF THE DRAWINGS

The invention may be more completely understood in consideration of the following detailed description of various embodiments in connection with the accompanying drawings, in which:

FIG. 9b is a cross-sectional view of the renal nerve modulation system of FIG. 9a.

FIG. 15b is a view of the distal portion of a component of the renal nerve modulation system of FIG. 15a.

Figure 1:
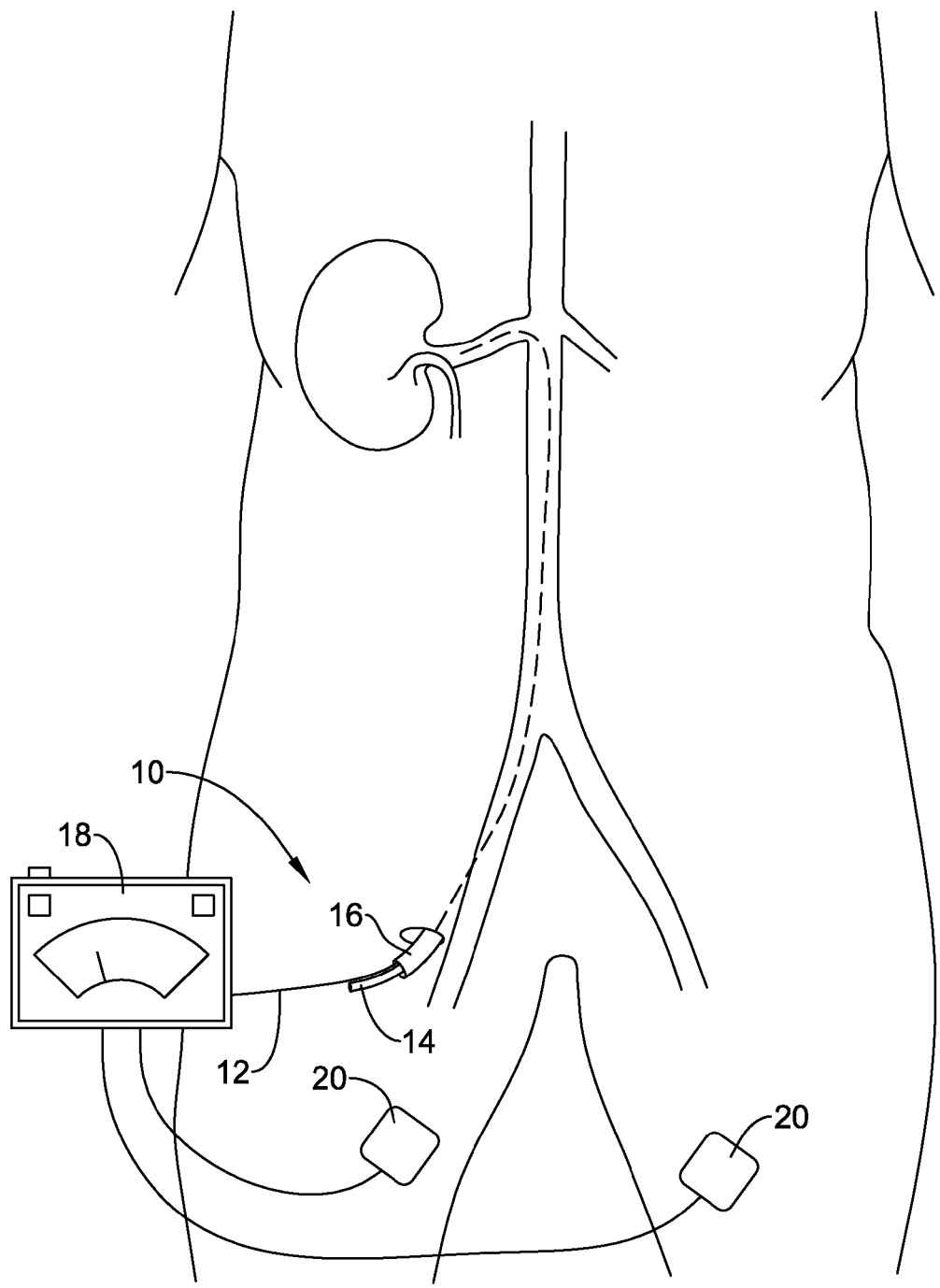
FIG. 1 is a schematic view illustrating a renal nerve modulation system in situ.

While the invention is amenable to various modifications and alternative forms, specifics thereof have been shown by way of example in the drawings and will be described in detail. It should be understood, however, that the intention is not to limit aspects of the invention to the particular embodiments described. On the contrary, the intention is to cover all modifications, equivalents, and alternatives falling within the spirit and scope of the invention.

DETAILED DESCRIPTION

For the following defined terms, these definitions shall be applied, unless a different definition is given in the claims or elsewhere in this specification.

All numeric values are herein assumed to be modified by the term "about", whether or not explicitly indicated. The term "about" generally refers to a range of numbers that one of skill in the art would consider equivalent to the recited value (i.e., having the same function or result). In many instances, the term "about" may be indicative as including numbers that are rounded to the nearest significant figure.

The recitation of numerical ranges by endpoints includes all numbers within that range (e.g., 1 to 5 includes 1, 1.5, 2, 2.75, 3, 3.80, 4, and 5).

Although some suitable dimensions, ranges and/or values pertaining to various components, features and/or specifications are disclosed, one of skill in the art, incited by the present disclosure, would understand desired dimensions, ranges and/or values may deviate from those expressly disclosed.

As used in this specification and the appended claims, the singular forms "a", "an", and "the" include plural referents unless the content clearly dictates otherwise. As used in this specification and the appended claims, the term "or" is generally employed in its sense including "and/or" unless the content clearly dictates otherwise.

The following detailed description should be read with reference to the drawings in which similar elements in different drawings are numbered the same. The detailed description and the drawings, which are not necessarily to scale, depict illustrative embodiments and are not intended to limit the scope of the invention. The illustrative embodiments depicted are intended only as exemplary. Selected features of any illustrative embodiment may be incorporated into an additional embodiment unless clearly stated to the contrary.

By way of a general introduction and orientation, FIG. 1 is a schematic view illustrating a renal nerve modulation system in situ. System 10 includes an elongate electrode carrying element 12 slidably disposed about a central shaft 14 and within a sheath 16, the details of which can be better seen in subsequent figures. Elongate electrode carrying element 12 is connected to a control and power element 18, which supplies the necessary electrical energy to activate the one or more electrodes at or near the distal end of the electrode carrying element 12. Return electrode patches 20 may be supplied on the legs or at another conventional location on the patient's body to complete the circuit.

The control and power element 18 may include monitoring elements to monitor parameters such as power, temperature, voltage, pulse size and/or shape and other suitable parameters as well as suitable controls for performing the desired procedure.

Figure 2:
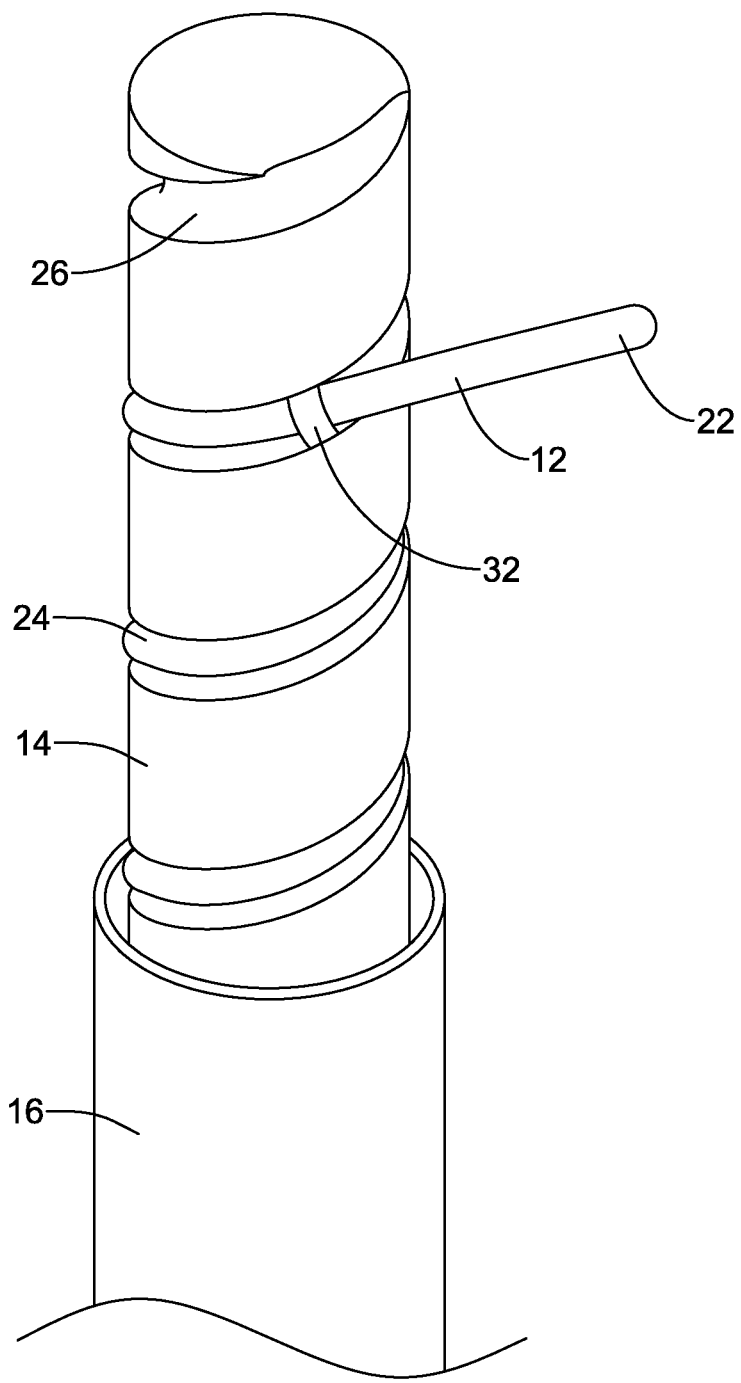
FIG. 2 illustrates the distal end of a renal nerve modulation system.

FIG. 2 illustrates the distal end of an example embodiment of a renal nerve modulation system. Elongate electrode carrying element 12 is disposed about a central shaft 14 and within a sheath 16. Elements 12, 14 and 16 are movable with respect to each other. Elongate electrode carrying element 12 includes an electrode 22 attached to a conductor 24, and the conductor 24 and a base portion 32 of the electrode are disposed in a groove 26 of the central shaft 14. When conductor 24 is pulled proximally relative to central shaft 14, the electrode 22 is likewise shifted proximally and is also rotated about the central shaft, following groove 26.

The groove 26 is a helical guide that may have a lead that is substantially greater than the pitch such that adjacent coils of the helical guide are spaced apart from one another. In some cases, the lead may be two, three, four or more times the pitch. The pitch of the groove may be approximately the same width of as the electrode or may in some cases be wider than the width of the electrode.

Figure 3A:
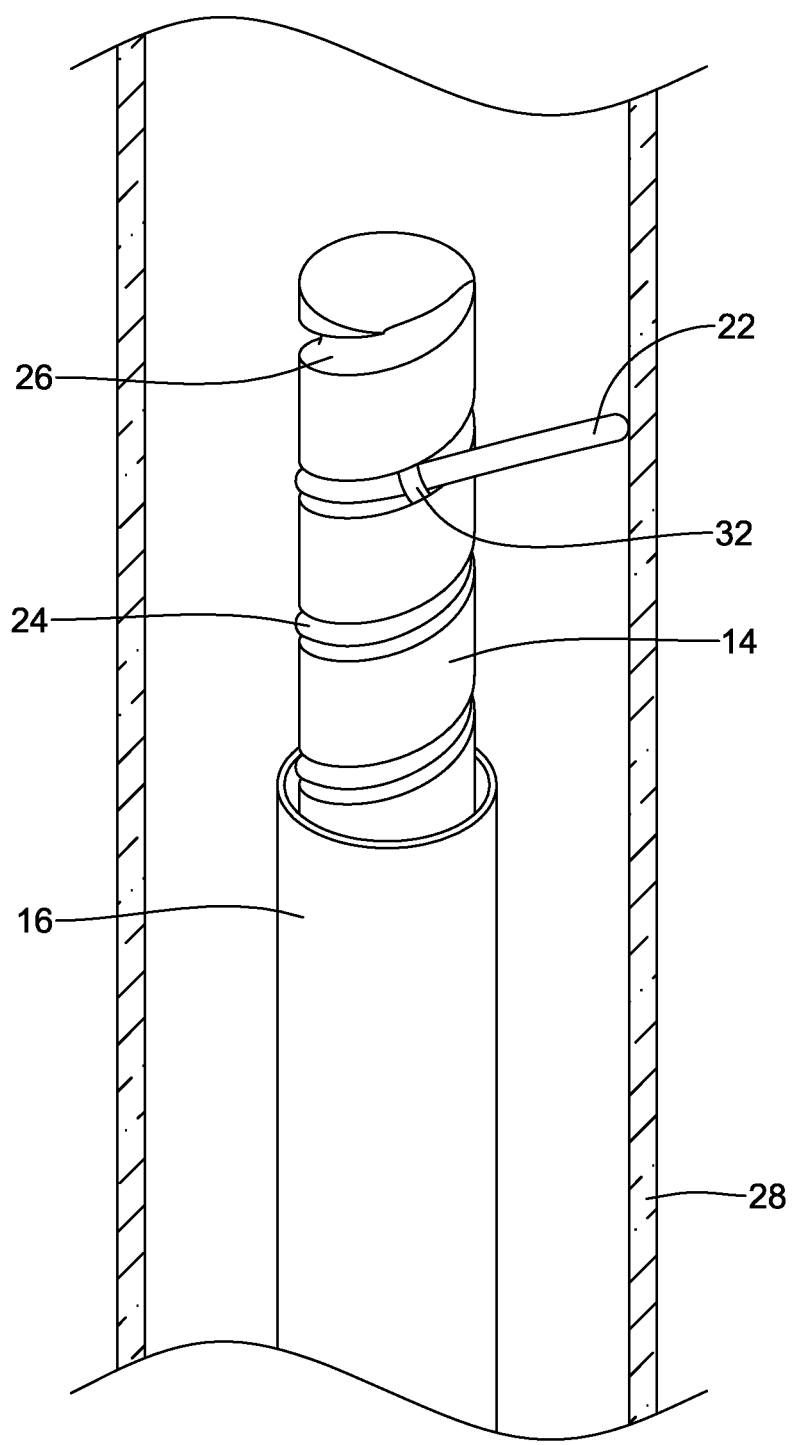
FIG. 3a through 3d illustrate the distal end of the renal nerve ablation system of FIG. 2 in situ with the electrode at various positions.
Figure 3B:
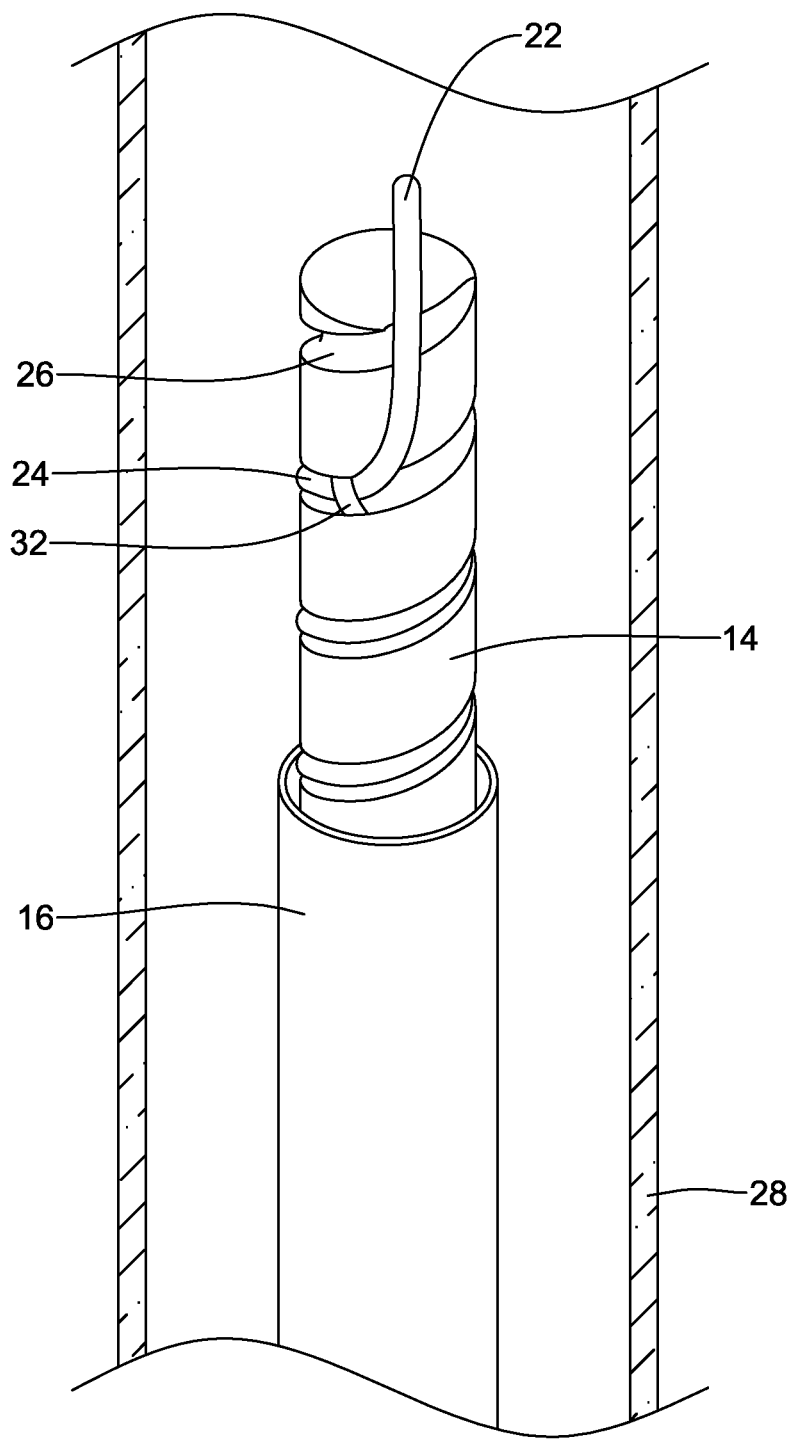
Figure 3C:
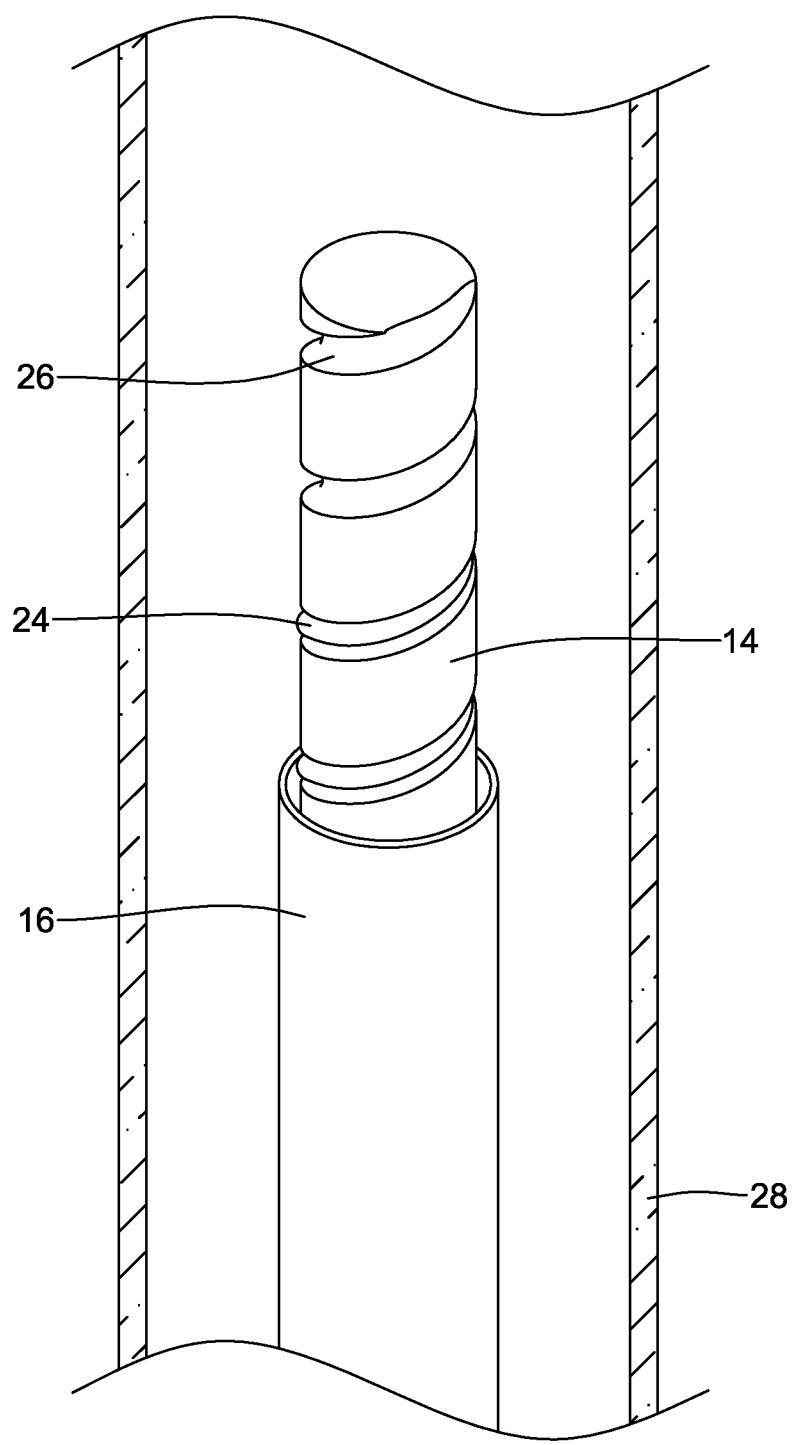
Figure 3D:
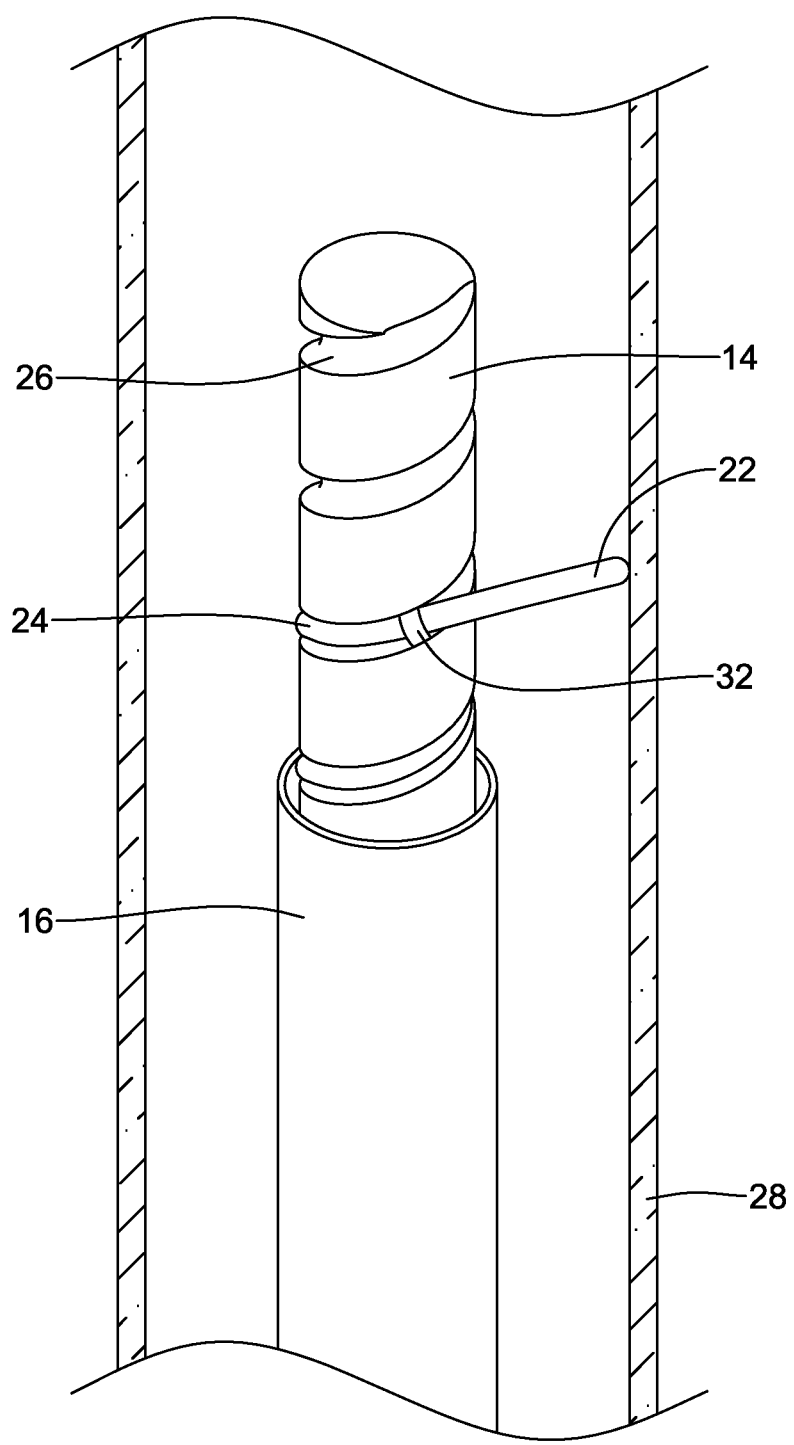

FIGS. 3A through 3D illustrate this rotational and radial movement of the electrode as it moves proximally. In FIG. 3A, the electrode 22 is pre-loaded at a distal end of the shaft 14. As the electrode 22 is pulled proximally by conductor 24, it rotates about shaft 14 and its distal end contacts different radial locations of the vessel wall 28 at different longitudinal locations, tracing a helical contact path along the vessel wall. The electrode 22 may be selectively activated at 3, 4, 5, 6, 7, 8 or more locations along this contact path or maybe continuously or intermittently activated while tracing this path.

In addition, FIGS. 3A-3D illustrate the distal end of a renal nerve modulation system in situ. Such a system may be advanced to the desired location within the blood vessel with the elongated electrode carrying elements 12 and the central shaft 14 within the sheath 16. It is contemplated that the electrode 22 is a resilient member that may be compressed within the sheath 16 during delivery to be expanded when sheath 16 is retracted.

Figure 4A:
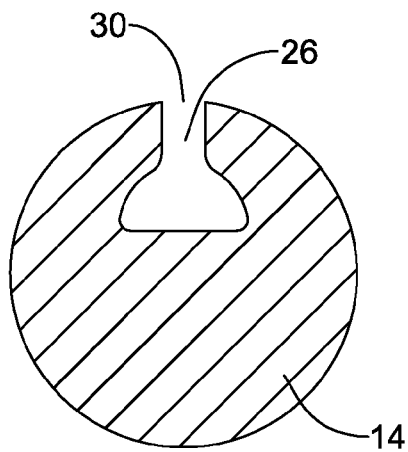
FIGS. 4a and 4b are cross-sectional views of various central shafts that may be used, for example, with the embodiment of FIG. 2 as well as other embodiments.
Figure 4B:
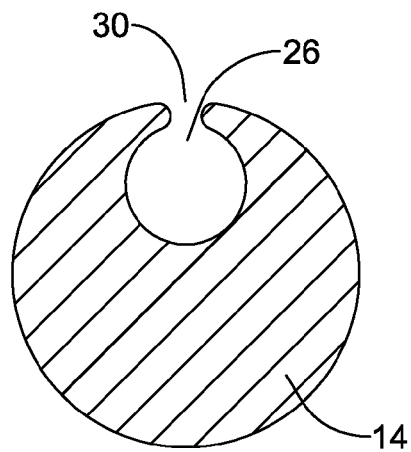
Figure 4C:
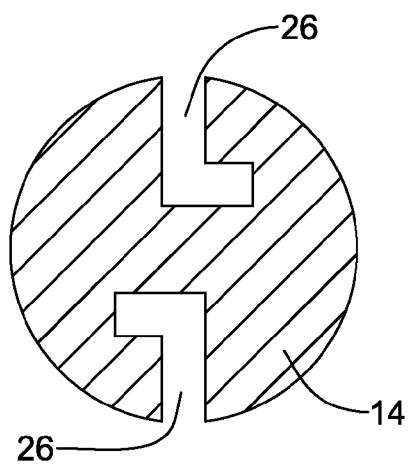
FIG. 4c is a cross-sectional view of a central shaft of a renal nerve modulation system.
Figure 4D:
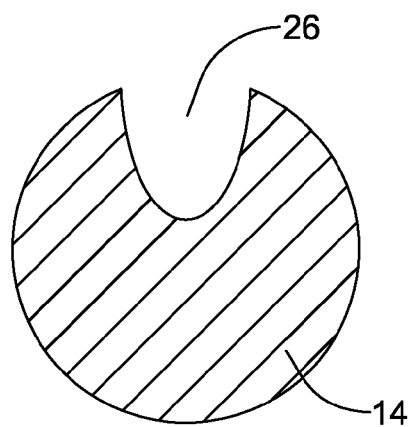
FIG. 4d is a cross-section view of a central shaft of a renal nerve modulation system.

FIGS. 4A and 4B illustrate example cross-sectional shapes of central shaft 14 and groove 26. Groove 26 may have a relatively narrow mouth 30 and widens as it deepens so as to retain the base portion 32 of the electrode 22. FIG. 4C is an example cross-sectional shape of central shaft 14 that illustrates embodiments of the system that may include two or more grooves in the shaft. FIG. 4D is an example cross-sectional shape of a shaft 14 of certain embodiments described below in which groove 26 functions merely as a guide and is not shaped to actively retain the base portion 32 of an electrode 22.

One such embodiment that may use a groove 26 similar to that illustrated in FIG. 4D is the embodiment shown in FIG. 11A, described below. Another embodiment that may use a groove such as that of FIG. 4D includes an elongate electrode carrying element wherein the conductor 24 has a coiled shape such that it can retain itself in the groove without the use of a base portion as described above. The electrode may be a straight distal section of such a conductor that expands to its deployed position and shape when released from the sheath. Of course, any conductor 24 in any embodiment may be biased into a coiled shape.

Figure 5A:
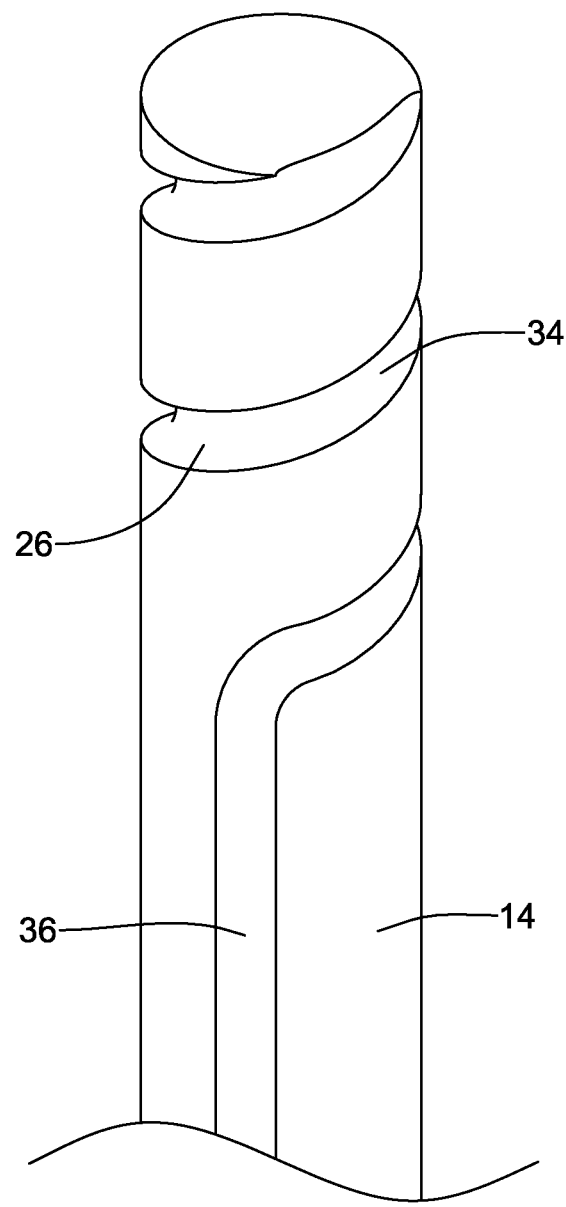
FIGS. 5a and 5b are views of the distal portion of central shafts that may be used, for example, with the embodiment of FIG. 2.

FIG. 5A illustrates the distal portion of a shaft 14 that may be used with the embodiment of FIG. 2. In this shaft, groove 26 may include a helical distal portion 34 and a straight proximal portion 36. The conductor 24 would of course follow through the helical path of the distal portion 34 and then extend along and within the straight proximal portion 36.

Figure 5B:
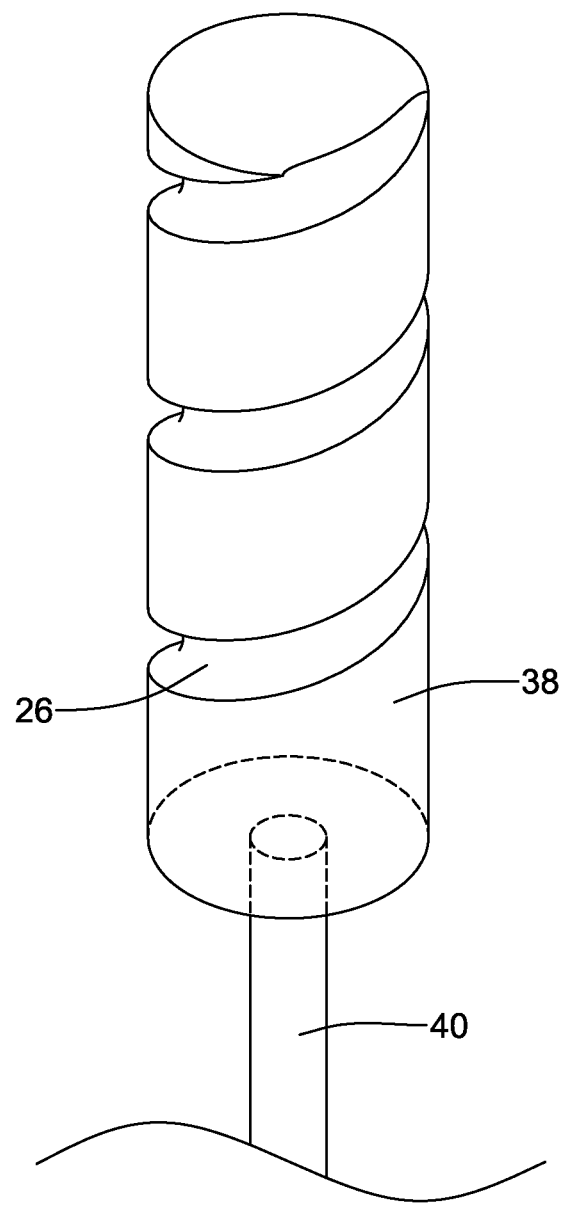

FIG. 5B illustrates the distal portion of another shaft 14 that may be used with the embodiment of FIG. 2. This shaft 14 includes the groove 26 in a distal section 38, which has a first, larger outer diameter. This distal section 38 extends from a narrower proximal section 40 that has a second smaller outer diameter. The outer diameter of section 40 may extend to the bottom of groove 26 or may be smaller. With this embodiment of shaft 14, the proximal portion of conductor 24 (not illustrated) may be a ribbon or wire as previously illustrated or may be cylindrical and hollow and disposed about the proximal section 40.

Figure 5C:
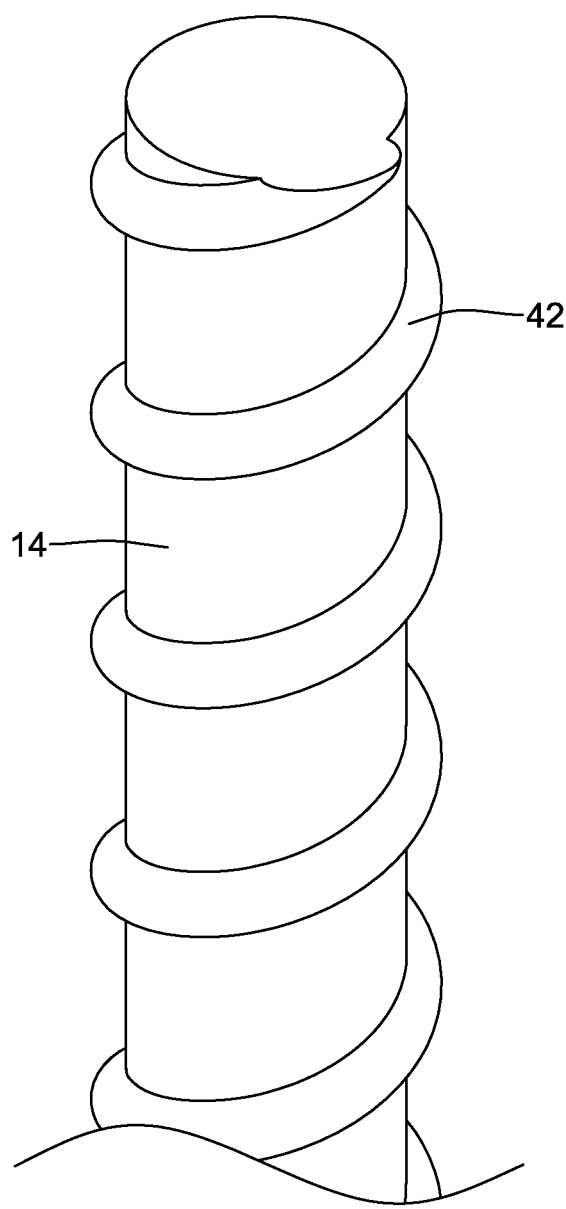
FIG. 5c is a view of the distal portion of a central shaft of a renal nerve modulation system.
Figure 6:
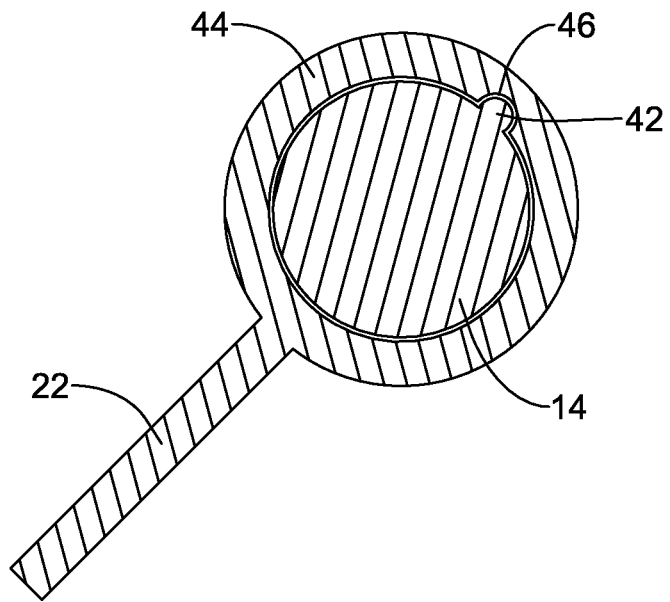
FIG. 6 is a cross-sectional view of a renal nerve modulation system that may use the shaft illustrated in FIG. 5c.
Figure 7:
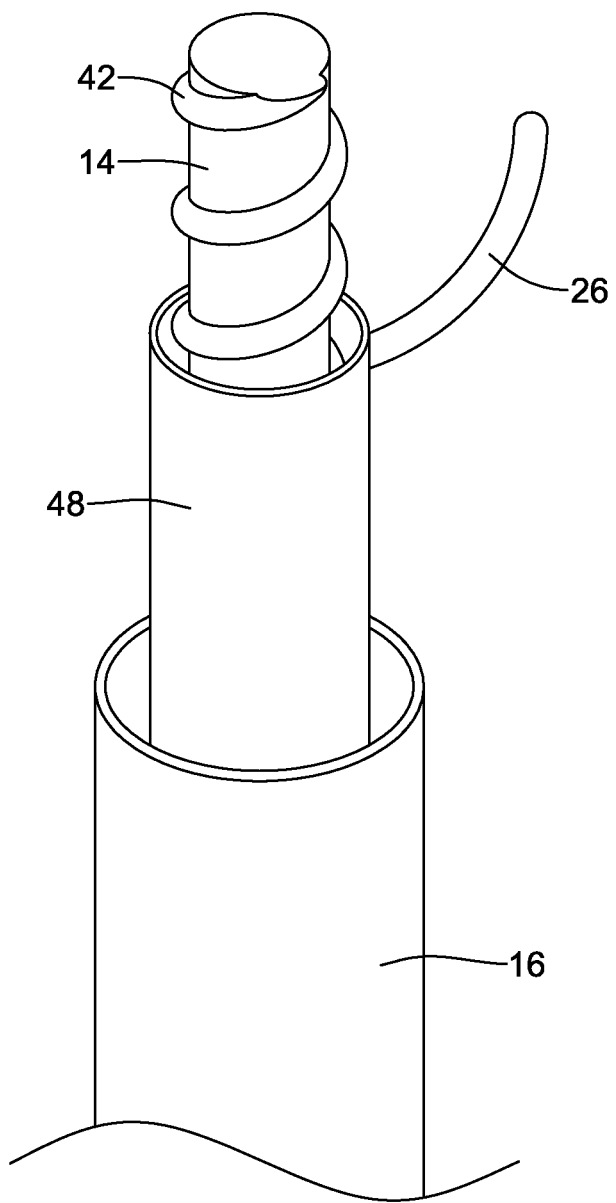
FIG. 7 is a cross-sectional view of a renal nerve modulation system that may use the shaft illustrated in FIG. 5c.

FIG. 5C illustrates the distal portion of an alternative shaft 14 in which the helical guiding element is a rail 42 rather than the previously illustrated groove 26. FIG. 6 is a diagrammatic cross-sectional view of the shaft 14 of FIG. 5C with an electrode 22 disposed thereon. Electrode 22 is attached to a collar 44 that has a notch 46 corresponding to the rail 42. Such an electrode 22 may be attached a ribbon conductor 24 as previously discussed or may be the distal portion of a conductor sheath 48 as illustrated in FIG. 7. In such a conductor sheath 48, either the notch 46 extends along the length of the sheath, or in other embodiments, the inner diameter of the sheath along the greater portion of its length may be greater than the outer radial extent of rail 42 and the notched portion has a relatively small extent.

Figure 5D:
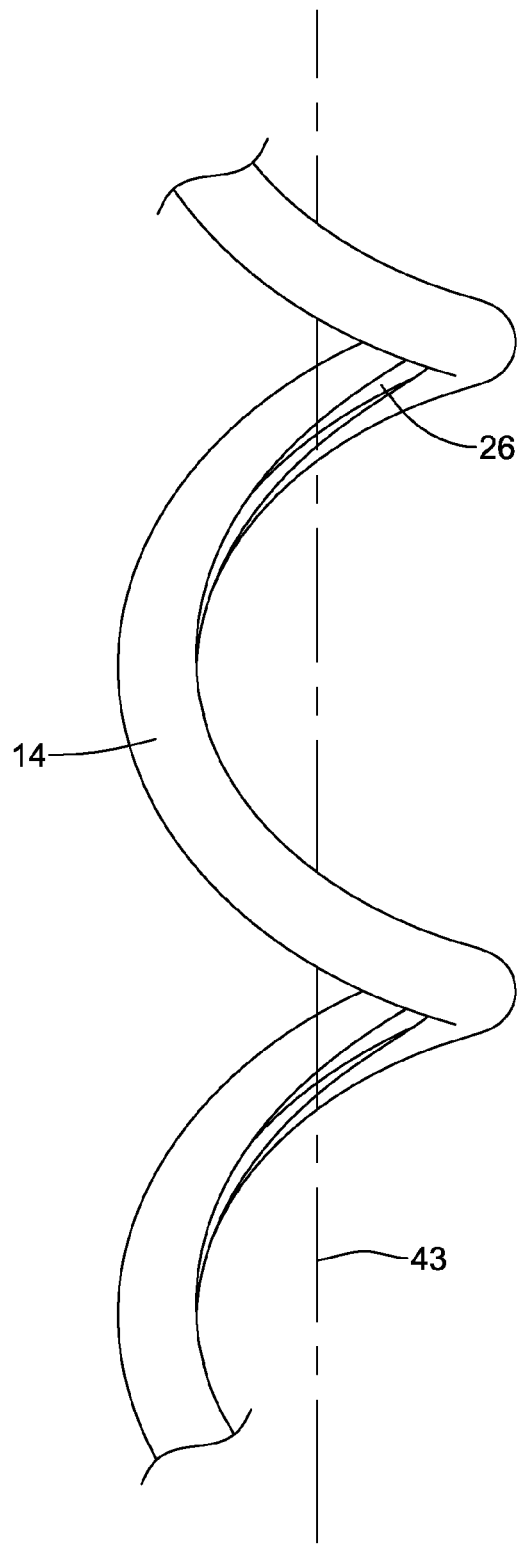
FIG. 5d is a view of the distal portion of a central shaft of a renal nerve modulation system.

FIG. 5D illustrates the distal portion of an alternate shaft 14 where the shaft is helical around a central axis 43. The groove 26 in this shaft faces towards the central axis 43. Here, the channel is straighter than a channel running along a straight shaft. An electrode such as ring electrode 70 of FIG. 11A may be used with such a shaft.

Figure 8A:
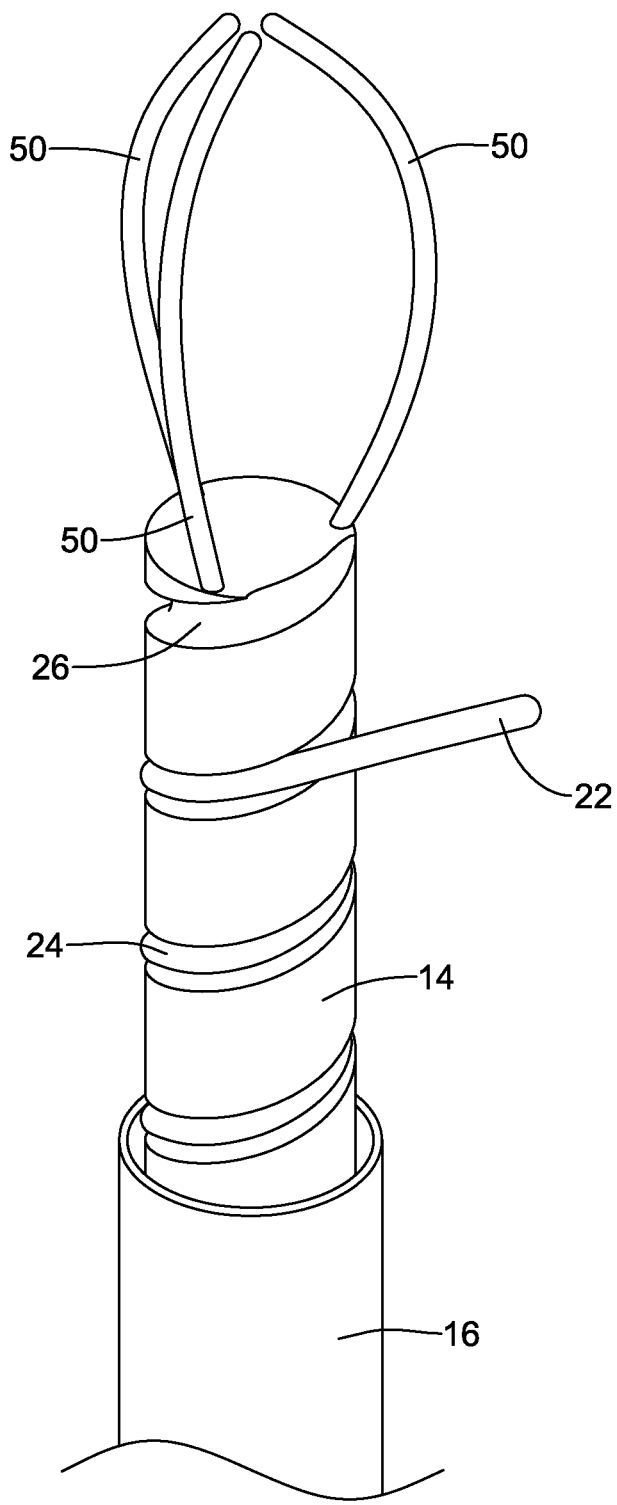
FIG. 8a is a view of the distal portion of a renal nerve modulation system having centering elements.

FIG. 8A illustrates the distal portion of an embodiment that includes distal centering elements 50. Centering elements 50 are resilient spring members that are readily compressible within the sheath 16 and which expand when the sheath 16 is retracted to contact the vessel wall to keep shaft 14 centrally located during operation of the system. Centering elements 50 have atraumatic distal ends and may include pads or other such elements. Centering elements 50 may have a curved shape as illustrated, and the distal ends may be free or may be joined together. Alternatively, centering elements may be straight or may have distal ends that are curved inwards.

Figure 8B:
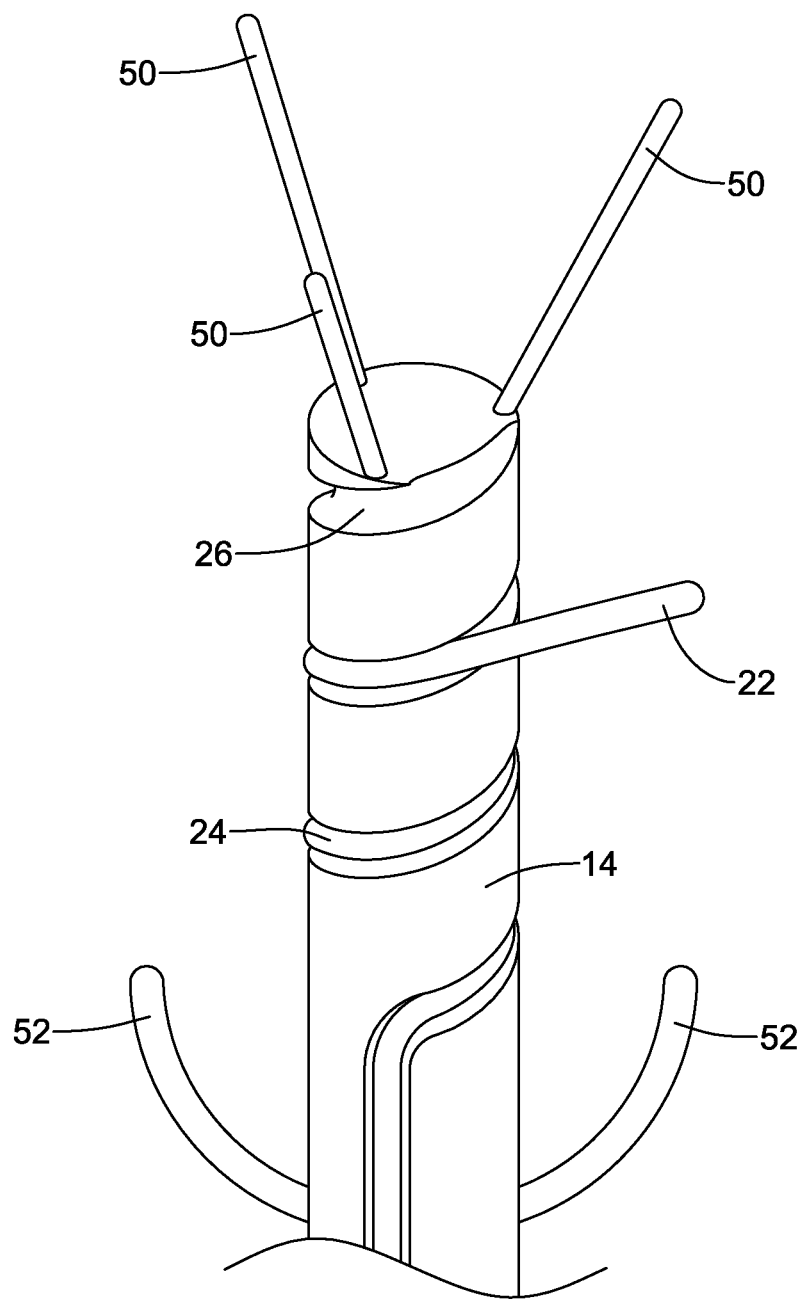
FIG. 8b is a view of the distal portion of a renal nerve modulation system having centering elements.

FIG. 8B illustrates the distal portion of an embodiment includes distal centering elements 50 and proximal centering elements 52. Centering elements 52 are likewise resiliently compressible members that expand outward upon the retraction of the sheath 16 (not illustrated) in like manner to centering elements 50. Centering elements 52 are illustrated as having free distal ends but may also have distal ends that curve back to join to shaft 14.

Figure 8C:
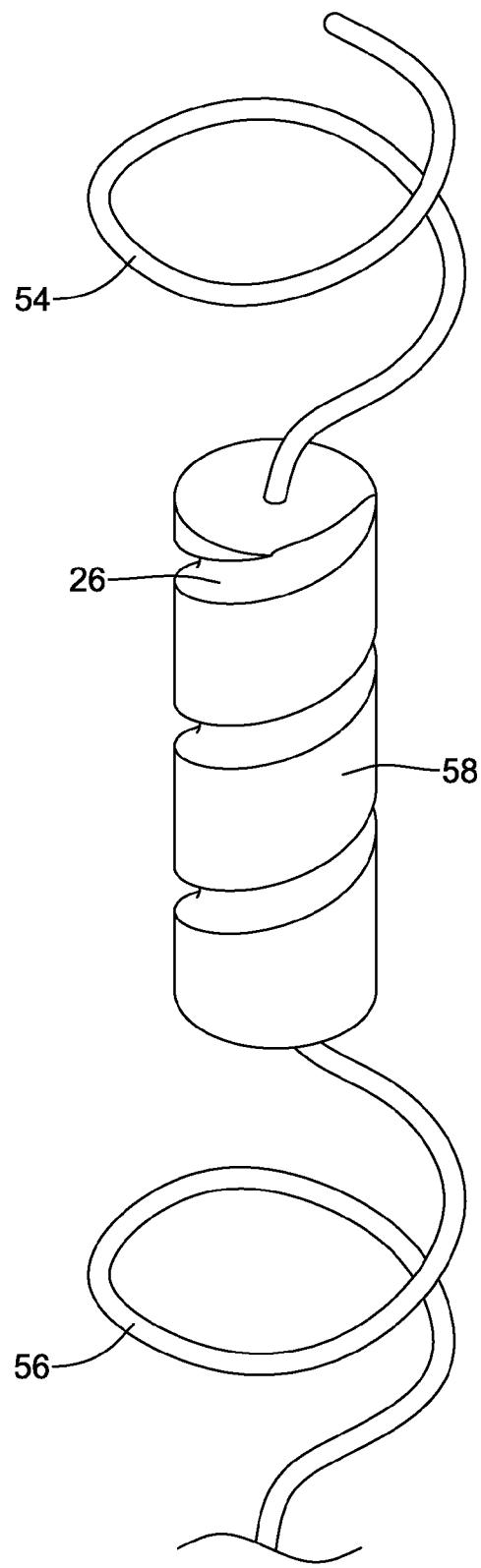
FIG. 8c is a view of the distal portion of a renal nerve modulation system having centering elements.

FIG. 8C illustrates the distal portion of an embodiment of that includes a helical distal centering element 54 and a proximal centering element 56. These elements are compressible within the sheath 16 and expand to their illustrated shape upon retraction of the sheath 16. Between centering elements 54 and 56 is a cylindrical shaft portion 58 having a groove 26 as discussed previously. Electrode 22 having a base portion 32 is slidably disposed in the groove 26 and is connected to a conductor 24 (not illustrated).

Figure 8D:
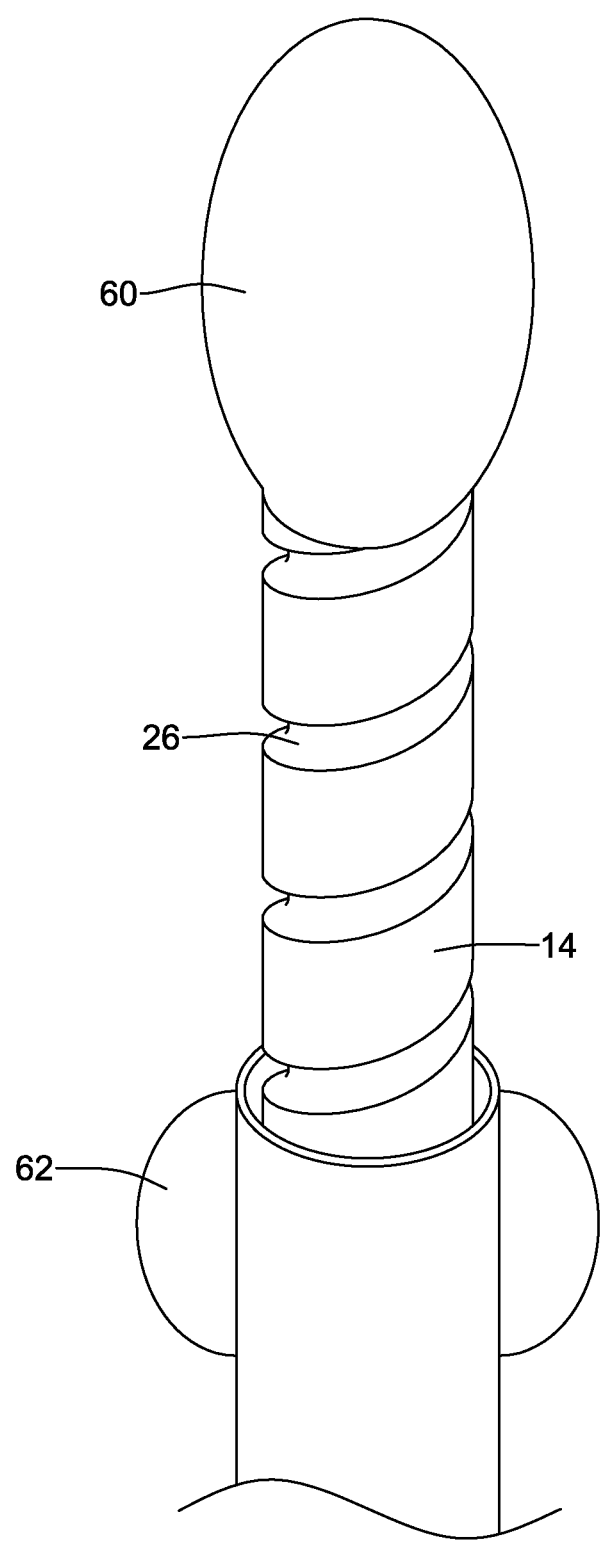
FIG. 8d is a view of the distal portion of a renal nerve modulation system having centering elements.

FIG. 8D illustrates the distal portion of an embodiment in which the centering elements 60 and 62 are inflatable members. Inflatable member 60 is at the distal end of shaft 14, which in this embodiment would include an inflation lumen. Inflatable member 62 is shown as disposed on sheet 16, which would also include an inflation lumen. Either or both of inflatable members 60 and 62 may have an irregular or non-circular expanded shape to allow for the continued perfusion of blood or may include perfusion lumens (not illustrated). For example, each of inflatable members 60 and 62 may comprise two or more lobes. The inflatable members 60 and 62 may be configured to close off the intervening space or nearly close it off, and one could inject a cooling fluid such as saline between the two balloons.

Figure 9A:
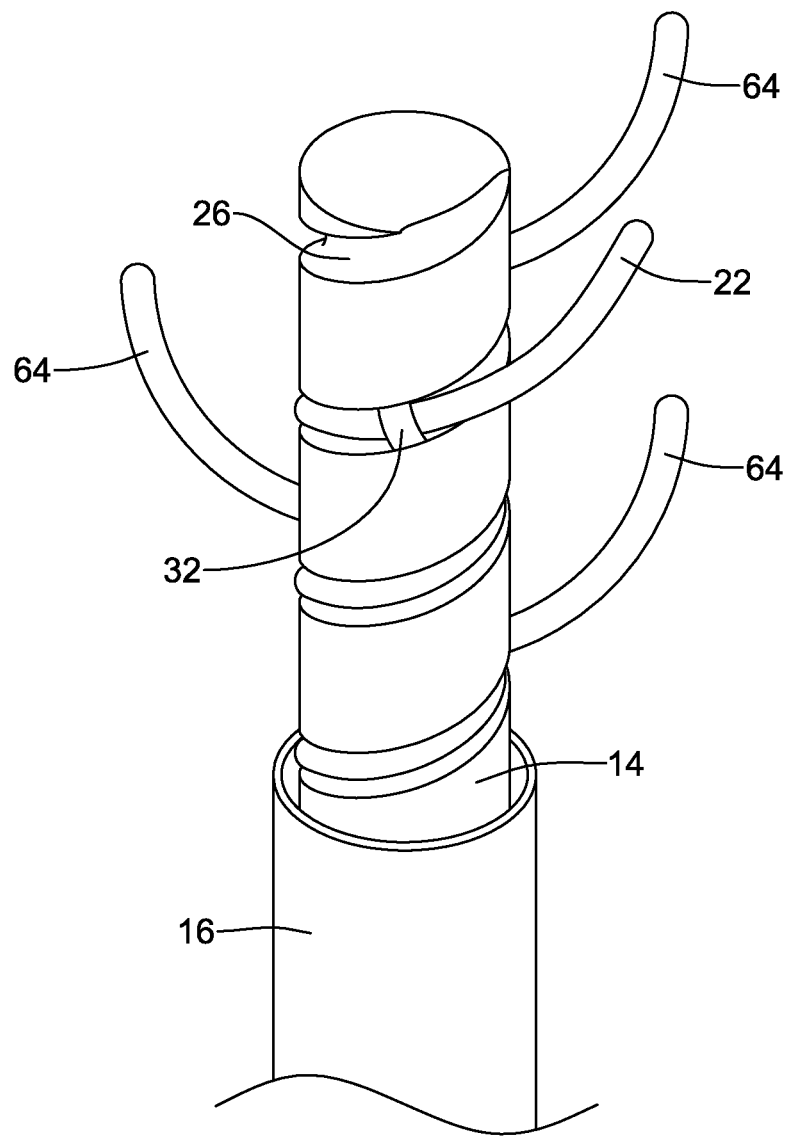
FIG. 9a is a view of the distal portion of a renal nerve modulation system having centering elements.
Figure 9B:
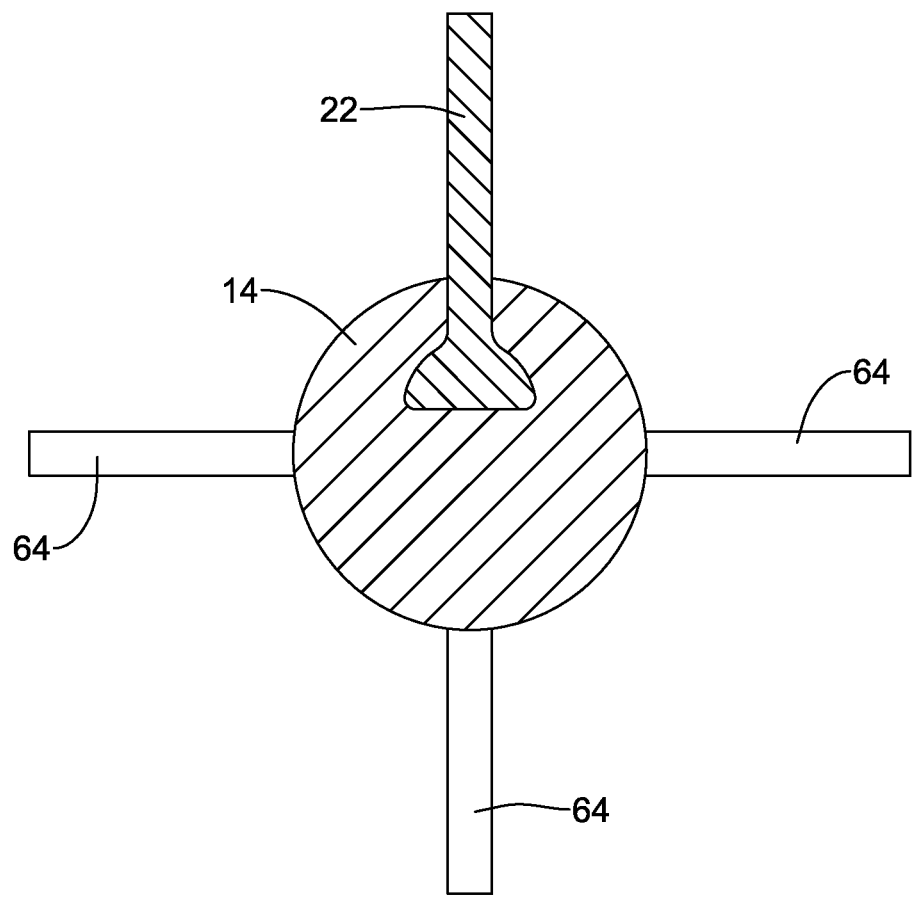

FIG. 9A illustrates the distal portion of an embodiment in which centering elements 64 are disposed on the outer surface of shaft 14 at different longitudinal locations. Like centering elements 50, these are resilient spring members that expand upon the retraction of sheet 16. Because electrode 22 is moved helically in the groove 26 during operation, centering elements 64 do not interfere with the electrode during the process. FIG. 9B is a cross-sectional view illustrating the radial position of centering elements 64, which are disposed substantially uniformly about the circumference of the shaft 14.

It is contemplated that in some embodiments the centering elements 50, 52, 54, 56, 60, 62 and 64 are sized such that when the centering elements are deployed or expanded, the element or combination of elements extend fully to the vessel wall. In such embodiments, the centering elements have a radial extent that is approximately equal to that of the electrode(s). In other embodiments, the centering elements may be somewhat smaller so that the combination of centering elements by themselves do not span the vessel. Instead, the centering elements are sized so that the combination of the electrode(s) and centering element(s) span the vessel. Such embodiments may allow for freer perfusion and movement of the electrode(s).

Figure 10:
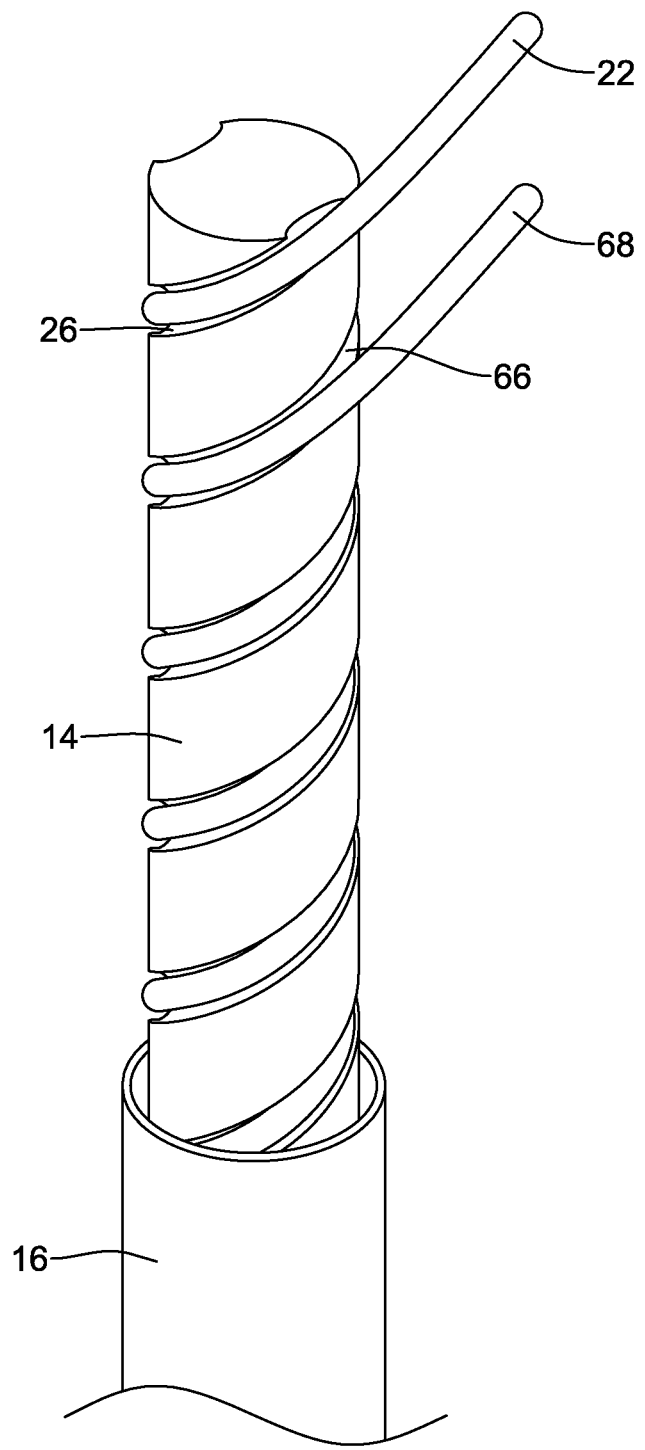
FIG. 10 is a view of the distal portion of a renal nerve modulation system having a multi-groove shaft such as that illustrated in FIG. 4c.

FIG. 10 illustrates the distal portion of an embodiment of that includes in shaft 14 the first groove 26 and a second parallel helical groove 66. In first groove 26 is the first electrode 22 and a corresponding second electrode 68 is disposed in the second groove 66 (conductors 24 are not illustrated).

Figure 11A:
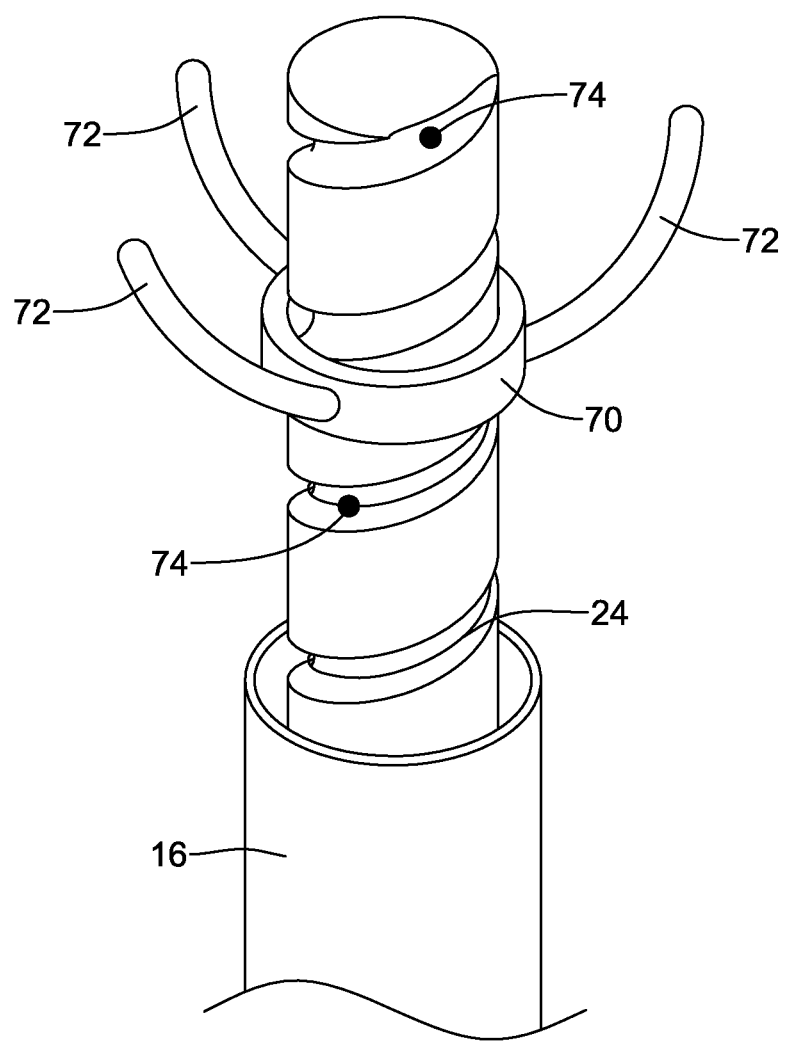
FIG. 11a is a view of the distal portion of a renal nerve modulation system.

FIG. 11A illustrates the distal portion of an embodiment having a ring electrode 70 with three centering elements 72. One, two or more of the centering elements 72 may also function as electrodes. As above, centering elements 72 are resilient spring members that expand when sheath 16 is retracted. Contact patches 74 are disposed on central shaft 14. Two are illustrated although it is contemplated that 2, 3, 4, 5, 6 or more may be included on the shaft. Power may run through the shaft. As the ring electrode is pulled proximally down the shaft, it makes contact with the contact patches 74 and thereby activates the electrode(s) automatically at predetermined intervals.

Figure 11B:
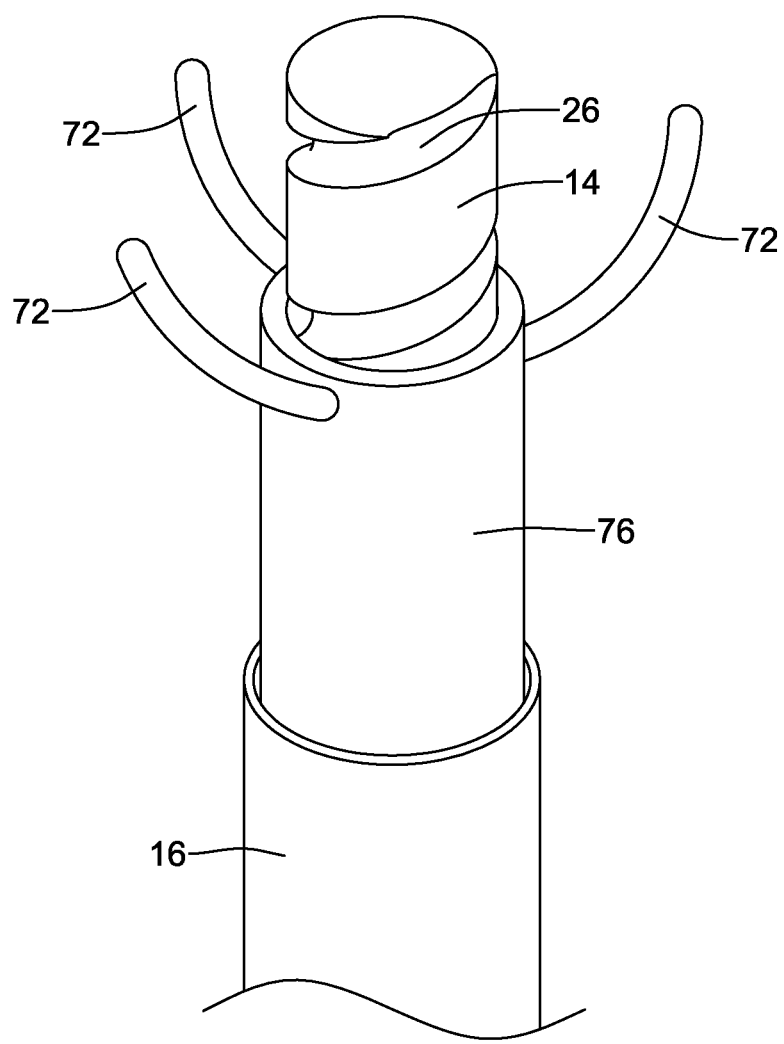
FIG. 11b is a view of the distal portion of a renal nerve modulation system.

FIG. 11B illustrates the distal portion of an embodiment where the centering elements 72 (one or more of which is an electrode) are disposed on the distal portion of a cylinder 76. This embodiment may include the contact patches as described above. Such contact patches may be disposed anywhere along the shaft under cylinder 76.

Figure 12:
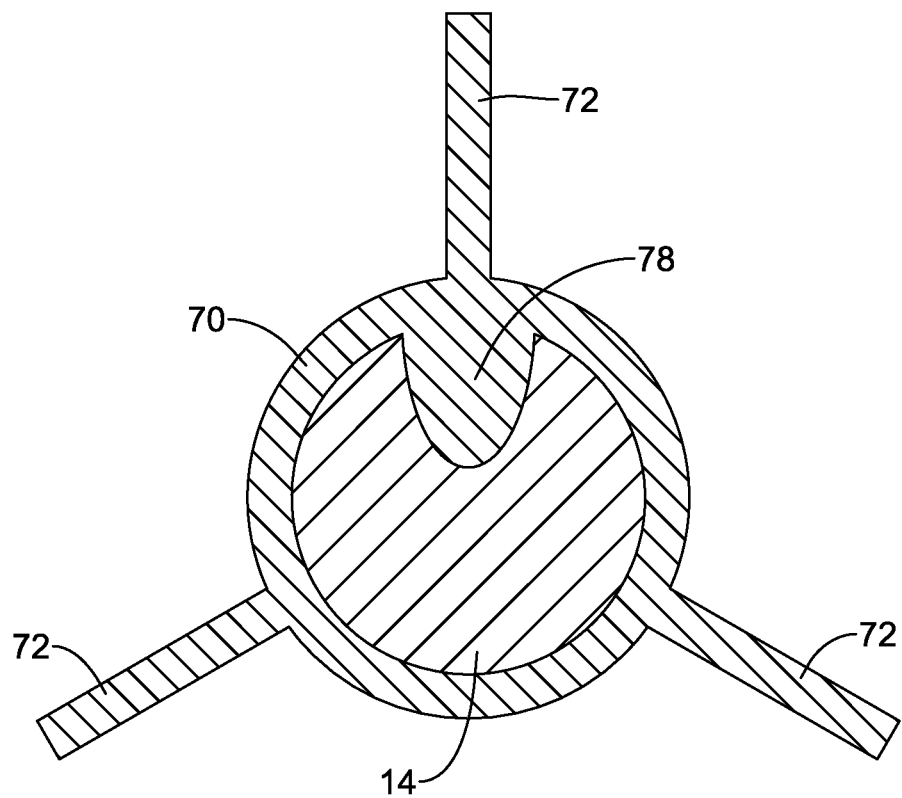
FIG. 12 is a cross-sectional view consistent with the renal nerve modulation systems of either FIG. 11a or 11b.

FIG. 12 is a cross-sectional view illustrating ring electrode 70 (or the cylinder 76) with centering elements 72 disposed thereon. A key 78 engages with the groove 26 of the shaft and may be used to make electrical contact with the contact patches 74. It can be appreciated with respect to this view that the shaft 14 of FIG. 5C having the rail 42 may be readily used with a variation of these embodiments of FIGS. 11A and 11B.

Figure 13:
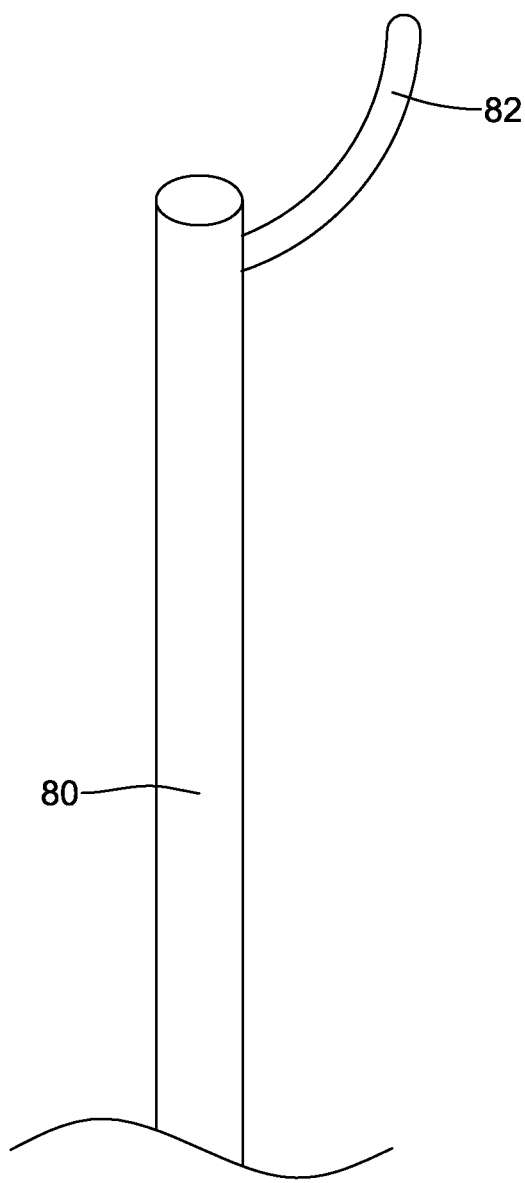
FIG. 13 is a distal view of a central shaft of a renal nerve modulation system.
Figure 14:
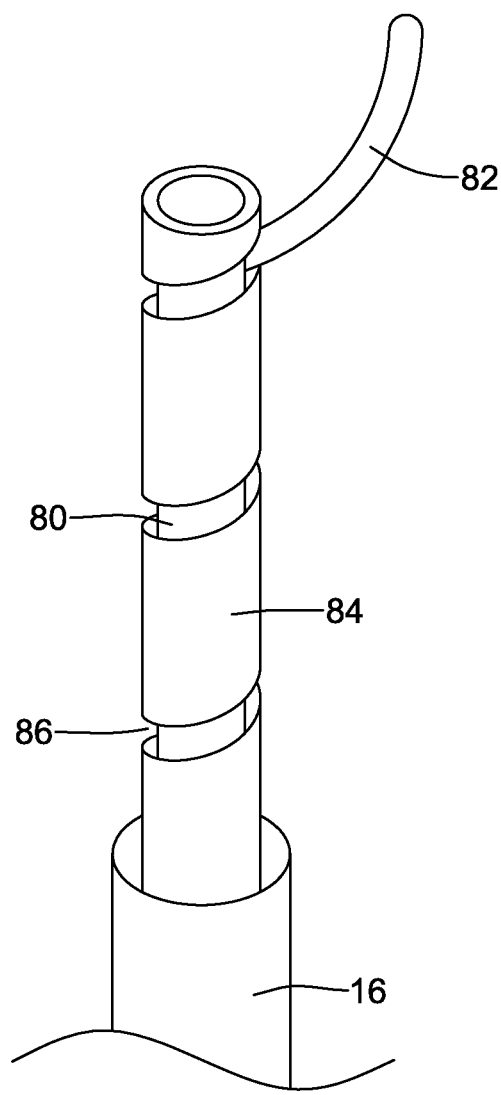
FIG. 14 is a distal view of a renal nerve modulation system using the central shaft of FIG. 13.

FIG. 13 illustrates a distal end of an embodiment where the electrode 82 is carried on a central shaft 80. The central shaft 80 is used in conjunction with the hollow cylinder 84 of FIG. 14. The cylinder 84 includes a helical slot 86 through which the electrode is disposed. As shaft 80 is pulled proximally, the electrode 82 tracks proximally and radially the helical slot 86.

Figure 15A:
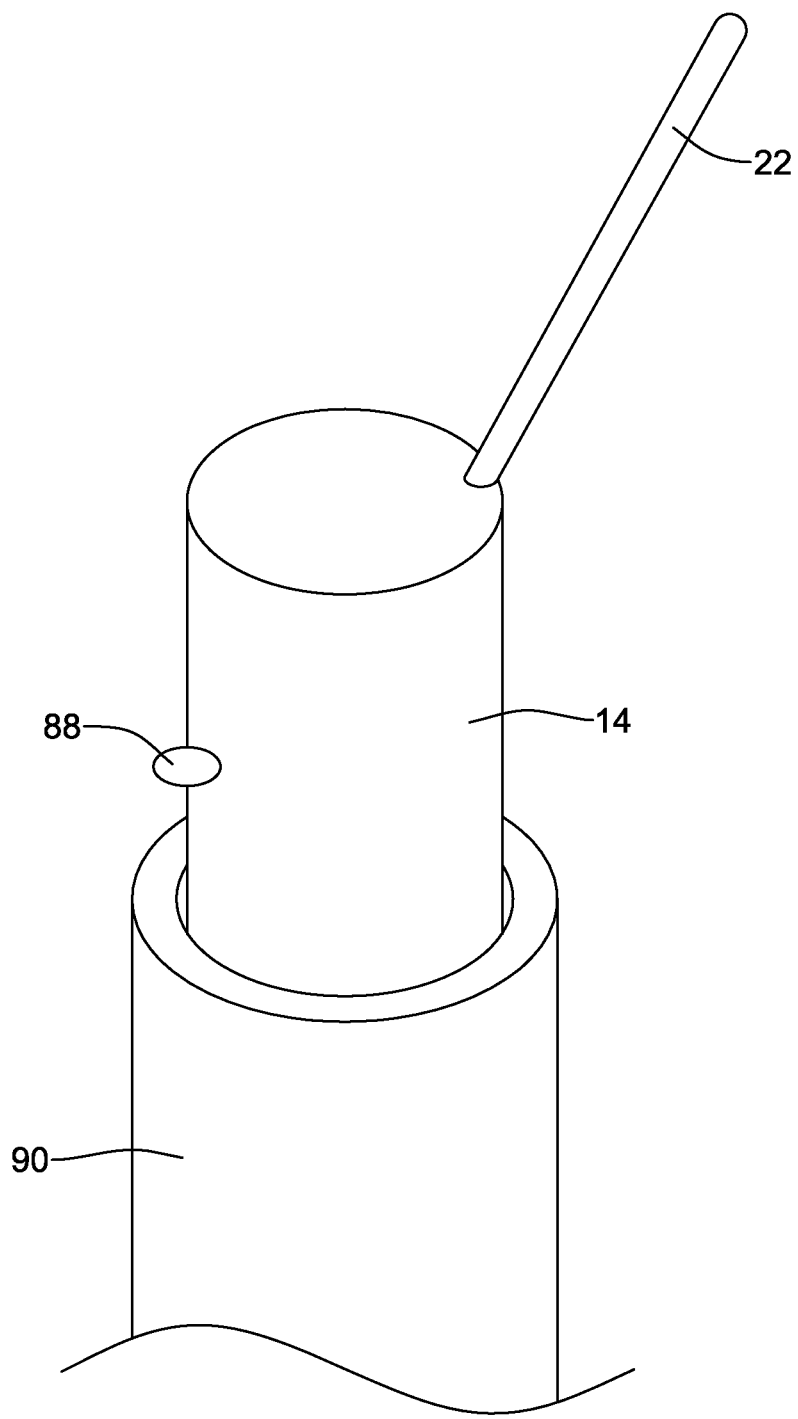
FIG. 15a is a view of the distal portion of a renal nerve modulation system.
Figure 15B:
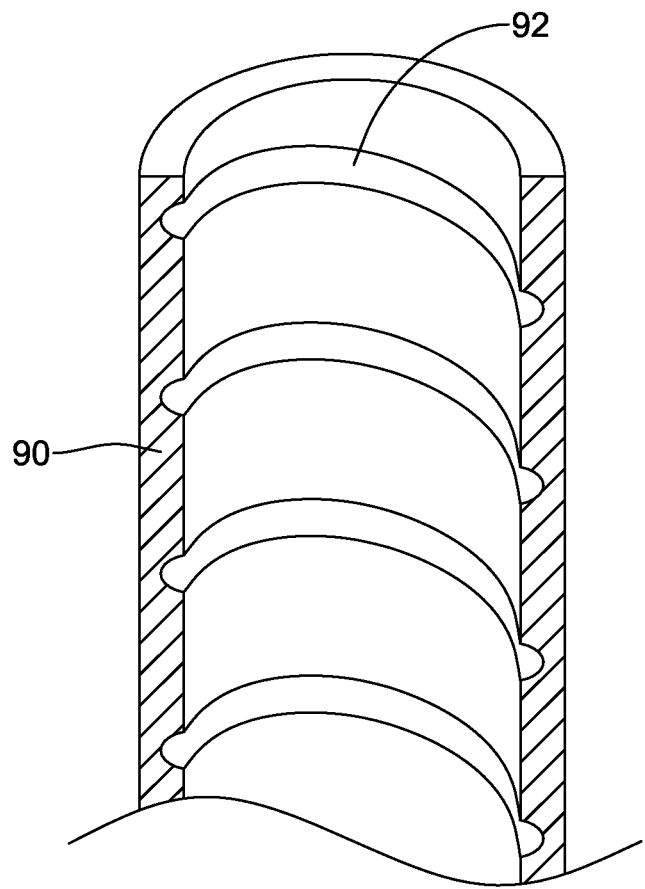

FIG. 15A illustrates a distal end of an embodiment where the electrode 22 is carried on a central shaft 14. A knob 88 interfaces with a helical groove 92 of sheath 90 (illustrated in FIG. 15B to cause the central shaft 14 to rotate. Centering elements such as centering elements 72 described above may be attached to sheath 90. Alternative to knob 88, a helical rail could be disposed on shaft 14 to interface with helical groove 92.

Imaging elements such as radiopaque rings or other elements may be placed on any of the components described above to aid in visualization. Such elements typically include a metal such as gold or platinum as is know in the art. An irrigation lumen may also be included or the sheath may be fluidly attached to an irrigation supply. Irrigation may be used for visualization, cooling or other therapeutic purpose.

In some embodiments, a graspable proximal portion of the elongate electrode carrying element 12 or shaft 80 may include a bushing or swivel joint to allow free rotation of the elongate electrode carrying element 12 while it is being pulled proximally. A user might grasp the elongate electrode carrying element 12 on a bushing or proximal of a swivel joint and thus avoid any potential kinking or other bending of the elongate electrode carrying element 12 as the electrode 22 rotates radially.

The centering elements are shown on certain of the embodiments but it is to be understood that the centering elements may be incorporated into any of the embodiments as appropriate. For example, the distal centering elements 50, the distal centering elements 54 or the distal balloon 60 may be readily attached to the shafts of the embodiments of FIG. 2, 7, 9A, 10, 11A, 11B or on the distal ends of the shafts of FIGS. 5A, 5B and 5C or on the shaft 80 or cylinder 84 of the embodiment of FIG. 14.

Similarly, the contact patches 74 are described with respect to the embodiment of FIG. 11A, but can be incorporated in any of the other embodiments. For example, the contact patches may be incorporated into the embodiments described above with respect to FIGS. 2, 5A, 5B, 5C, 6, 7, 8A, 8B, 8C, 8D, 9A, 9B, 10, 11B, 12, 13 and 14.

Suitable materials are polymers and metals as are known in the art. The sheath may have more than one layer include lubricious inner and outer layers and may include a reinforcing element such as a coil or braid. The other elements may be made of conductive materials having a suitable coating to avoid unwanted conductivity or may be non-conductive materials such as polymers with conductive elements embedded therein.

In use, guide wires and guide catheters may be used to place the system as is conventional in intravascular techniques as is needed or preferred. Once in place, the sheath is withdrawn distally to deploy the electrode(s) and any centering elements. The electrode(s) are then withdrawn proximally relative to the shaft by pulling a proximal portion of the elongate electrode carrying element 12 or shaft 80 proximally relative to shaft 14 or cylinder 84. During this relative proximal movement, the electrode(s) is activated as desired. In one example activation pattern, the electrode is activated over discontinuous segments of a helical path. Subsequently, the elements are withdrawn into the sheath and then the system is withdrawn from the body.

In another example use, when the sheath is withdrawn a pre-determined distance, it engages with a portion of the elongate electrode carrying member to fix relative longitudinal movement between the sheath and the elongate electrode carrying member. Subsequent proximal withdrawal of the sheath then moves the electrode proximally as well. Optionally, after the sheath/carrying member combination is withdrawn a further predetermined distance, the shaft then engages with the carrying member to fix relatively longitudinal movement between these two elements. As this point, the sheath is either manually or automatically disengaged from the then longitudinally fixed carrying member/shaft, which can then be withdrawn into the sheath for retraction of the system from the body. Certain modifications to the proximal portions or in some cases to further distal portions of the elements may be necessary to use the described method.

The above method may be used with any of the embodiments, but may be particularly advantageous used with an embodiment that includes contact patches as described with respect to FIG. 11A. Such a method of use further simplifies the actions of the doctors.

Further, irrigation for the purpose of visualization, cooling or other therapy may be used with any of the above methods.

Those skilled in the art will recognize that the present invention may be manifested in a variety of forms other than the specific embodiments described and contemplated herein. Accordingly, departure in form and detail may be made without departing from the scope and spirit of the present invention as described in the appended claims.

What is claimed is:
1. A system for nerve modulation, comprising:
a first elongate element having a distal end and a proximal end, a groove extending along the first elongate element forming a helical guide having a proximal end and a distal end, the helical guide extending around the first elongate element and along a length of the first elongate element;
a second elongate element having a distal end and a proximal end, the second elongate element including an atraumatic ablation element proximate the distal end of the second elongate element, the second elongate element movably disposed within and extending along the groove such that the second elongate element is wrapped around the first elongate element; and a sheath disposed about both the first and second elongate elements, wherein pulling proximally on the proximal end of the second elongate element causes simultaneous radial and longitudinal displacement of the ablation element by causing the second elongate element to slide within the helical guide.

2. The system of claim 1, wherein the groove has a lead and a pitch wherein the lead is greater than the pitch.

3. The system of claim 1, wherein the groove also includes a proximal straight section.

4. The system of claim 1, wherein the groove terminates distal of the proximal end of the first elongate element.

5. The system of claim 1, wherein the groove has a mouth and has a cross-sectional shape that is narrower at the mouth than at a dimension parallel to the mouth and deeper within the groove.

6. The system of claim 5, wherein the ablation element has a base portion slidably engaged with the groove.

7. The system of claim 1, wherein the first elongate element further comprises a plurality of resiliently expandable centering legs.

8. The system of claim 7, wherein the legs are disposed at the distal end of the first elongate element.

9. The system of claim 7, wherein the legs are distributed radially and longitudinally about the helical guide between the proximal end and the distal end of the helical guide.

10. The system of claim 1, wherein the second elongate element comprises a ring at a proximal end of the ablation element and a pull element extending proximally from the ring and disposed on one side of the first elongate element.

11. The system of claim 10, further comprising a plurality of centering struts attached to the ring.

12. The system of claim 1, wherein the sheath comprises a cylinder disposed about a majority of the length of the first elongate element.

13. The system of claim 1, wherein the first elongate element further comprises a plurality of electrical contact patches disposed longitudinally along the first elongate element such that the nerve modulation element is activated at predetermined relative positions of the first and second elongate elements.

14. The system of claim 13, wherein a power source is operatively connected to the second elongate element and wherein electrical power may be transmitted through the second elongate element to the ablation element at the predetermined relative positions.

\* \* \* \* \*